(12) United States Patent
Matheny

(10) Patent No.: US 10,945,838 B2
(45) Date of Patent: *Mar. 16, 2021

(54) PROSTHETIC CARDIOVASCULAR VALVES AND METHODS FOR REPLACING NATIVE ATRIOVENTRICULAR VALVES WITH SAME

(71) Applicant: CorMatrix Cardiovascular, Inc., Roswell, GA (US)

(72) Inventor: Robert G Matheny, Norcross, GA (US)

(73) Assignee: Co-Matrix Cardiovascular, Inc., Roswell, GA (US)

(*) Notice: Subject to any disclaimer, the term of this patent is extended or adjusted under 35 U.S.C. 154(b) by 27 days.

This patent is subject to a terminal disclaimer.

(21) Appl. No.: 16/553,570

(22) Filed: Aug. 28, 2019

(65) Prior Publication Data

US 2020/0022808 A1    Jan. 23, 2020

Related U.S. Application Data

(63) Continuation-in-part of application No. 16/238,730, filed on Jan. 3, 2019, now Pat. No. 10,857,263, and a continuation-in-part of application No. 16/193,669, filed on Nov. 16, 2018, and a continuation-in-part of application No. 16/129,968, filed on Sep. 13, 2018, and a continuation-in-part of application No. 15/206,833, filed on Jul. 11, 2016, now Pat. No. 10,188,510, and a continuation-in-part of application No. 14/960,354, filed on Dec. 5, 2015, now Pat. No. 9,907,649, and a continuation-in-part of application No. 14/229,854, filed on Mar. 29, 2014, now Pat. No. 9,308,084.

(51) Int. Cl.
*A61F 2/24* (2006.01)

(52) U.S. Cl.
CPC .......... *A61F 2/2418* (2013.01); *A61F 2/2409* (2013.01); *A61F 2/2412* (2013.01); *A61F 2/2433* (2013.01); *A61F 2/2436* (2013.01); *A61F 2/2454* (2013.01); *A61F 2220/0008* (2013.01); *A61L 2430/20* (2013.01)

(58) Field of Classification Search
CPC ..... A61F 2/2454; A61F 2/2469; A61F 2/2433
See application file for complete search history.

(56) References Cited

U.S. PATENT DOCUMENTS

| | | | | |
|---|---|---|---|---|
| 2013/0172978 A1* | 7/2013 | Vidlund | ............... | A61F 2/2439 623/1.12 |
| 2016/0317293 A1* | 11/2016 | Matheny | ................. | A61L 27/54 |
| 2017/0312078 A1* | 11/2017 | Krivoruchko | ......... | A61F 2/2418 |

FOREIGN PATENT DOCUMENTS

WO    WO-2016/050751 A1    4/2016

* cited by examiner

*Primary Examiner* — Megan Y Wolf
(74) *Attorney, Agent, or Firm* — Francis Law Group

(57) ABSTRACT

A percutaneous transseptal surgical implantation method for replacing a defective atrioventricular (AV) valve with a conical shaped prosthetic valve formed from a polymeric composition. When the method is employed to replace a native mitral valve, the method positions the prosthetic valve in the mitral valve region, whereby the valve does not obstruct the outflow tract of the aortic valve and prevents the leaflets of the aortic valve from coapting.

4 Claims, 47 Drawing Sheets

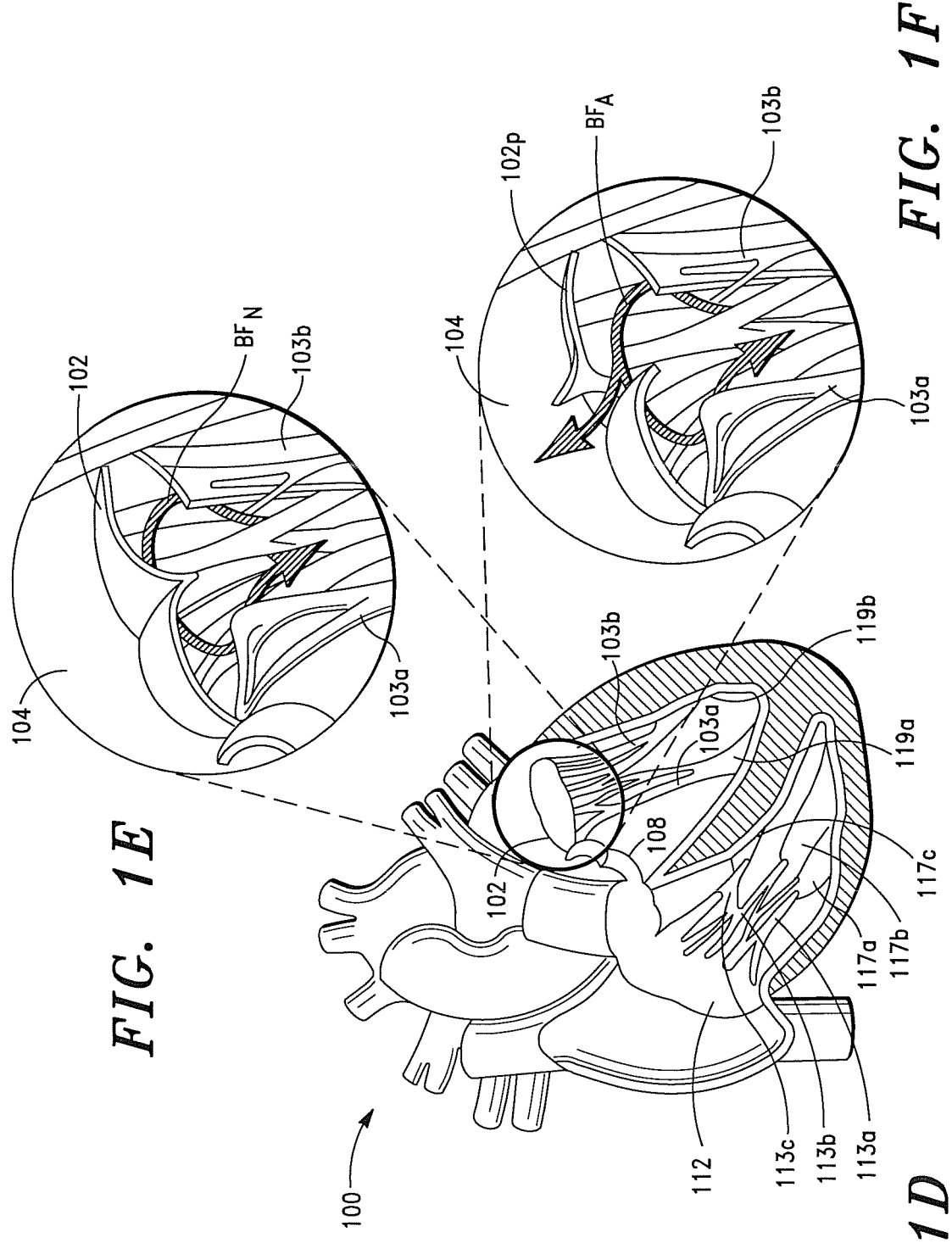

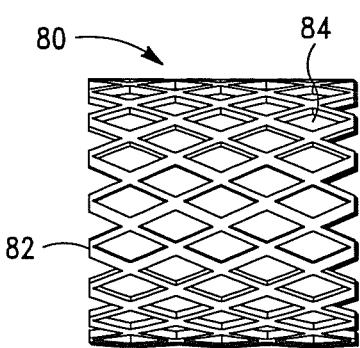
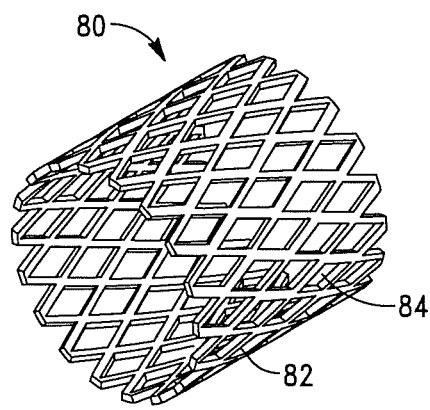
FIG. 2A
FIG. 2B
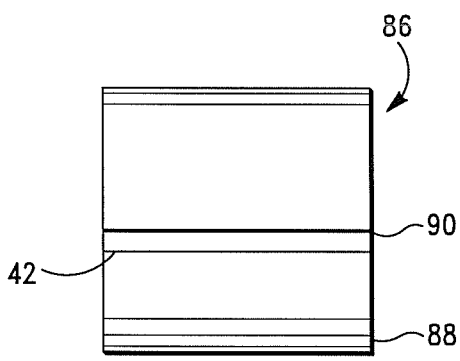
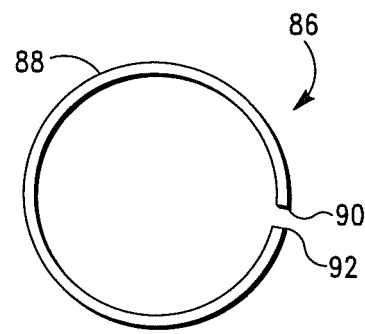
FIG. 3A
FIG. 3B
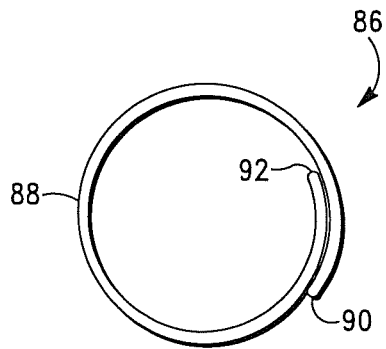
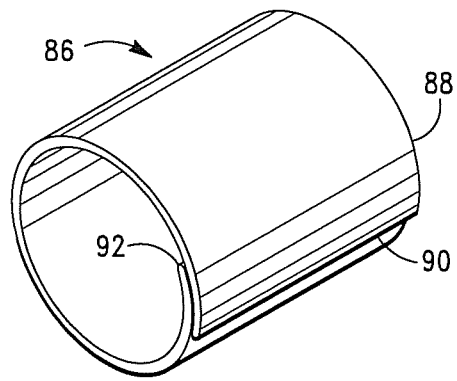
FIG. 4A
FIG. 4B

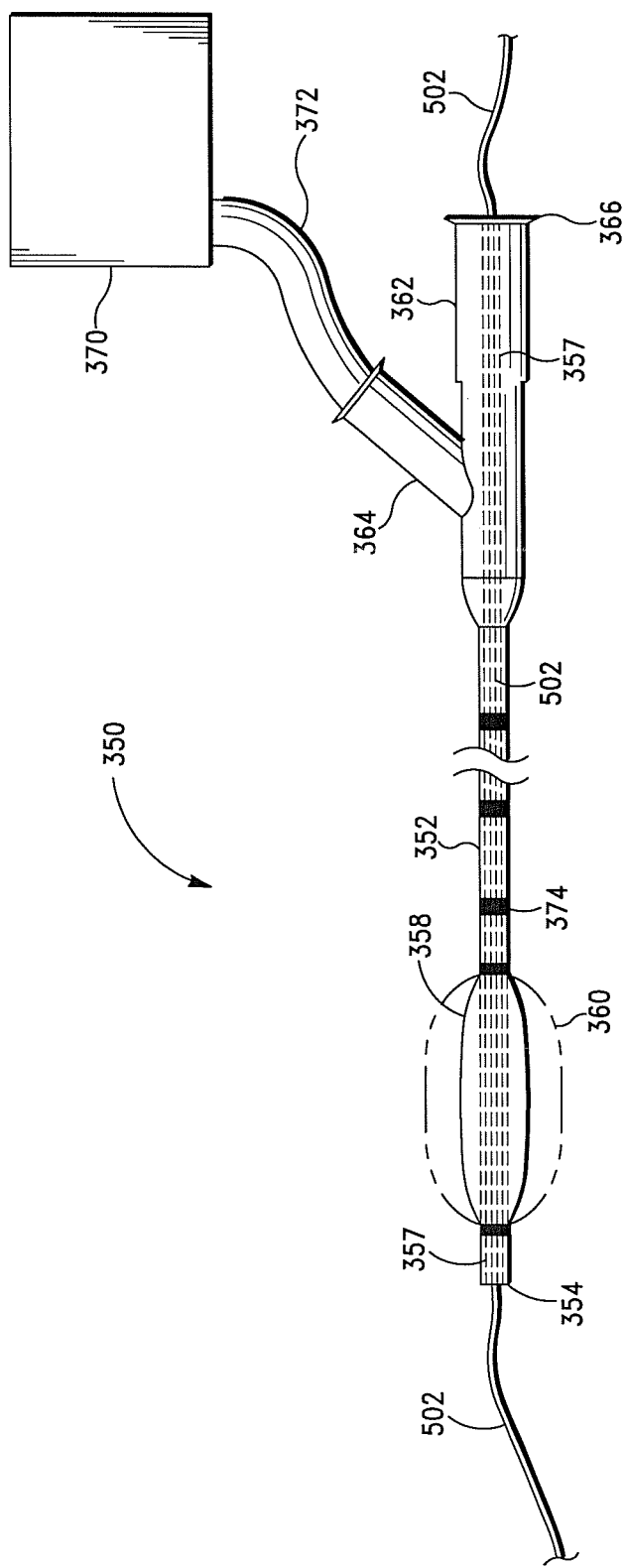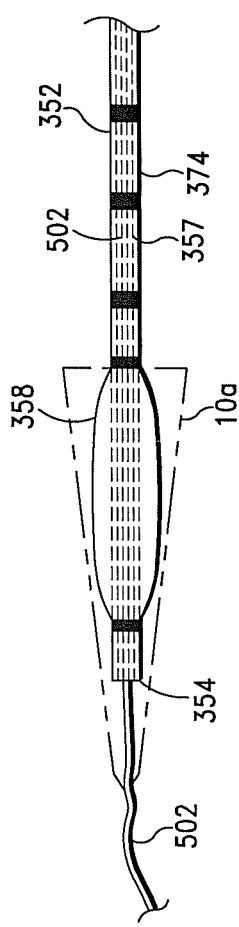
FIG. 16A
FIG. 16B

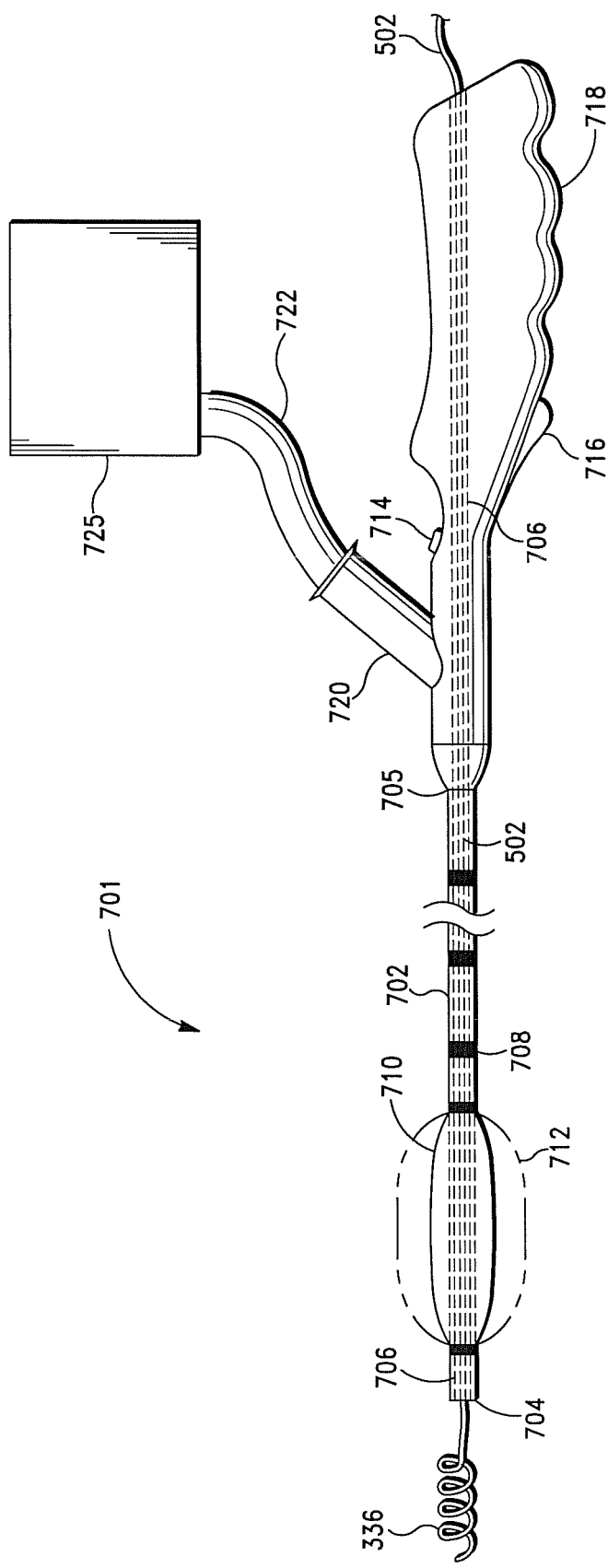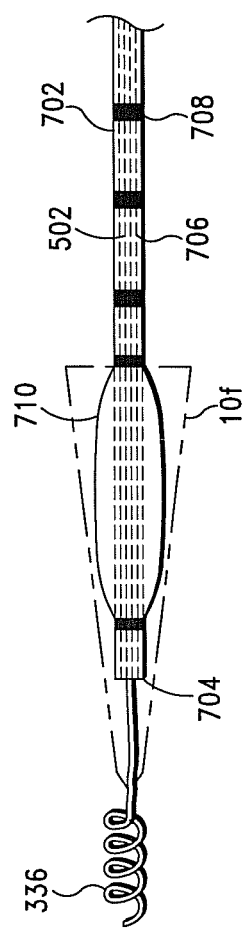
FIG. 35
FIG. 36

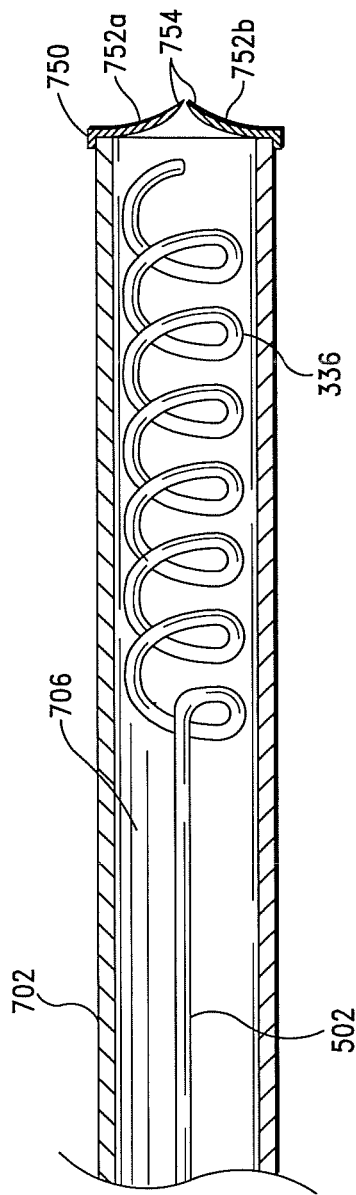
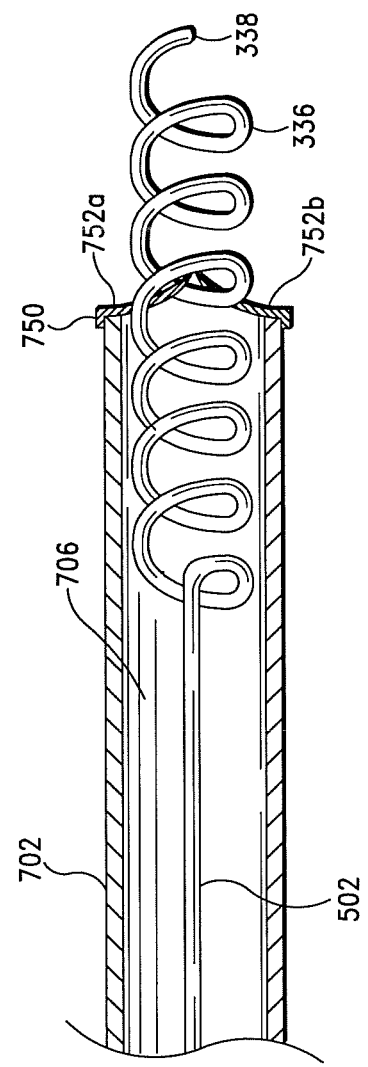

PROSTHETIC CARDIOVASCULAR VALVES AND METHODS FOR REPLACING NATIVE ATRIOVENTRICULAR VALVES WITH SAME

CROSS-REFERENCE TO RELATED APPLICATIONS

This application is a continuation-in-part of U.S. application Ser. No. 16/238,730, filed on Jan. 3, 2019, which is a continuation-in-part of U.S. application Ser. No. 16/193,669, filed on Nov. 16, 2018, which is a continuation-in-part of U.S. application Ser. No. 16/129,968, filed on Sep. 13, 2018, which is a continuation-in-part of U.S. application Ser. No. 15/206,833, filed on Jul. 11, 2016, now U.S. Pat. No. 10,188,510, which is a continuation-in-part application of U.S. application Ser. No. 14/960,354, filed on Dec. 5, 2015, now U.S. Pat. No. 9,907,649, which is a continuation-in-part application of U.S. application Ser. No. 14/229,854, filed on Mar. 29, 2014, now U.S. Pat. No. 9,308,084, which claims priority to U.S. Provisional Application No. 61/819,232, filed on May 3, 2013.

FIELD OF THE INVENTION

The present invention generally relates to prosthetic valves for replacing defective cardiovascular valves. More particularly, the present invention relates to prosthetic cardiovascular valves and methods for replacing native atrioventricular (AV) valves with same.

BACKGROUND OF THE INVENTION

As is well known in the art, the human heart has four valves that control blood flow circulating through the human body. Referring to FIGS. 1A and 1B, on the left side of the heart 100 is the mitral valve 102, located between the left atrium 104 and the left ventricle 106, and the aortic valve 108, located between the left ventricle 106 and the aorta 110. Both of these valves direct oxygenated blood from the lungs into the aorta 110 for distribution through the body.

The tricuspid valve 112, located between the right atrium 114 and the right ventricle 116, and the pulmonary valve 118, located between the right ventricle 116 and the pulmonary artery 120, however, are situated on the right side of the heart 100 and direct deoxygenated blood from the body to the lungs.

Referring now to FIGS. 1C and 1D, there are also generally five papillary muscles in the heart 100; three in the right ventricle 116 and two in the left ventricle 106. The anterior, posterior and septal papillary muscles 117a, 117b, 117c of the right ventricle 116 each attach via chordae tendinae 113a, 113b, 113c to the tricuspid valve 112. The anterior and posterior papillary muscles 119a, 119b of the left ventricle 106 attach via chordae tendinae 103a, 103b to the mitral valve 102 (see also FIG. 1E).

Since cardiovascular valves, including heart valves, are passive structures that simply open and close in response to differential pressures, the issues that can develop with valves are typically classified into two categories: (i) stenosis, in which a valve does not open properly, and (ii) insufficiency (also called regurgitation), in which a valve does not close properly.

Stenosis and insufficiency can occur as a result of several abnormalities, including damage or severance of one or more chordeae or several disease states. Stenosis and insufficiency can also occur concomitantly in the same valve or in different valves.

Both of the noted valve abnormalities can adversely affect organ function; especially, heart function, and result in heart failure. By way of example, referring first to FIG. 1E, there is shown normal blood flow (denoted "$BF_N$") proximate the mitral valve 102 during closure. Referring now to FIG. 1F, there is shown abnormal blood flow (denoted "$BF_A$") or regurgitation caused by a prolapsed mitral valve 102p. As illustrated in FIG. 1F, the regurgitated blood "$BF_A$" flows back into the left atrium, which can, if severe, result in heart failure.

In addition to stenosis and insufficiency of a valve, surgical intervention may also be required for certain types of bacterial or fungal infections, wherein the valve may continue to function normally, but nevertheless harbors an overgrowth of bacteria (i.e. "vegetation") on the valve leaflets. The vegetation can, and in many instances will, flake off (i.e. "embolize") and lodge downstream in a vital artery.

If such vegetation is present on a valve on the left side (i.e., the systemic circulation side) of the heart, embolization can, and often will, result in sudden loss of the blood supply to the affected body organ and immediate malfunction of that organ. The organ most commonly affected by such embolization is the brain, in which case the patient can, and in many instances will, suffer a stroke.

Likewise, bacterial or fungal vegetation on a tricuspid valve can embolize to the lungs. The noted embolization can, and in many instances will, result in lung dysfunction.

Treatment of the noted valve dysfunctions typically comprises reparation of the diseased valve with preservation of the patient's own valve or replacement of the valve with a mechanical or bioprosthetic valve, i.e. a prosthetic valve.

Various prosthetic valves have thus been developed for replacement of native diseased or defective valves. The selection of a particular type of replacement valve depends on many factors, such as the location of the diseased or defective native valve, the age and other specifics of the recipient of the replacement heart valve, and the surgeon's experiences and preferences.

Commonly used replacement cardiovascular valves (also referred to hereinafter as "heart valves") are typically classified in the following three groups: (i) mechanical valves, (ii) allograft tissue valves, and (iii) xenograft tissue valves. Each of the noted valves and disadvantages associated with same are discussed in detail below.

Mechanical Heart Valves

As is well known in the art, mechanical heart valves, such as caged-ball valves, bi-leaflet valves, and tilting disk valves, typically comprise various metal and polymeric components, which can, and in most instances will, induce an adverse inflammatory response when implanted in a patient or subject.

A further disadvantage associated with mechanical heart valves is that such valves also have a propensity to cause the formation of blood clots after implantation in a patient. If such blood clots form on the mechanical valve, they can preclude the valve from opening or closing correctly or, more importantly, can disengage from the valve and embolize to the brain, causing an embolic stroke. Thus, recipients of a mechanical heart valve are typically required to take systemic anticoagulant drugs for the rest of their lives. In addition to being expensive, these anticoagulant drugs can themselves be dangerous in that they can cause abnormal bleeding in the recipient or patient that can lead to a hemorrhagic stroke.

A further disadvantage associated with mechanical heart valves is that such valves often have large and cumbersome skirt attachments that partially extend into the left atrium and the left ventricle when implanted in a mitral valve region. The skirt attachment can, and often will, impair aortic valve function by obstructing the outflow tract of the aortic valve and preventing the leaflets of the adjacent aortic valve from coapting. In some instances, mechanical heart valves and many other conventional prosthetic valves can reduce the blood outflow rate of the aortic valve by up to 50%.

The risks and complications associated with impaired aortic valve function typically include left ventricular hypertrophy with fibrosis, systolic dysfunction (a decrease in the ejection fraction), diastolic dysfunction (elevated filling pressure of the LV), and in severe cases, congestive heart failure.

Further, mechanical heart valves with and without the skirt attachments are notoriously difficult to implant and often require large and cumbersome catheter assemblies for percutaneous or transapical implantation. These large catheter assemblies are excessively difficult to operate during a percutaneous or transapical implantation procedure.

Allograft Tissue Valves

Allograft tissue valves are harvested from human sources, such as human cadavers. Unlike mechanical heart valves, allograft tissue valves typically do not promote blood clot formation and, therefore, avoid the need for prescribing an anticoagulant medication for the recipient or patient. However, there are still several drawbacks and disadvantages associated with allograft tissue valves.

A major drawback of allograft tissue valves is that such valves are not available in sufficient numbers to satisfy the needs of all patients who need new heart valves.

A further drawback of allograft tissue valves is that recipients of allograft tissue valves, i.e. patients, are typically required to take systemic antirejection and/or immunosuppressive drugs for a predetermined period of time and, in some instances, for a lifetime. Although antirejection and/or immunosuppressive drugs increase the possibility that a patient will accept an allograft without complications, the drugs will often leave the recipient vulnerable to a plurality of other infectious diseases, including bacterial infections, fungal infections, viral infections and the like.

Various significant complications have also been encountered when allograft tissue valves have been used to replace native atrioventricular (AV) valves. The complications include, for example, the recipient's rejection of the allograft tissue valve leading to transplant rejection and further complications resulting therefrom. Another complication is the onset of Graft-Versus-Host disease.

Further, allograft tissue valves are generally more difficult to implant than mechanical valves or xenograft tissue valves. Because of the implantation difficulties, the operative risk associated with allograft tissue valves is often greater than the operative risks associated with mechanical valves and xenograft tissue valves.

Xenograft Tissue Valves

Xenograft tissue valves are formed from non-human tissue sources, such as cows or pigs. Xenograft tissue valves are typically classified in two groups: (i) conventional non-remodelable tissue valves and/or tissue valves that do not have the capacity to induce remodeling of damaged native tissue, i.e. cardiovascular tissue, and regeneration of new cardiovascular tissue when implanted in a recipient, and (ii) remodelable tissue valves that also have the capacity to induce remodeling of damaged native cardiovascular tissue and regeneration of new cardiovascular tissue when implanted in a recipient.

Xenograft tissue valves (remodelable and non-remodelable) are similarly less likely to cause blood clot formation than comparable mechanical valves. Thus, patients that receive xenograft tissue valves are not always required to take anticoagulant medications.

Conventional xenograft tissue valves are, however, prone to calcification and lack the long-term durability of mechanical valves and, consequently, require frequent replacement as compared to mechanical valves. A major factor that contributes to these failures is the chemical treatment that conventional xenograft tissue valves are typically subjected to, e.g., crosslinking, to reduce antigenicity of the animal tissue. Without the chemical treatment(s), conventional xenograft tissue valves can, and in many instances will, induce an adverse inflammatory response when implanted in a patient.

More recently, remodelable xenograft tissue valves comprising decellularized extracellular matrix (ECM) have been developed and employed to replace various heart valves. As indicated above, such valves have the capacity to remodel, i.e. form valve structures similar to native valve structures when implanted in a patient, and inducing remodeling of native cardiovascular tissue and regeneration of new cardiovascular tissue when implanted in a patient.

Illustrative are the prosthetic xenograft ECM tissue valves disclosed in Applicant's U.S. Pat. Nos. 9,308,084, 9,011,526, 8,709,076, 9,044,319, 8,845,719, 8,409,275, 8,696,744, 8,709,076, 8,790,397, 8,257,434 and 7,998,196, and Co-Pending U.S. application Ser. No. 13/804,683.

Although prosthetic xenograft ECM tissue valves substantially reduce and, in most instances, eliminate the major disadvantages and drawbacks associated with mechanical valves, allograft tissue valves, and conventional xenograft tissue valves, there remained a need for improved xenograft ECM tissue valves, i.e. pre-formed ECM valve templates thereof, with enhanced pre-remodeling structural integrity and function.

The noted need was effectively addressed via the development of the conical shaped ECM prosthetic valves disclosed in Applicant's issued U.S. Pat. Nos. 9,907,649 and 10,052,409, and Co-pending U.S. application Ser. Nos. 16/129,968, 15/206,814, 15/206,833, 15/206,871 and 15/877,629 described herein.

Implantation of a prosthetic valve, including mechanical valves and bioprosthetic valves, requires a great deal of skill and concentration given the delicate nature of the native cardiovascular tissue and the spatial constraints of the surgical field. It is also critical to achieve a secure and reliable attachment of the valve to host cardiovascular tissue to eliminate complications associated therewith, such as valvular leaks.

Various structures and means have thus been developed to provide a secure and reliable attachment of a prosthetic valve to host cardiovascular tissue. As indicated above and described in detail in Applicant's U.S. application Ser. No. 14/953,548, in some instances, a sewing ring or anchor is employed to attach the proximal end of the prosthetic valve to the cardiovascular structure, e.g., valve annulus.

As also described in Applicant's U.S. application Ser. No. 16/129,968, the distal end of the prosthetic valve is typically connected to one or more papillary muscles.

A major drawback of the noted attachment of a prosthetic valve to a cardiovascular structure; more particularly, a papillary muscle is that the attachment of the distal end of the valve to the papillary muscle can, and in most instances will obstruct the outflow tract of the adjacent aortic valve.

There is thus a need to provide improved prosthetic valves and methods for attaching same to cardiovascular structures and/or tissue that maintain or enhance the structural integrity of the valve when subjected to cardiac cycle induced stress, and do not obstruct the outflow tract of the adjacent aortic valve.

It is therefore an object of the present invention to provide improved prosthetic valves and methods for attaching same to cardiovascular structures and/or tissue that maintain or enhance the structural integrity of the valve when subjected to cardiac cycle induced stress, and do not obstruct the outflow tract of the adjacent aortic valve.

It is another object of the present invention to provide prosthetic valves having means for secure, reliable, and consistently highly effective attachment to cardiovascular structures and/or tissue.

It is another object of the present invention to provide improved methods for securely attaching prosthetic valves to cardiovascular structures and/or tissue.

It is another object of the present invention to provide improved methods for replacing diseased and/or damaged native atrioventricular valves.

SUMMARY OF THE INVENTION

The present invention is directed to methods for replacing diseased or defective heart valves; and, in particular, atrioventricular (AV) valves.

In one preferred embodiment of the invention, the method for replacing a diseased or defective AV valve generally comprises the following steps:
(i) providing a prosthetic "ribbon structure" valve having a closed distal end;
(ii) providing a catheter assembly adapted to access the subject's heart, preferably, an AV valve annulus region; the catheter assembly preferably comprising a portal catheter, catheter guide, all-in-one (AIO) valve deployment device, anchor guidewire and anchor;
(iii) preparing a catheter sub-assembly comprising the portal catheter and catheter guide (and guidewire);
(iv) selecting a vein; preferably, the femoral vein, which provides access to an AV valve annulus region;
(v) placing an incision through tissue proximate the vein and through the vein, wherein an opening is provided in the vein;
(vi) inserting the catheter sub-assembly through the incision, into and through the vein and into the right atrium of the subject's heart;
(vii) advancing the catheter sub-assembly into the left atrium of the subject's heart;
(viii) retracting the catheter guide of the catheter sub-assembly through the portal catheter and out of the subject's body;
(ix) positioning the prosthetic valve on the AIO valve deployment device;
(x) inserting the AIO valve deployment device (and anchor guidewire) with the prosthetic valve engaged thereto into the portal catheter;
(xi) routing the AIO valve deployment device through the portal catheter and into the AV valve annulus region of the heart;
(xii) expanding the expandable member of the AIO valve deployment device, wherein the expandable member and, thereby, prosthetic valve transition from pre-deployment configurations to expanded, post-deployment configurations, whereby the prosthetic valve is disposed adjacent the AV valve annulus region of the subject's heart;
(xiii) guiding the anchor guidewire into and through the gating mechanism of the AIO valve deployment device and the prosthetic valve;
(xiv) positioning the anchor of the anchor guidewire (of the AIO valve deployment device) at a predetermined anchor attachment point between the anterior and posterior papillary muscles of the left ventricle;
(xv) attaching the anchor to the myocardium at the anchor attachment point;
(xvi) retracting the anchor guidewire through the gating mechanism (of the AIO valve deployment device), whereby, the anchor guidewire is severed at a predetermined serving point by the gating mechanism;
(xvii) withdrawing the AIO valve deployment device and severed end of the anchor guidewire through the portal catheter and out of the subject's body; and
(xviii) withdrawing the portal catheter out of the left atrium of the subject's heart and out of the subject's body.

In some embodiments of the invention, wherein the prosthetic "ribbon structure" valve comprises a closed distal end with ribbon members extending toward the proximal end of the valve and a guide ring, prior to the step of positioning the prosthetic valve on the AIO valve deployment device, the proximal ends of the valve are secured to the guide ring.

In some embodiments, the guide ring comprises an anchoring mechanism that is designed and configured to position the prosthetic valve proximate a valve annulus (and, hence, cardiovascular tissue associated therewith) and maintain contact therewith for a pre-determined anchor support time period.

In some embodiments of the invention, prior to withdrawing the portal catheter from the left atrium, a suturing device is guided into and through the portal catheter to securely stitch the proximal end of the prosthetic valve to the AV valve annulus region.

In some embodiments of the invention, during the prosthetic valve implant procedures described herein, a rapid heart rate is induced, wherein blood flow to and through the valve to be replace is reduced, more preferably, abated.

In a preferred embodiment of the invention, the prosthetic valve comprises a polymer composition comprising at least one biocompatible polymer.

In some embodiments of the invention, the polymer composition (and, hence, prosthetic valve formed therefrom) further comprises at least one pharmacological agent or composition.

In some embodiments of the invention, the pharmacological agent comprises an antibiotic, such as vancomycin and gentamicin.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIGS. 1A-1D are schematic illustrations of a human heart;

FIG. 1E is an illustration of a normal mitral valve;

FIG. 1F is an illustration of a prolapsed mitral valve;

FIG. 2A is a front plan view of one embodiment of an anchoring mechanism, in accordance with the invention;

FIG. 2B is a perspective view of the anchoring mechanism shown in FIG. 2A, in accordance with the invention;

FIG. 3A is a front plan view of another embodiment of an anchoring mechanism, in accordance with the invention;

FIG. 3B is a perspective view of the anchoring mechanism shown in FIG. 3A, in accordance with the invention;

FIG. 4A is a side view of the anchoring mechanism shown in FIG. 3A, illustrating a pre-deployment configuration, in accordance with the invention;

FIG. 4B is a further perspective view of the anchoring mechanism shown in FIG. 3A, illustrating the pre-deployment configuration shown in FIG. 4A, in accordance with the invention;

FIG. 16A is an illustration of one embodiment of a valve insertion device, in accordance with the invention;

FIG. 16B is a partial front plan view of the valve insertion device shown in FIG. 16A having a prosthetic tissue device engaged thereto, in accordance with the invention;

FIG. 35 is an illustration of one embodiment of an all-in-one (AIO) valve deployment device, in accordance with the invention;

FIG. 36 is a partial front plan view of the AIO valve deployment device shown in FIG. 35 having a prosthetic valve engaged thereto, in accordance with the invention;

FIGS. 40 and 41 are partial front plan, partial sectional views of the AIO valve deployment device shown in FIG. 35, in accordance with the invention.

DETAILED DESCRIPTION OF THE PREFERRED EMBODIMENT

Figure 1A:
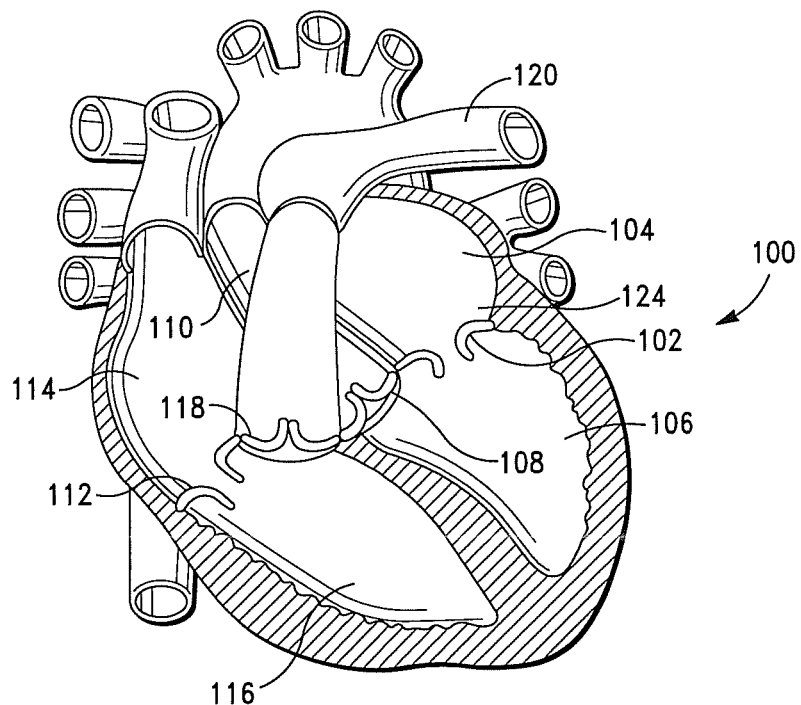
Figure 1B:
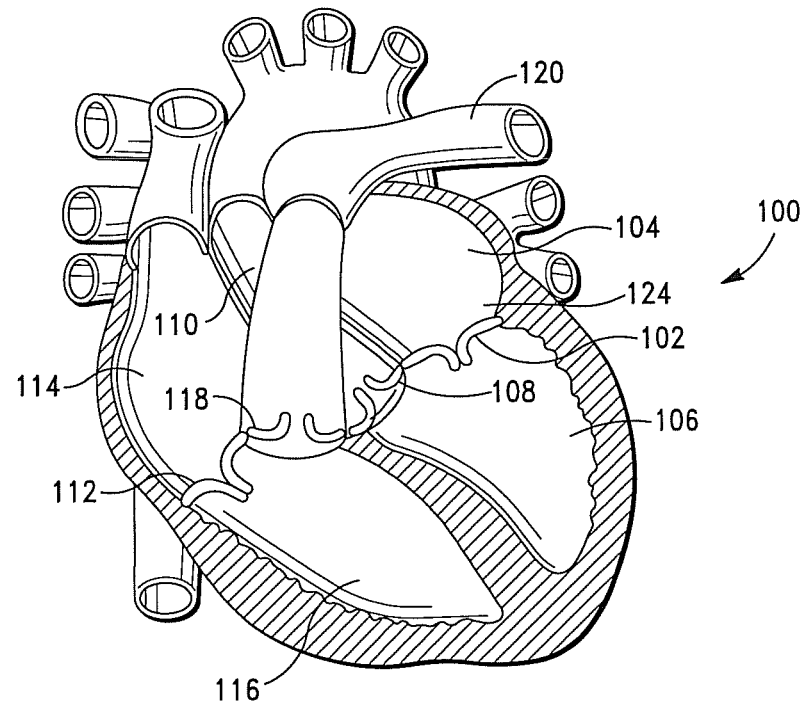
Figure 1C:
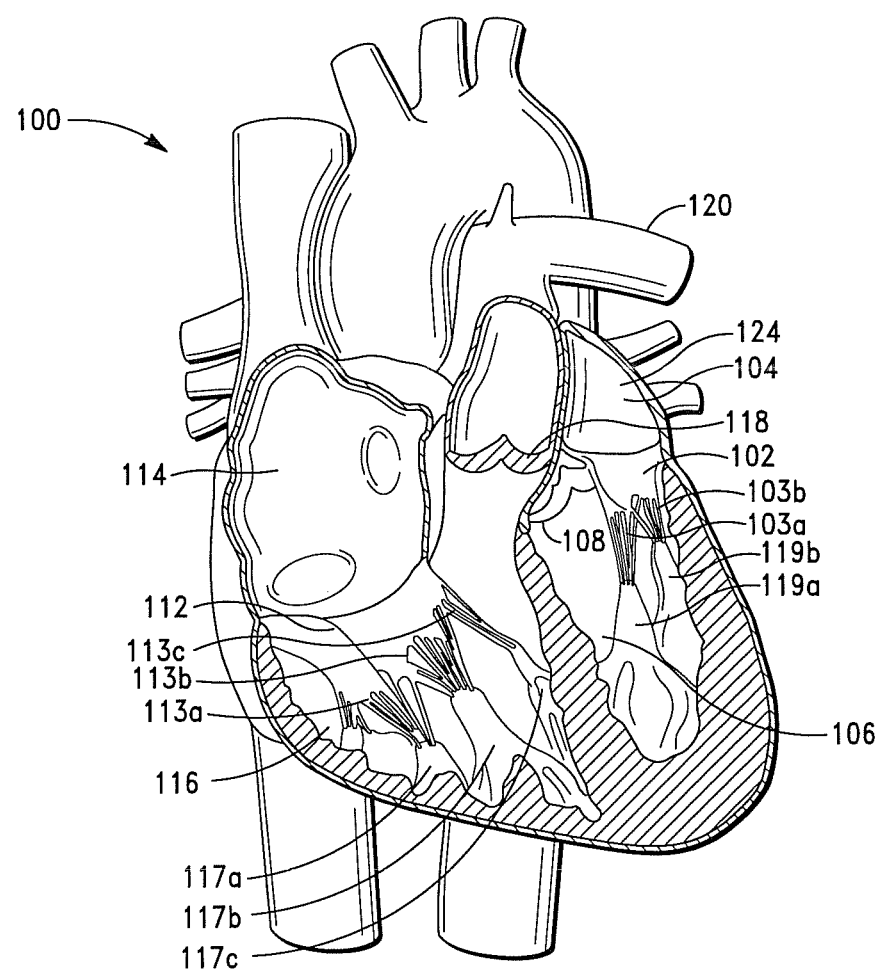

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "extracellular matrix", "ECM", and "ECM material" are used interchangeably herein, and mean and include a collagen-rich substance that is found in between cells in mammalian tissue, and any material processed therefrom, e.g., decellularized extracellular matrix (ECM).

According to the invention, ECM can be derived from a variety of mammalian tissue sources and tissue derived therefrom, including, without limitation, small intestine submucosa (SIS), urinary bladder submucosa (UBS), stomach submucosa (SS), central nervous system tissue, epithelium of mesodermal origin, i.e. mesothelial tissue, dermal tissue, subcutaneous tissue, gastrointestinal tissue, tissue surrounding growing bone, placental tissue, omentum tissue, cardiac tissue, kidney tissue, pancreas tissue, lung tissue, and combinations thereof. The ECM material can also comprise collagen from mammalian sources.

The term "acellular ECM", as used herein, means and includes ECM that has a reduced content of cells, i.e. decellularized ECM.

The terms "urinary bladder submucosa (UBS)", "small intestine submucosa (SIS)" and "stomach submucosa (SS)" also mean and include any UBS and/or SIS and/or SS tissue that includes the tunica mucosa (which includes the transitional epithelial layer and the tunica propria), submucosal layer, one or more layers of muscularis, and adventitia (a loose connective tissue layer) associated therewith.

ECM can also be derived from basement membrane of mammalian organs/tissue, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

According to the invention, the ECM can be derived from xenogeneic and allogeneic tissue sources.

ECM can also be derived from other sources, including, without limitation, collagen from plant sources and synthesized extracellular matrices, i.e. cell cultures.

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussuceptive angiogenesis, sprouting angiogenesis, therapeutic angiogenesis and vasculogenesis.

The term "adverse inflammatory response", as used herein, means and includes a physiological response that is sufficient to induce constitutive clinically relevant expression of pro-inflammatory cytokines, such as interleukin-1 beta (IL-1β) and monocyte chemoattractant protein-1 (MCP-1) in vivo.

The term "adverse biological response", as used herein, means and includes a physiological response that is sufficient to induce a biological process and/or restrict a phase associated with biological tissue healing in vivo, including without limitation, neovascularization and remodeling of the damaged biological tissue. The term "adverse biological response" thus includes an "adverse inflammatory response", e.g., development of fibrotic tissue.

The terms "polymer composition" and "polymeric compositions" are used interchangeably herein and mean and include a composition comprising at least one polymer, including, without limitation, biodegradable polymers, including, without limitation, polyurethane urea (Artelon®), poly(ε-caprolactone) (PCL), and poly(glycerol sebacate) (PGS), non-biodegradable polymers, including, without limitation, polytetrafluoroethylene (Teflon®), polypropylene and polyethylene terephthalate (Dacron®), and natural polymers.

The term "biologically active agent", as used herein, means and includes agent that induces or modulates a physiological or biological process, or cellular activity, e.g., induces proliferation, and/or growth and/or regeneration of tissue.

The term "biologically active agent" thus means and includes a growth factor, including, without limitation, fibroblast growth factor-2 (FGF-2), transforming growth factor beta (TGF-β), and vascular endothelial growth factor (VEGF).

The term "biologically active agent" also means and includes a cell, including, without limitation, human embryonic stem cells, myofibroblasts, mesenchymal stem cells, and hematopoietic stem cells.

The term "biologically active agent" also means and includes an exosome and/or microsome.

The terms "exosome" and "microsome" as used herein mean and include a lipid bilayer structure that contains or encapsulates a biologically active agent and/or pharmacological agent, including, without limitation, a growth factor, e.g., TGF-β, TGF-α, VEGF and insulin-like growth factor (IGF-I), a cytokine, e.g., interleukin-8 (IL-8), a transcription factor and micro RNA (miRNA).

The term "biologically active agent" also means and includes agents commonly referred to as a "protein", "peptide" and "polypeptide", including, without limitation, collagen (types I-V), proteoglycans and glycosaminoglycans (GAGs).

The terms "pharmacological agent", "active agent" and "drug" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent" and "drug" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPs), enzymes and enzyme inhibitors, anticoagulants and/or anti-thrombotic agents, DNA, RNA, modified DNA and RNA, NSAIDs, inhibitors of DNA, RNA or protein synthesis, polypeptides, oligonucleotides, polynucleotides, nucleoproteins, compounds that modulate cell migration, compounds that modulate proliferation and growth of tissue, and vasodilating agents.

The terms "pharmacological agent", "active agent" and "drug" thus mean and include, without limitation, vancomycin and gentamicin.

The terms "pharmacological agent", "active agent" and "drug" also mean and include Class I-Class V antiarrhythmic agents.

The terms "pharmacological agent", "active agent", "drug" and "active agent formulation" further mean and include, without limitation, the following anti-fibrotics: paclitaxel, sirolimus and derivatives thereof, including everolimus.

The terms "pharmacological agent", "active agent" and "drug" also mean and include a statin, i.e. a HMG-CoA reductase inhibitor, including, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Creston®), and simvastatin (Zocor®, Lipex®).

Additional biologically active and pharmacological agents are set forth in priority U.S. application Ser. No. 15/206,833, now U.S. Pat. No. 10,188,510, which is expressly incorporated herein in its entirety.

The term "therapeutically effective", as used herein, means that the amount of the "pharmacological agent" and/or "biologically active agent" and/or "pharmacological composition" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to methods for replacing diseased or defective AV valves, including, without limitation, pulmonary, mitral and tricuspid valves.

As indicated above and discussed in detail below, in one preferred embodiment of the invention, the method for replacing a diseased or defective AV valve generally comprises the following steps:
(i) providing a prosthetic "ribbon structure" valve having a closed distal end;
(ii) providing a catheter assembly adapted to access the subject's heart, preferably, an AV valve annulus region; the catheter assembly preferably comprising a portal catheter, catheter guide, all-in-one (AIO) valve deployment device, anchor guidewire and anchor;
(iii) preparing a catheter sub-assembly comprising the portal catheter and catheter guide (and guidewire);
(iv) selecting a vein; preferably, the femoral vein, which provides access to an AV valve annulus region;
(v) placing an incision through tissue proximate the vein and through the vein, wherein an opening is provided in the vein;
(vi) inserting the catheter sub-assembly through the incision, into and through the vein and into the right atrium of the subject's heart;
(vii) advancing the catheter sub-assembly into the left atrium of the subject's heart;
(viii) retracting the catheter guide of the catheter sub-assembly through the portal catheter and out of the subject's body;
(ix) positioning the prosthetic valve on the AIO valve deployment device;
(x) inserting the AIO valve deployment device (and anchor guidewire) with the prosthetic valve engaged thereto into the portal catheter;
(xi) routing the AIO valve deployment device through the portal catheter and into the AV valve annulus region of the heart;
(xii) expanding the expandable member of the AIO valve deployment device, wherein the expandable member and, thereby, prosthetic valve transition from pre-deployment configurations to expanded, post-deployment configurations, whereby the prosthetic valve is disposed adjacent the AV valve annulus region of the subject's heart;
(xiii) guiding the anchor guidewire into and through the gating mechanism of the AIO valve deployment device and the prosthetic valve;
(xiv) positioning the anchor of the anchor guidewire (of the AIO valve deployment device) at a predetermined anchor attachment point between the anterior and posterior papillary muscles of the left ventricle;
(xv) attaching the anchor to the myocardium at the anchor attachment point;
(xvi) retracting the anchor guidewire through the gating mechanism (of the AIO valve deployment device), whereby, the anchor guidewire is severed at a predetermined serving point by the gating mechanism;
(xvii) withdrawing the AIO valve deployment device and severed end of the anchor guidewire through the portal catheter and out of the subject's body; and
(xviii) withdrawing the portal catheter out of the left atrium of the subject's heart and out of the subject's body.

In some embodiments of the invention, prior to withdrawing the portal catheter from the left atrium, a suturing device is guided into and through the portal catheter to securely stitch the proximal end of the prosthetic valve to the AV valve annulus region.

As indicated above, in some embodiments of the invention, wherein the prosthetic "ribbon structure" valve comprises a closed distal end with ribbon members extending toward the proximal end of the valve and a guide ring, prior to the step of positioning the prosthetic valve on the AIO valve deployment device, the proximal ends of the valve are secured to the guide ring.

In some embodiments, the guide ring comprises an anchoring mechanism that is designed and configured to position the prosthetic valve proximate a valve annulus (and, hence, cardiovascular tissue associated therewith) and maintain contact therewith for a pre-determined anchor support time period.

In some embodiments of the invention, during the prosthetic valve implant procedures described herein, a rapid heart rate is induced, wherein blood flow to and through the valve to be replace is reduced, more preferably, abated. According to the invention, the rapid heart rate can be induced by various conventional means, such as pharmacological agents, pacing devices, etc.

In some embodiments of the invention, the prosthetic valve comprises an ECM composition comprising acellular ECM derived from mammalian tissue.

In a preferred embodiment of the invention, the mammalian tissue comprises small intestine submucosa (SIS), urinary bladder submucosa (UBS), stomach submucosa (SS), mesothelial tissue, gastrointestinal tissue, tissue surrounding growing bone, placental tissue, omentum tissue, cardiac tissue, kidney tissue, pancreas tissue or lung tissue, and combinations thereof.

In some embodiments of the invention, the ECM composition (and, hence, prosthetic tissue valve formed therefrom) further comprises at least one additional biologically active agent or composition, i.e. an agent that induces or modulates a physiological or biological process, or cellular activity, e.g., induces proliferation, and/or growth and/or regeneration of tissue.

In some embodiments of the invention, the biologically active agent comprises a growth factor, including, without limitation, transforming growth factor beta (TGF-β), fibroblast growth factor-2 (FGF-2), and vascular endothelial growth factor (VEGF).

In some embodiments of the invention, the ECM composition (and, hence, prosthetic tissue valve formed therefrom) further comprises at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include, without limitation, antibiotics, anti-fibrotics, anti-viral agents, analgesics, anti-inflammatories, anti-neoplastics, anti-spasmodics, and anti-coagulants and/or anti-thrombotic agents.

In some embodiments of the invention, the prosthetic valve comprises a polymer composition comprising at least one biocompatible polymer.

As discussed in detail herein, in a preferred embodiment, the prosthetic valves of the invention comprise a conical shaped structural member.

In some embodiments, the structural member comprises a ribbon structure.

In a preferred embodiment of the invention, the ribbon structure comprises a plurality of elongated ribbon members.

In some embodiments of the invention, the structural member comprises a continuous sheet member.

In some embodiments of the invention, the prosthetic valve; preferably, the proximal end thereof, comprises an anchoring mechanism (or ring) that is designed and configured to position the prosthetic valve proximate a valve annulus (and, hence, cardiovascular tissue associated therewith) and maintain contact therewith for a pre-determined anchor support time period.

In some embodiments of the invention, the anchoring mechanism is designed and configured to position and securely engage the prosthetic valve to a valve annulus (and, hence, cardiovascular tissue associated therewith) and maintain contact therewith for a pre-determined anchor support time period.

According to the invention, the anchoring mechanism can comprise various forms and materials, such as disclosed in Applicant's U.S. Pat. No. 9,044,319, which is incorporated by reference herein in its entirety.

As set forth in U.S. Pat. No. 9,044,319, the anchoring mechanism preferably comprises an expandable member.

The anchoring mechanism can also comprise various materials, including biocompatible metals, such as stainless steel and a nickel titanium alloy (e.g., Nitinol®), and various polymeric materials, such as polyesters, poly(amino acids), polyanhydrides, polyorthoesters, polyurethanes, polycarbonates, homopolymers and copolymers of poly(lactic acid) and poly(glycolic acid), copolyesters of e-caprolactone, trimethylene carbonate, and para-dioxanone.

The anchoring mechanism can also comprise various biodegradable materials, such as magnesium and ECM tissue.

Referring now to FIGS. 2A and 2B, there is shown one embodiment of an anchoring mechanism 80, which can be readily employed in the prosthetic valves of the invention.

As illustrated in FIGS. 2A and 2B, the anchoring mechanism 80 includes at least one helically arranged band element 82 forming a tubular configuration; the band element 82 comprising a plurality of uniformly shaped closed, interconnecting cells 84, and a plurality of connector elements extending between and interconnecting longitudinally spaced portions of the band over its tubular length.

According to the invention, the cells 84 can comprise various shapes, such a rectangular shape and a diamond shape, as shown in FIGS. 2A and 2B.

Retelling now to FIGS. 3A, 3B, 4A and 4B, there is shown another embodiment of an anchoring mechanism 86, which can be readily employed in the prosthetic valves of the invention.

As discussed in detail in U.S. Pat. No. 9,044,319 and shown in FIGS. 4A and 4B, to provide a "compressed" pre-deployment configuration and facilitate a transition to a desired post-deployment configuration, the anchoring mechanism 86 preferably comprises a discontinuous band, wherein one end of the anchoring mechanism 90 over-laps the other end of the anchoring mechanism 92.

As indicated above, the anchoring mechanism is configured to position the prosthetic tissue valves proximate a valve annulus and maintain contact therewith for a pre-determined anchor support time period.

In some embodiments of the invention, wherein the prosthetic valve comprises a prosthetic ECM mammalian tissue valve, the anchor support time period is preferably within the process of tissue remodeling or regeneration.

As set forth in Applicant's U.S. Pat. No. 9,044,319, to control and enhance the anchor support time period, in some embodiments, the anchoring mechanism comprises a microneedle anchoring mechanism having plurality of biodegradable microneedles or barbs that are adapted to position and secure the prosthetic tissue valve to a cardiovascular structure and, hence, the cardiovascular tissue thereof and maintain engagement thereto for an enhanced anchor support time period.

As also set forth in Applicant's U.S. Pat. No. 9,044,319, the microneedle anchoring mechanism and, hence, microneedles thereof can comprise a biodegradable polymeric material, an ECM material or a pharmacological agent or composition (i.e. drug), e.g., Heparin®, Plavix®, etc., or a combination thereof.

The microneedle anchoring mechanism and, hence, microneedles thereof can also comprise a biocompatible and bioabsorbable metal, such as magnesium.

Referring now to FIGS. 5, 6, 7A and 7B, there is shown one embodiment of a microneedle anchoring mechanism 200, which can similarly be employed in the prosthetic valves of the invention.

Figure 5:
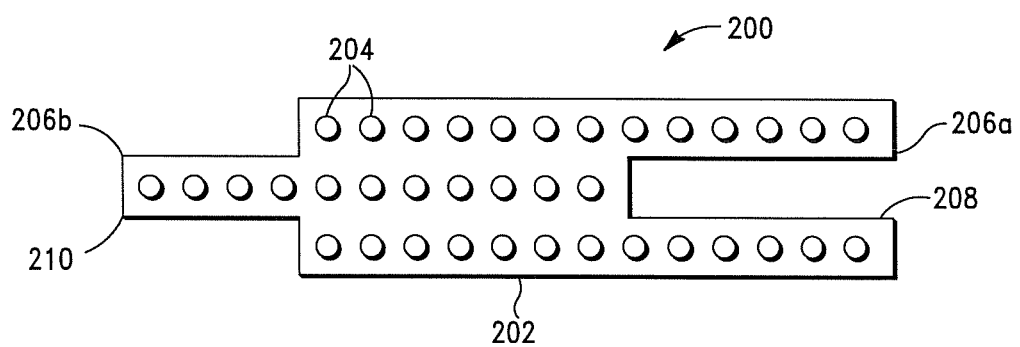
FIG. 5 is a top plan view of another embodiment of an anchoring mechanism, in accordance with the invention.
Figure 6:
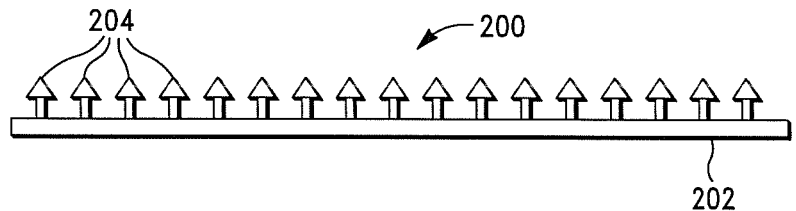
FIG. 6 is a front plan view of the anchoring mechanism shown in FIG. 5, in accordance with the invention.

As illustrated in FIGS. 5 and 6, the microneedle anchoring mechanism 200 includes a base 202 and a plurality of microneedles 204, which are designed and configured to pierce through and project out of a prosthetic valve and into cardiovascular tissue when a prosthetic valve employing same is deployed proximate a cardiovascular structure.

Figures 7A, 7B:
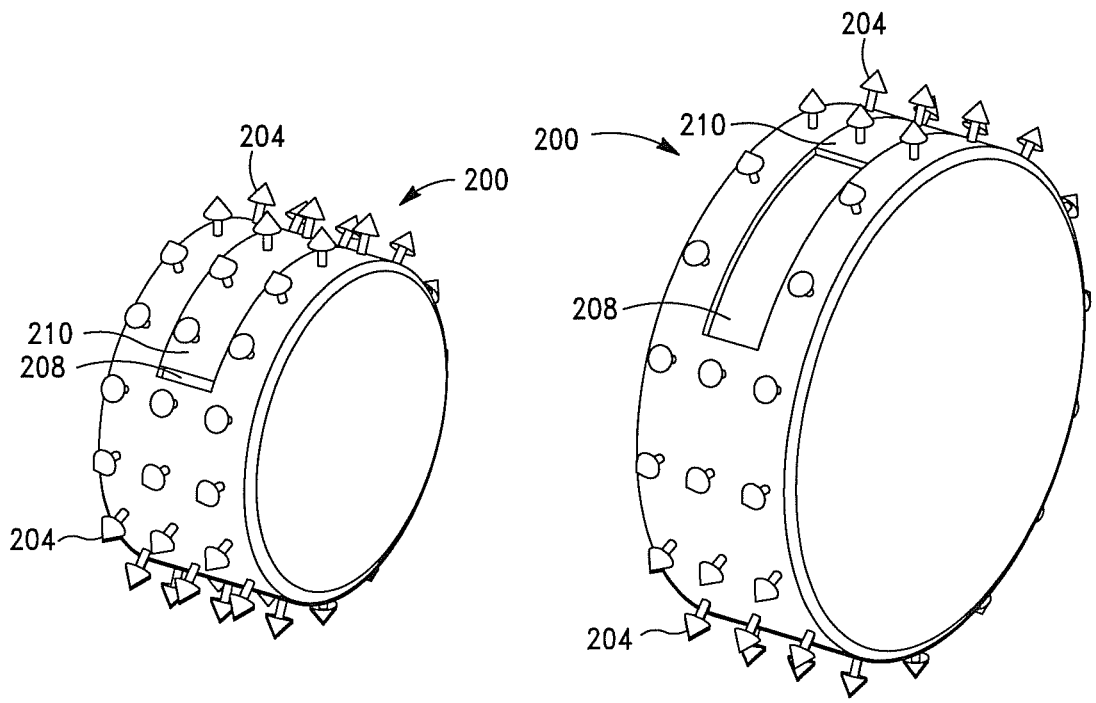
FIG. 7A is a perspective view of the anchoring mechanism shown in FIGS. 5 and 6, illustrating a pre-deployment configuration, in accordance with the invention.
FIG. 7B is a perspective view of the anchoring mechanism shown in FIGS. 5 and 6, illustrating a post-deployment configuration, in accordance with the invention.

As also illustrated in FIG. 5, to facilitate positioning the microneedle anchoring mechanism 200 in a pre-deployment configuration, as shown in FIG. 7A, to a post-deployment configuration, as shown in FIG. 7B, one end 206a of the microneedle anchoring mechanism base 202 preferably includes an elongated slot 208 that is designed and configured to receive the base projection 210 on the opposing end 206b of the base 202.

As illustrated in FIGS. 7A and 7B, when the microneedle anchoring mechanism 200 is in a pre-deployment configuration, the elongated slot 208 slidably receives the base projection 210 therein. When the microneedle anchoring mechanism 200 transitions to a post-deployment configuration, as shown in FIG. 7B, the base projection 210 transitions (or moves) within the elongated slot 208, wherein a larger diameter post-deployment configuration is provided.

As set forth in priority Co-pending U.S. application Ser. No. 16/129,968 (hereinafter "the '968 application") and U.S. application Ser. No. 15/206,833, now U.S. Pat. No. 10,188,510, which are expressly incorporated herein in their entirety, in some embodiments of the invention, the distal end of the prosthetic valve comprises a structural ring.

As also set forth in the '968 application, the annular ring and/or structural ring can comprise various biocompatible materials and compositions formed therefrom.

As indicated above, in some embodiments of the invention, the prosthetic valve comprises an ECM composition comprising acellular ECM derived from a mammalian tissue source, i.e. mammalian ECM.

According to the invention, the ECM can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427; which are incorporated by reference herein in their entirety.

As indicated above, suitable mammalian tissue sources include, without limitation, the small intestine, large intestine, stomach, lung, liver, kidney, pancreas, peritoneum, placenta, heart, bladder, prostate, tissue surrounding growing enamel, tissue surrounding growing bone, and any fetal tissue from any mammalian organ.

The mammalian tissue can thus comprise, without limitation, small intestine submucosa (SIS), urinary bladder submucosa (UBS), stomach submucosa (SS), central nervous system tissue, epithelium of mesodermal origin, i.e. mesothelial tissue, dermal tissue, subcutaneous tissue, gastrointestinal tissue, placental tissue, omentum tissue, cardiac tissue, kidney tissue, pancreas tissue, lung tissue, and combinations thereof. The ECM can also comprise collagen from mammalian sources.

In some embodiments, the mammalian tissue source comprises an adolescent mammalian tissue source, e.g., tissue derived from a porcine mammal less than 3 years of age.

According to the invention, the ECM can also be derived from the same or different mammalian tissue sources, as disclosed in Co-Pending application Ser. Nos. 13/033,053 and 13/033,102; which are incorporated by reference herein.

In a preferred embodiment of the invention, the ECM comprises sterilized and decellularized (or acellular) ECM.

According to the invention, the ECM can be sterilized and decellularized by various conventional means.

In some embodiments of the invention, the ECM is sterilized and decellularized via applicant's proprietary process disclosed in U.S. application Ser. No. 13/480,205; which is expressly incorporated by reference herein in its entirety.

As also indicated above, in some embodiments of the invention, the ECM composition (and, hence, prosthetic tissue valve formed therefrom) further comprises at least one additional biologically active agent or composition, i.e. an agent that induces or modulates a physiological or biological process, or cellular activity, e.g., induces proliferation, and/or growth and/or regeneration of tissue.

According to the invention, suitable biologically active agents include any of the aforementioned biologically active agents, including, without limitation, the aforementioned growth factors, cells and proteins.

Thus, in some embodiments of the invention, the biologically active agent comprises a growth factor, including, without limitation, transforming growth factor beta (TGF-β), fibroblast growth factor-2 (FGF-2), and vascular endothelial growth factor (VEGF).

In some embodiments of the invention, the biologically active agent comprises an exosome (referred to hereinafter as an "exosome augmented ECM composition").

As discussed in detail in Applicant's U.S. application Ser. No. 15/386,640, now U.S. Pat. No. 10,143,778, which is also incorporated by reference herein, exosomes significantly enhance the delivery of biologically active agents to cells through two seminal properties/capabilities.

The first property comprises the capacity of exosomes to shield the encapsulated biologically active agents (via the exosome lipid bilayer) from proteolytic agents, which can, and often will, degrade unshielded (or free) bioactive molecules and render the molecules non-functional in biological tissue environments.

The second property of exosomes comprises the capacity to directly and, hence, more efficiently deliver biologically active agents to endogenous cells in the biological tissue. As is well known in the art, endogenous cells typically do not comprise the capacity to "directly" interact with "free" biologically active agents, such as growth factors. There must be additional biological processes initiated by the endogenous cells to interact directly with biologically active agents, e.g., expression of receptor proteins for or corresponding to the biologically active agents.

As also set forth in U.S. application Ser. No. 15/386,640, exosomes facilitate direct interaction by and between endogenous cells and exosome encapsulated biologically active agents (and, hence, direct delivery of bioactive molecules to endogenous cells), which enhances the bioactivity of the agents.

Thus, it is contemplated that, following placement of a prosthetic tissue valve comprising an exosome augmented ECM composition on or in a cardiovascular structure (or structures) of a subject, e.g., valve annulus, and, hence, damaged cardiovascular tissue associated therewith, the prosthetic ECM tissue valve will induce a multitude of significant biological processes in vivo, including significantly enhanced inflammation modulation of the cardiovascular tissue, and significantly induced neovascularization, stem cell proliferation, remodeling of the cardiovascular tissue, and regeneration of new tissue and tissue structures.

By way of example, when an exosome augmented ECM composition comprising encapsulated IL-8 (and, hence, tissue valve formed therefrom) is disposed proximate damaged cardiovascular tissue, the exosome augmented ECM composition and, hence, tissue valve formed therefrom modulates the transition of M1 type "acute inflammatory" macrophages to M2 type "wound healing" macrophages initiated by the acellular ECM.

By way of further example, when an exosome augmented ECM composition comprising encapsulated miRNAs (and, hence, tissue valve formed therefrom) is disposed proximate damaged cardiovascular tissue, the exosome augmented ECM composition and, hence, tissue valve formed therefrom induce enhanced stem cell proliferation via the delivery of exosome encapsulated miRNAs and transcription factors to the damaged cardiovascular tissue, which signals the endogenous stem cells to bind and/or attach to the acellular ECM and proliferate.

According to the invention, the exosomes can be processed and derived from a mammalian fluid composition, including, without limitation, blood, amniotic fluid, lymphatic fluid, interstitial fluid, pleural fluid, peritoneal fluid, pericardial fluid and cerebrospinal fluid.

The exosomes can also be derived and, hence, processed from in vitro or in vivo cultured cells, including, without limitation, one of the aforementioned cells, e.g., mesenchymal stem cells and hematopoietic stem cells.

The exosomes can also comprise semi-synthetically generated exosomes that are derived from an exosome producing cell line.

As also indicated above, in some embodiments of the invention, the ECM composition (and, hence, prosthetic tissue valve formed therefrom) further comprises at least one pharmacological agent or composition (or drug), i.e. an agent or composition that is capable of producing a desired biological effect in vivo, e.g., stimulation or suppression of apoptosis, stimulation or suppression of an immune response, etc.

According to the invention, suitable pharmacological agents and compositions include any of the aforementioned pharmacological agents and agents set forth in Applicant's U.S. application Ser. No. 15/206,833, now U.S. Pat. No. 10,188,510.

It is thus contemplated that, in some embodiments of the invention, following placement of a prosthetic tissue valve comprising an ECM composition of the invention on or in a cardiovascular structure (or structures) of a subject, e.g., valve annulus, and, hence, damaged cardiovascular tissue associated therewith, the prosthetic ECM tissue valve will become populated with cells from the subject that will gradually remodel the ECM into cardiovascular tissue and tissue (and, hence, valve) structures.

It is further contemplated that, following placement of a prosthetic tissue valve comprising an ECM composition of the invention on or in a cardiovascular structure (or structures) of a subject, and, hence, damaged cardiovascular tissue associated therewith, stem cells will migrate to the prosthetic ECM tissue valve from the point(s) at which the valve is attached to the cardiovascular structure or structures.

It is still further contemplated that, during circulation of epithelial and endothelial progenitor cells after placement of a prosthetic ECM tissue valve on a cardiovascular structure (or structures), the surfaces of an ECM tissue valve will rapidly become lined or covered with epithelial and/or endothelial progenitor cells.

As discussed in detail below, it is still further contemplated that, in some embodiments of the invention, following placement of a prosthetic ECM tissue valve of the invention on or in a cardiovascular structure (or structures) in a subject and, hence, cardiovascular tissue associated therewith, the prosthetic ECM tissue valve will induce "modulated healing" of the cardiovascular structure(s) and cardiovascular tissue associated therewith.

It is still further contemplated that the points at which an ECM tissue valve is attached to a cardiovascular structure (or structures) in a subject will serve as points of constraint that direct the remodeling of the ECM into cardiovascular tissue and valve structures that are identical or substantially identical to properly functioning native cardiovascular tissue and valve structures.

As indicated above, in some embodiments of the invention, the prosthetic valve comprises a polymeric composition comprising a polymeric material; more preferably, a biocompatible polymeric material.

In some embodiments, the polymeric material comprises a biodegradable polymeric material. Suitable biodegradable polymeric materials are set forth in Applicant's Co-Pending U.S. application Ser. Nos. 16/129,968 and 16/418,068, and U.S. Pat. Nos. 9,149,496 and 9,694,104, which are incorporated by reference herein.

According to the invention, suitable polymeric materials, include, without limitation, polyurethane urea (Artelon®), polypropylene, poly(ε-caprolactone) (PCL), poly(glycerol sebacate) (PGS), polyglycolide (PGA), polylactide (PLA), poly dioxanone (a polyether-ester), poly lactide-co-glycolide, polyamide esters, polyalkalene esters, polyvinyl esters, polyvinyl alcohol, and polyanhydrides and polyethylene terephthalate (Dacron®).

In some embodiments, the polymeric composition comprises at least one of the aforementioned biologically active agents and/or pharmacological agents.

In some embodiments of the invention, the anchoring mechanism and/or structural ring similarly comprises a polymeric composition comprising a polymeric material.

As indicated above, in some embodiments of the invention, it is contemplated that, following placement of a prosthetic valve; particularly, a prosthetic ECM tissue valve of the invention on or in a cardiovascular structure (or structures) in a subject and, hence, cardiovascular tissue associated therewith, the prosthetic ECM tissue valve will induce "modulated healing" of the cardiovascular structure (s) and cardiovascular tissue associated therewith.

The term "modulated healing", as used herein, and variants of this language generally refer to the modulation (e.g., alteration, delay, retardation, reduction, etc.) of a process involving different cascades or sequences of naturally occurring tissue repair in response to localized tissue damage or injury, substantially reducing their inflammatory effect. Modulated healing, as used herein, includes many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other.

For example, in some embodiments of the invention, the prosthetic ECM tissue valve is specifically formulated (or designed) to alter, delay, retard, reduce, and/or detain one or more of the phases associated with healing of damaged tissue, including, but not limited to, the inflammatory phase (e.g., platelet or fibrin deposition), and the proliferative phase when in contact with biological tissue.

In some embodiments, "modulated healing" means and includes the ability of the prosthetic ECM tissue valve to restrict the expression of inflammatory components. By way of example, according to the invention, when a prosthetic tissue valve (and/or annular ring and/or structural ring) of the invention comprises a statin augmented ECM composition, i.e. a composition comprising ECM and a statin, and the prosthetic ECM tissue valve is positioned proximate damaged biological tissue, e.g., attached to a valve annulus, the ECM tissue valve restricts expression of monocyte chemoattractant protein-1 (MCP-1) and chemokine (C—C) motif ligand 2 (CCR2).

In some embodiments of the invention, "modulated healing" means and includes the ability of the prosthetic ECM tissue valve to alter a substantial inflammatory phase (e.g., platelet or fibrin deposition) at the beginning of the tissue healing process. As used herein, the phrase "alter a substantial inflammatory phase" refers to the ability of a prosthetic tissue valve of the invention to substantially reduce the inflammatory response at a damaged tissue site, e.g., valve annulus, when in contact with tissue at the site.

In such an instance, a minor amount of inflammation may ensue in response to tissue injury, but this level of inflammation response, e.g., platelet and/or fibrin deposition, is substantially reduced when compared to inflammation that takes place in the absence of a prosthetic ECM tissue valve of the invention.

The term "modulated healing" also refers to the ability of the prosthetic ECM tissue valve to induce host cell and tissue proliferation, bioremodeling, including neovascularization, e.g., vasculogenesis, angiogenesis, and intussusception, and regeneration of new tissue and tissue structures with site-specific structural and functional properties, when disposed proximate damaged tissue, e.g. valve annulus.

Thus, in some embodiments of the invention, the term "modulated healing" means and includes the ability of the prosthetic ECM tissue valve to modulate inflammation and induce host cell and tissue proliferation and remodeling, and regeneration of new tissue when disposed proximate damaged tissue.

It is further contemplated that, during a cardiac cycle after placement of the prosthetic ECM tissue valve on a valve structure, such as a valve annulus region, or structures, wherein the ECM tissue valve is subjected to physical stimuli, adaptive regeneration of the prosthetic ECM tissue valve is also induced.

By the term "adaptive regeneration," it is meant to mean the process of inducing modulated healing of damaged tissue concomitantly with stress-induced hypertrophy of the prosthetic ECM tissue valve, wherein the ECM tissue valve adaptively remodels and forms functioning valve structures that are substantially identical to native valve structures.

As indicated above, it is further contemplated that the points at which the prosthetic ECM tissue valve is attached to a cardiovascular structure (or structures) in a subject will serve as points of constraint that direct remodeling of the ECM into cardiovascular tissue and valve structures that are substantially identical to properly functioning native cardiovascular tissue and valve structures.

Figure 8A:
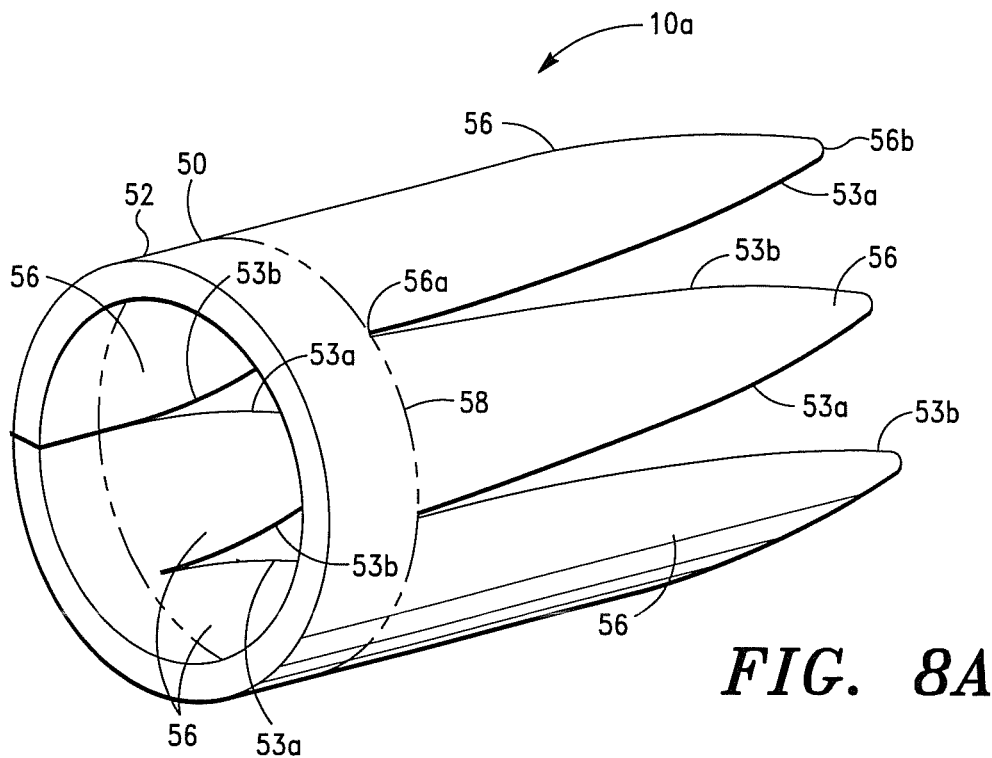
FIG. 8A is a perspective view of one embodiment of one prosthetic "ribbon structure" valve, in accordance with the invention.
Figure 8B:
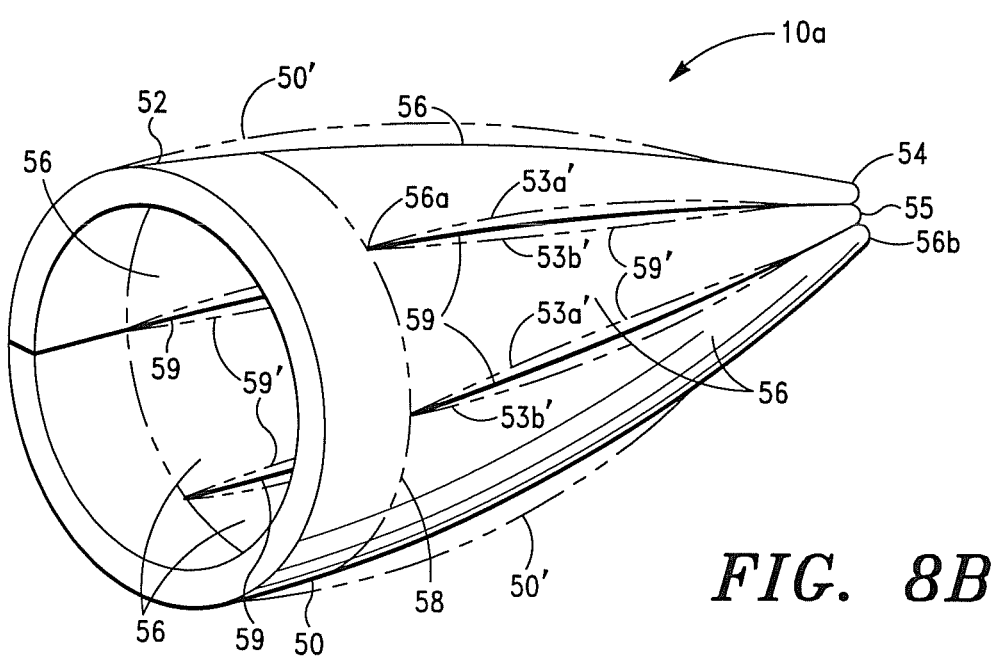
FIG. 8B is a perspective view of the prosthetic valve shown in FIG. 8A in an operational configuration, in accordance with the invention.

Referring now to FIGS. 8A and 8B, there is shown one embodiment of a prosthetic "ribbon structure" valve, where FIG. 8A illustrates the prosthetic valve, denoted 10a, in a pre-deployment configuration and FIG. 8B illustrates the prosthetic valve 10a in a deployed operational configuration.

As set forth in Co-pending U.S. application Ser. No. 16/129,968 and shown in FIGS. 8A and 8B, the prosthetic valve 10a preferably comprises a base member 50 comprising an open proximal valve annulus engagement end 52 having a circumferential ribbon connection region 58, and a distal end 54. The base member 50 further comprises a plurality of ribbon members or ribbons 56 that are connected to and extend from the ribbon connection region 58.

As further illustrated in FIGS. 8A and 8B, each of the plurality of ribbons 56 comprise proximal and distal ends 56a, 56b, and first and second edge regions 53a, 53b that extend from the circumferential ribbon connection region 58 to the distal ends 56b of each of the ribbons 56 and, hence, distal end 54 of the base member 50.

As further illustrated in FIG. 8B, the ribbons 56 of the formed valve 10a also preferably taper to a substantially coincident point 55, wherein the base member 50 has a substantially conical shape. The distal ends 56b of the ribbons 56 are also preferably in a constrained or joined relationship, wherein fluid flow through the joined distal ends 56b of the ribbons 56 is restricted.

As also illustrated in FIG. 8B, the proximal ends 56a of ribbons 56 are positioned circumferentially about the circumferential ribbon connection region 58 of the base member 50, wherein the first edge regions 53a and the second edge regions 53b of the ribbons 56 are positioned adjacent each other and form a plurality of fluid flow modulating regions 59.

As also set forth in Co-pending U.S. application Ser. No. 16/129,968 and shown in FIG. 8B, the base member 50 is configured to expand during positive fluid flow through the base member 50, as shown in phantom and denoted 50', and contract during negative fluid flow through the base member 50, e.g., regurgitating blood flow, and the fluid flow modulating regions 59 are configured to open during expansion of the base member 50' (as shown in phantom and denoted 59'), i.e. the first and second edge regions 53a, 53b separate, as shown in phantom and denoted 53a', 53b', wherein the positive fluid flow is allowed to be transmitted through the fluid flow modulating regions 59', and close during the contraction of the base member 50, wherein the negative fluid flow through base member 50 is restricted, more preferably, abated.

As indicated above, in some embodiments, the prosthetic valves further comprise a structural ring.

Figure 8C:
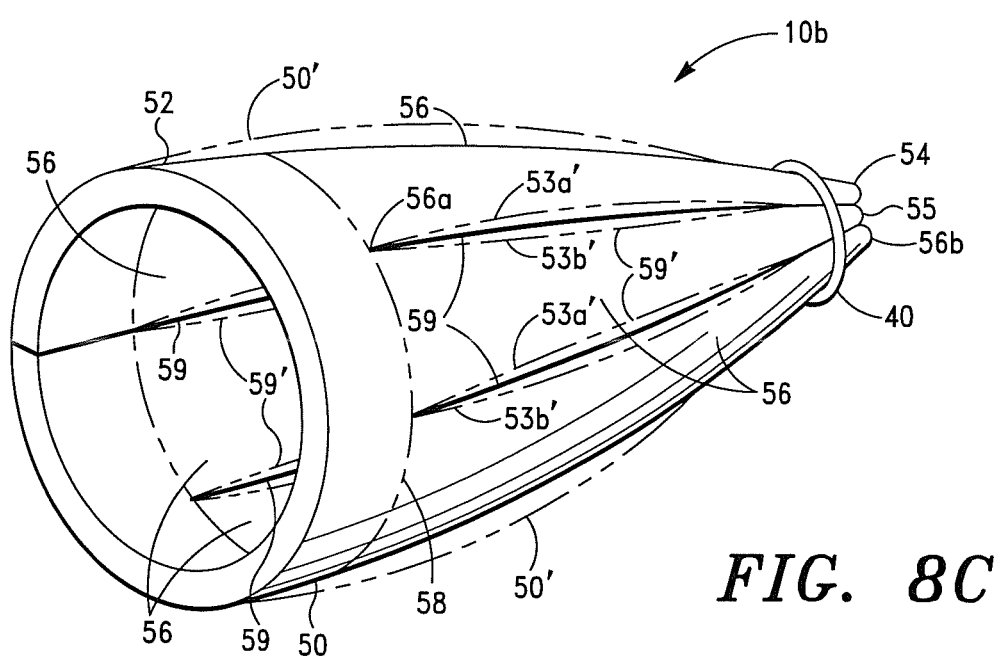
FIG. 8C is a perspective, partial sectional view of another embodiment of the prosthetic valve shown in FIG. 8B having a structural ring disposed at the distal end of the valve, in accordance with the invention.

Referring now to FIG. 8C, there is shown an alternative embodiment of the prosthetic valve 10a, wherein the prosthetic valve, now denoted 10b, includes a structural ring 40 that is disposed on the distal end 54 of the valve 10b.

Figure 9A:
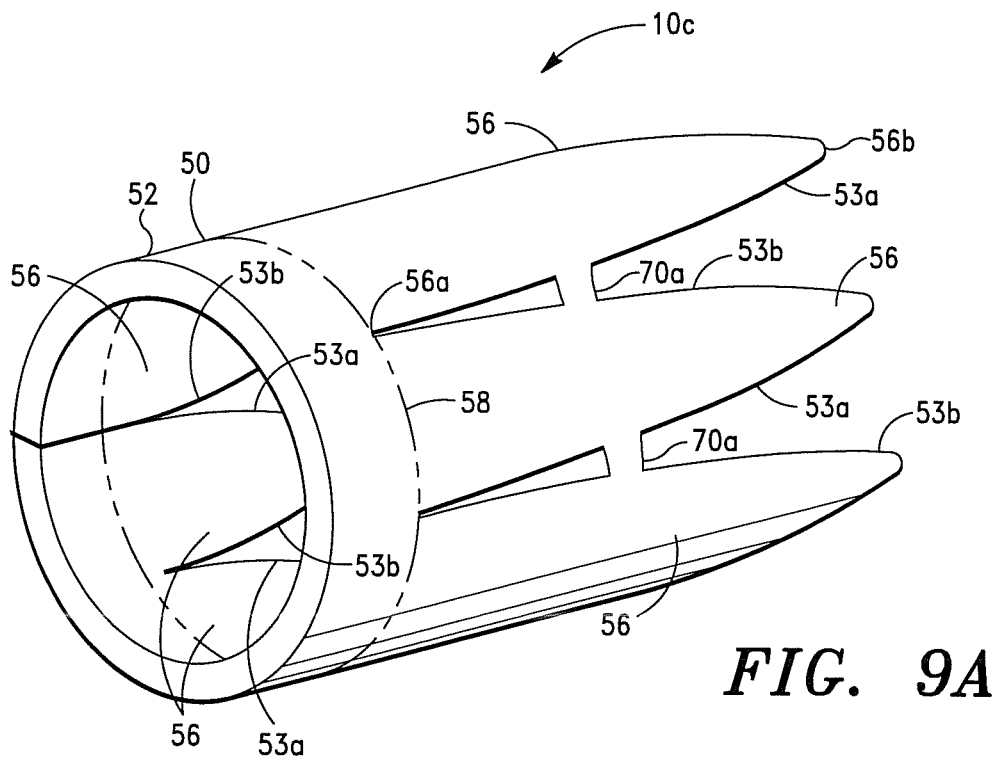
FIG. 9A is a perspective view of another embodiment of a prosthetic "ribbon structure" valve having an integral ribbon coupling member, in accordance with the invention.
Figure 9B:
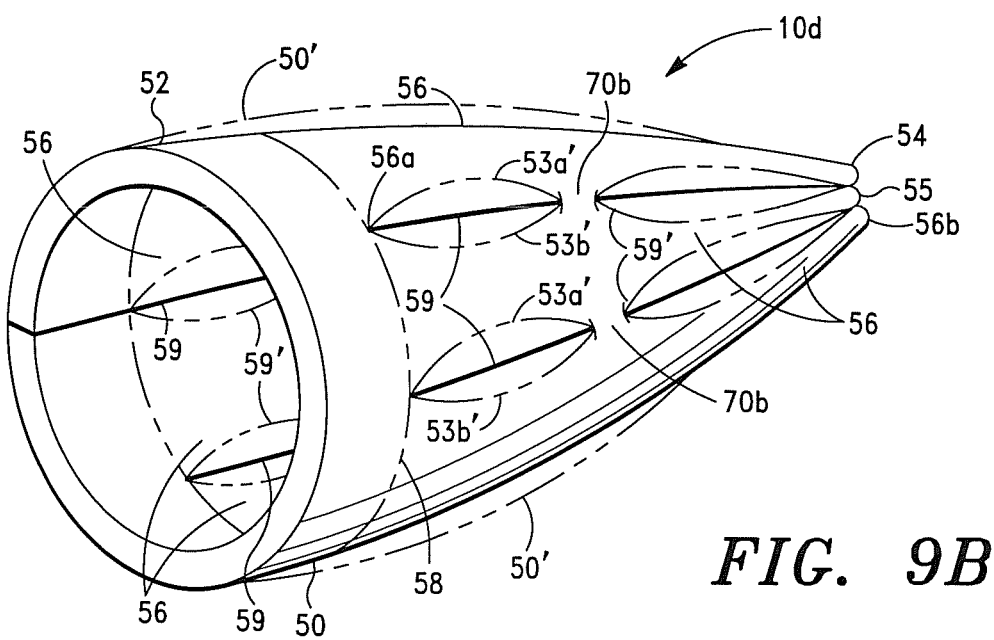
FIG. 9B is a perspective view of the prosthetic valve shown in FIG. 9A in an operational configuration, in accordance with the invention.

Referring now to FIGS. 9A and 9B there is shown another embodiment of a prosthetic "ribbon structure" valve (denoted "10c" and "10d"). As also set forth in the '968 application and shown in FIGS. 9A and 9B, the valves 10c, 10d also comprise a base member 50 comprising a proximal valve annulus engagement end 52 having a circumferential ribbon connection region 58, and a distal end 54. The base member 50 further comprises a plurality of ribbon members or ribbons 56 that are connected to and extend from the ribbon connection region 58.

As further illustrated in FIGS. 9A and 9B, the valves 10c, 10d also preferably comprise at least one constraining band or coupling member (denoted "70a" in FIG. 9A and "70b" in FIG. 9B), more preferably, a plurality of coupling members, which are sized and configured to couple (or join) adjacent ribbons 56, i.e. couple first edge regions 53a to the second edge regions 53b of the ribbon 56.

Figure 9C:
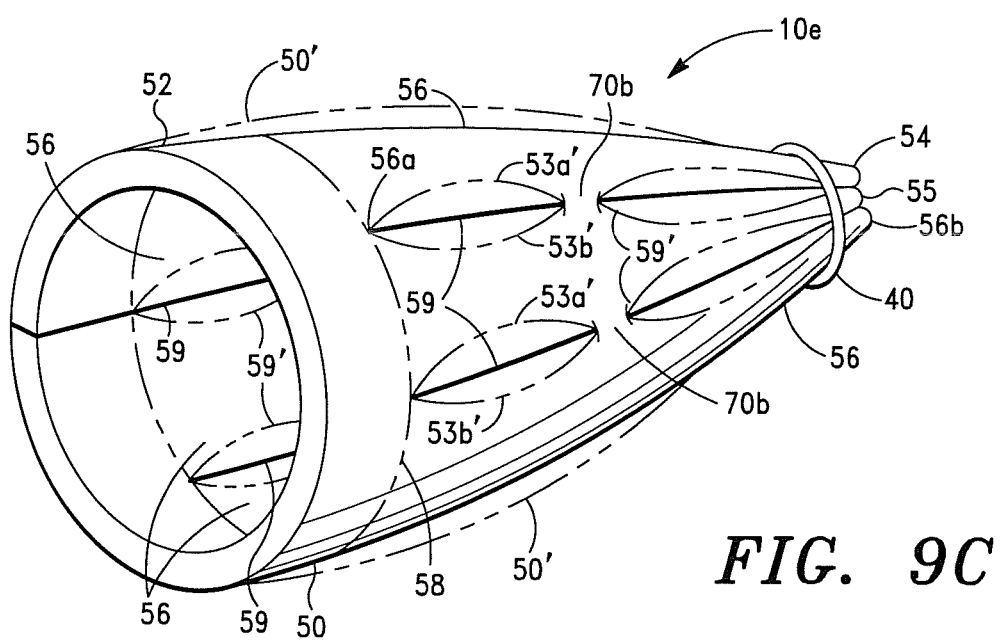
FIG. 9C is a perspective view of another embodiment the prosthetic valve shown in FIG. 9B having a support ring disposed at the distal end of the valve, in accordance with the invention.

Referring now to FIG. 9C, there is shown another embodiment of the prosthetic valve 10d that is shown in FIG. 9B. As illustrated in FIG. 9C, the prosthetic valve, now denoted 10e, similarly comprises a structural ring 40 that is disposed on the distal end 54 of the valve 10e.

Referring now to FIGS. 10A-10E there is shown another embodiment of a prosthetic "ribbon structure" valve.

Figure 10A:
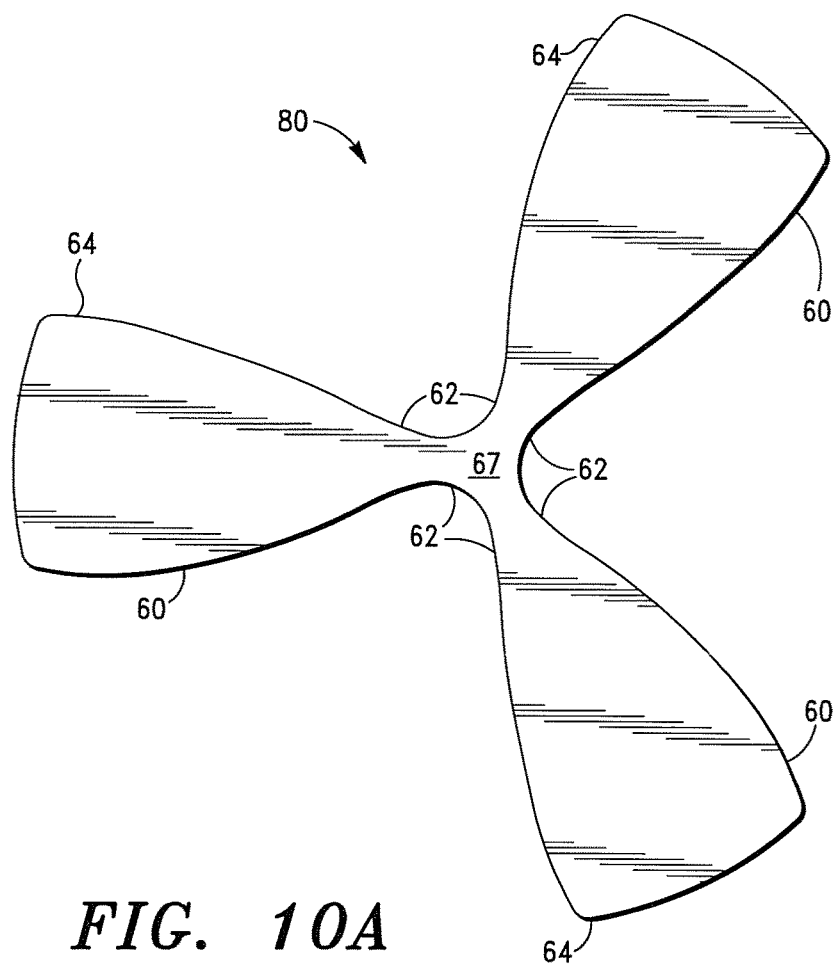
FIG. 10A is a top plan view of another embodiment of a prosthetic "ribbon structure" valve in a pre-formed sheet structure, in accordance with the invention.
Figure 10B:
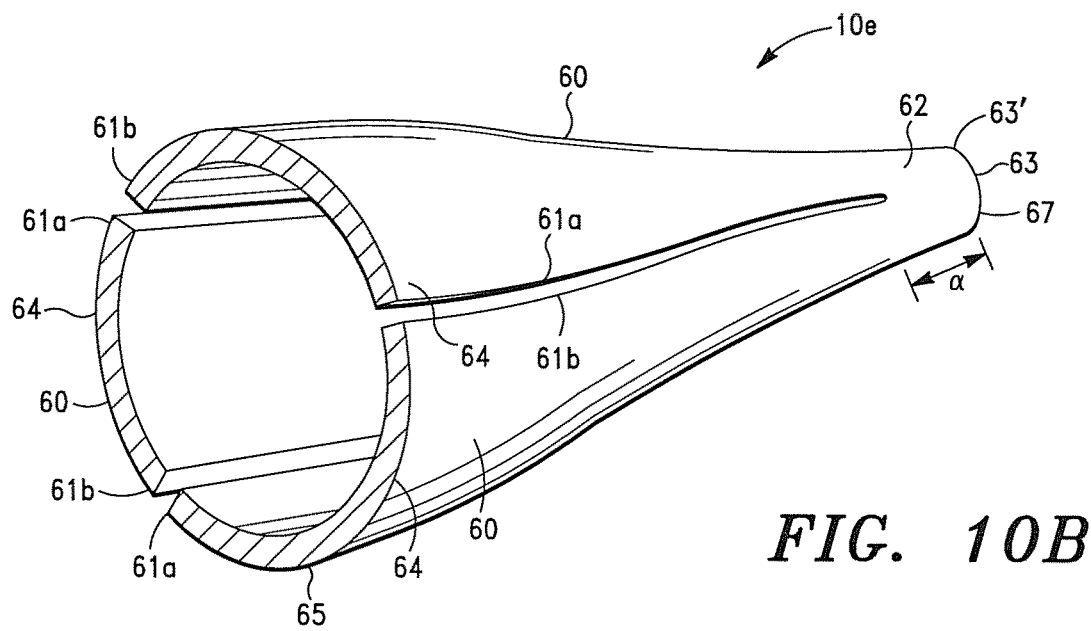
FIG. 10B is a perspective view of the prosthetic valve shown in FIG. 10A in a further pre-formed sheet structure, in accordance with the invention.
Figure 10C:
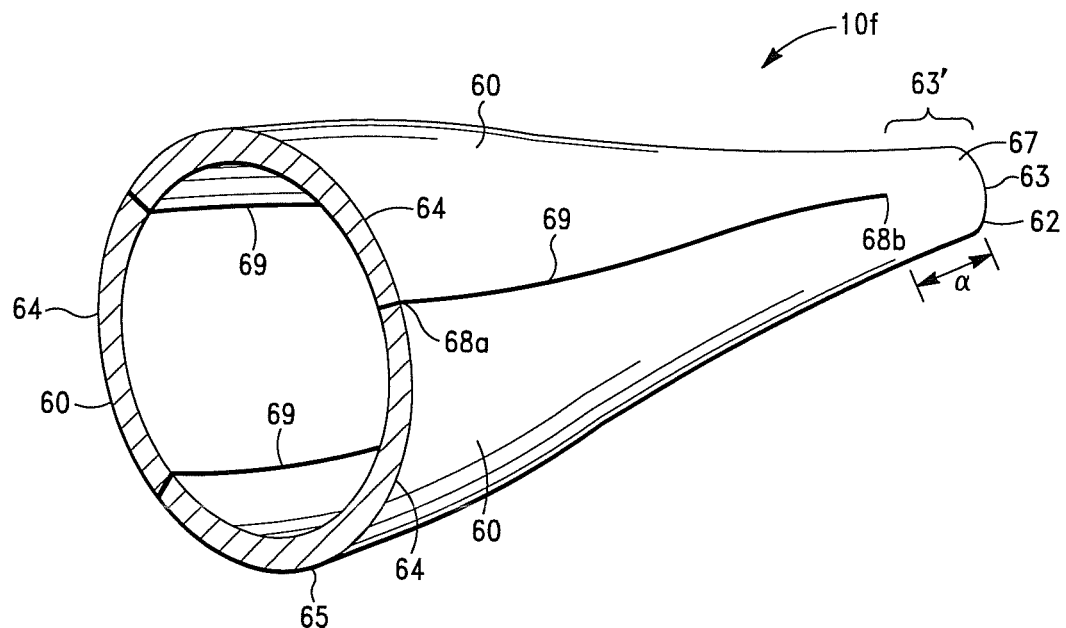
FIG. 10C is a perspective view of the prosthetic valve shown in FIG. 10A in an operational configuration, in accordance with the invention.

As illustrated in FIG. 10C, the prosthetic valve 10f similarly comprises a plurality of elongated ribbon members 60 having proximal and distal ends 64, 62.

As set forth in Co-Pending U.S. application Ser. No. 16/440,504, which is incorporated by reference herein, a seminal feature of prosthetic valve 10f (and, hence, valves 10g-10k, discussed below) is that the valve 10f is formed from and, hence, comprises a seamless pre-formed (or pre-cut) sheet structure or member.

According to the invention, the prosthetic valve 10f (and, hence, valves 10g-10k) can be formed from a single sheet member or multiple sheet members.

Referring now to FIG. 10A, there is shown one embodiment of a pre-formed sheet member 80 that can be formed into a seamless ribbon structure prosthetic valve of the invention, such as prosthetic valve 10f.

As illustrated in FIG. 10A, the sheet member 80 comprises a central region 67 and a plurality of elongated ribbon members 60, which extend from the central region 67.

According to the invention, the ribbon members 60 can similarly comprise any length and shape. The ribbon members 60 can also comprise various widths proximate the proximal end 64.

Referring now to FIGS. 10B and 10C, prosthetic valve 10f is formed by folding each of the elongated ribbon members 60 inwardly to form pre-formed valve structure 10e, shown in FIG. 10B, wherein the central region 67 of the sheet member 80 is disposed at the distal end 63 of prosthetic valve 10f and forms a closed distal valve region 63' that restricts fluid flow therethrough, and the first edge regions 61a and the second edge regions 61b of the ribbon members 60 are positioned adjacent each other and, as illustrated in FIG. 10C, in the fully formed prosthetic valve 10f, form a plurality of fluid flow modulating regions 69 having proximal and distal ends 68a, 68b. When the elongated ribbon members 60 are folded inwardly, an internal region (denoted "60'") is also formed in the prosthetic valve 10f.

As set forth in Co-Pending U.S. application Ser. No. 16/440,504 the length of each flow modulating region 69 is preferably in the range of approximately 5-99% of the length of the prosthetic valve 10f, i.e. distance from proximal end 64 of the valve 10f to the distal end 62 of the valve 10f. More preferably, the length of each flow modulating region 69 is in the range of approximately 10-90% of the length of the prosthetic valve 10f.

As illustrated in FIG. 10C, in some embodiments, when the elongated ribbon members 60 are folded inwardly to form pre-formed valve structure 10e and, thereby, prosthetic valve 10f, the closed distal valve region 63' of prosthetic valve 10f comprises a cup-shaped configuration, wherein the length of the cup-shaped closed distal valve region 63' (denoted "a") is preferably at least approximately 5% of the length of the prosthetic valve 10f.

In some embodiments, when the elongated ribbon members 60 are folded inwardly to form pre-formed valve structure 10e and, thereby, prosthetic valve 10f, the closed distal valve region 63' of prosthetic valve 10f comprises a curvilinear shape, wherein the distance between the distal ends 68b of the flow modulating regions 69 and distal end 63 of the valve 10f is similarly preferably at least approximately 5% of the length of the prosthetic valve 10f.

As further illustrated in FIG. 10C, the proximal ends 64 of ribbon members 60 are also preferably positioned circumferentially about the proximal end of the valve 10f, i.e. cardiovascular valve structure engagement region 65, wherein prosthetic valve 10f, when fully formed, comprises a substantially conical shaped member.

The prosthetic valve 10f is similarly configured to expand during positive fluid flow through the valve 10f and contract during negative fluid flow through prosthetic valve 10f, e.g., regurgitating blood flow.

In a preferred embodiment, the fluid flow modulating regions 69 are similarly configured to open during expansion of the valve 10f, i.e. the first and second edge regions 61a, 61b separate, wherein the positive fluid flow is allowed to be transmitted through the fluid flow modulating regions 69, and close during the contraction of the valve 10f, wherein the negative fluid flow through valve 10f is restricted.

According to the invention, the valve 10f can comprise any number of ribbon members 60. In some embodiments of the invention, the valve 10f has three (3) equally spaced ribbon members 60.

Figure 10D:
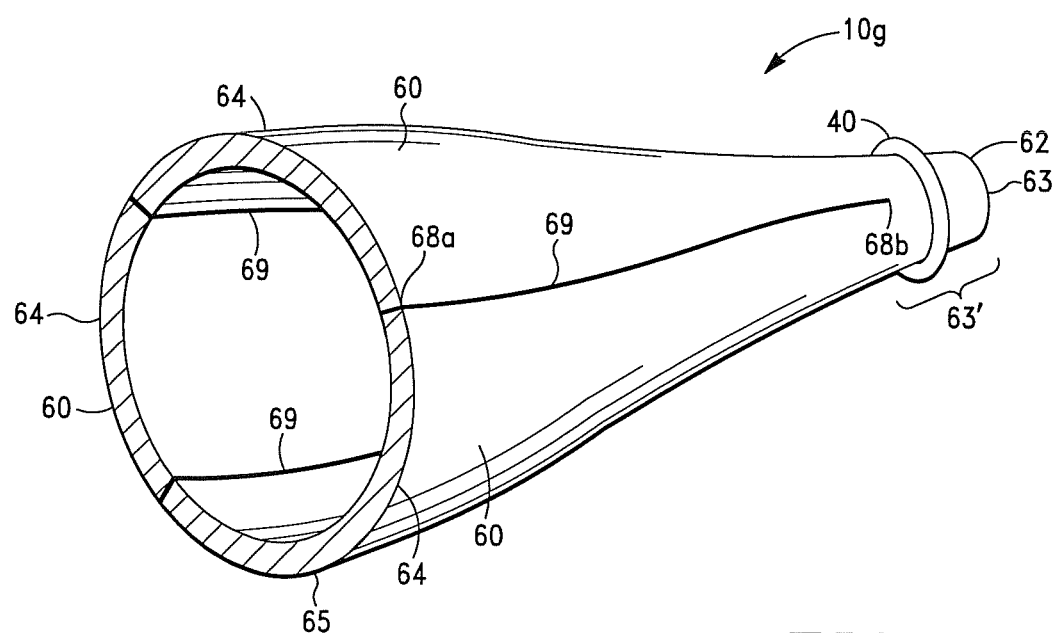
FIG. 10D is a perspective partial sectional view of another embodiment of the prosthetic valve shown in FIG. 10C having a structural ring disposed at the distal end of the valve, in accordance with the invention.

Referring now to FIG. 10D, there is shown another embodiment of the prosthetic valve 10f that is shown in FIG. 10C. As illustrated in FIG. 4D, the prosthetic valve, now denoted 10g, includes the aforementioned structural ring 40 that is disposed on the distal end 63 of the valve 10g. According to the invention, the structural ring 40 can be disposed at any position on the closed distal valve region 63' of prosthetic valve 10f.

Figure 10E:
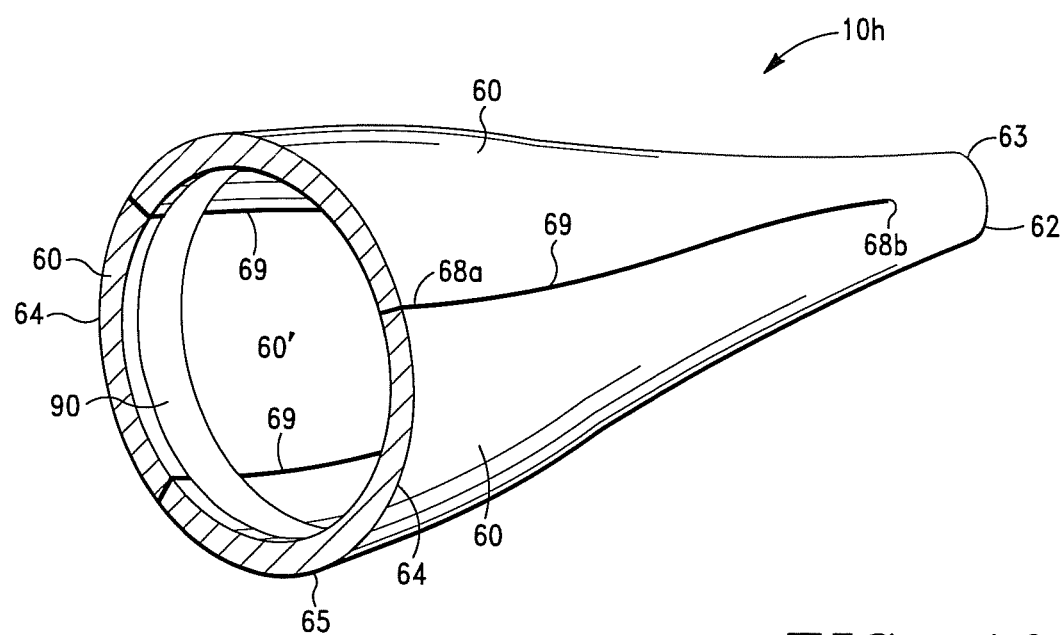
FIG. 10E is a perspective partial sectional view of another embodiment of the prosthetic valve shown in FIG. 10C having an annular ring disposed at the proximal end of the valve, in accordance with the invention.

Referring now to FIG. 10E, there is shown yet another embodiment of the prosthetic valve 10f that is shown in FIG. 10C. As illustrated in FIG. 10E, the prosthetic valve, now denoted 10h, includes an annular ring or anchor 90 that is disposed in the internal region "60'" on the proximal end of the valve 10h, i.e. cardiovascular valve structure engagement region 65.

According to the invention, the annular ring 90 can comprise one of the anchoring mechanisms 80 discussed above and shown in FIGS. 2A-7B.

As discussed in detail below, in some embodiments of the invention, the annular ring comprises a valve guide ring.

In a preferred embodiment, the annular ring 90 is configured to transition from a pre-deployment configuration to a post-deployment configuration.

Figure 10F:
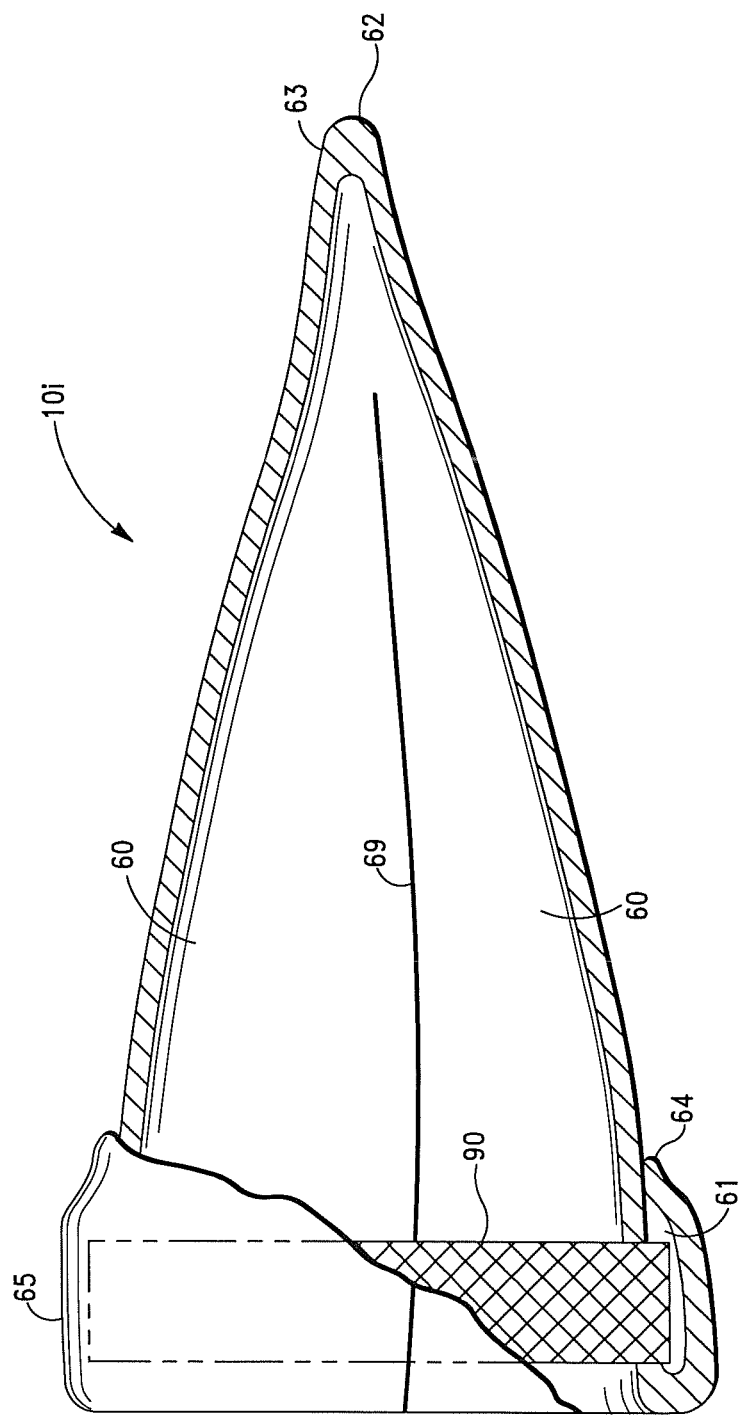
FIG. 10F is a perspective partial sectional view of another embodiment of the prosthetic valve shown in FIG. 10E having the annular ring disposed in an external valve pocket, in accordance with the invention.
Figure 10G:
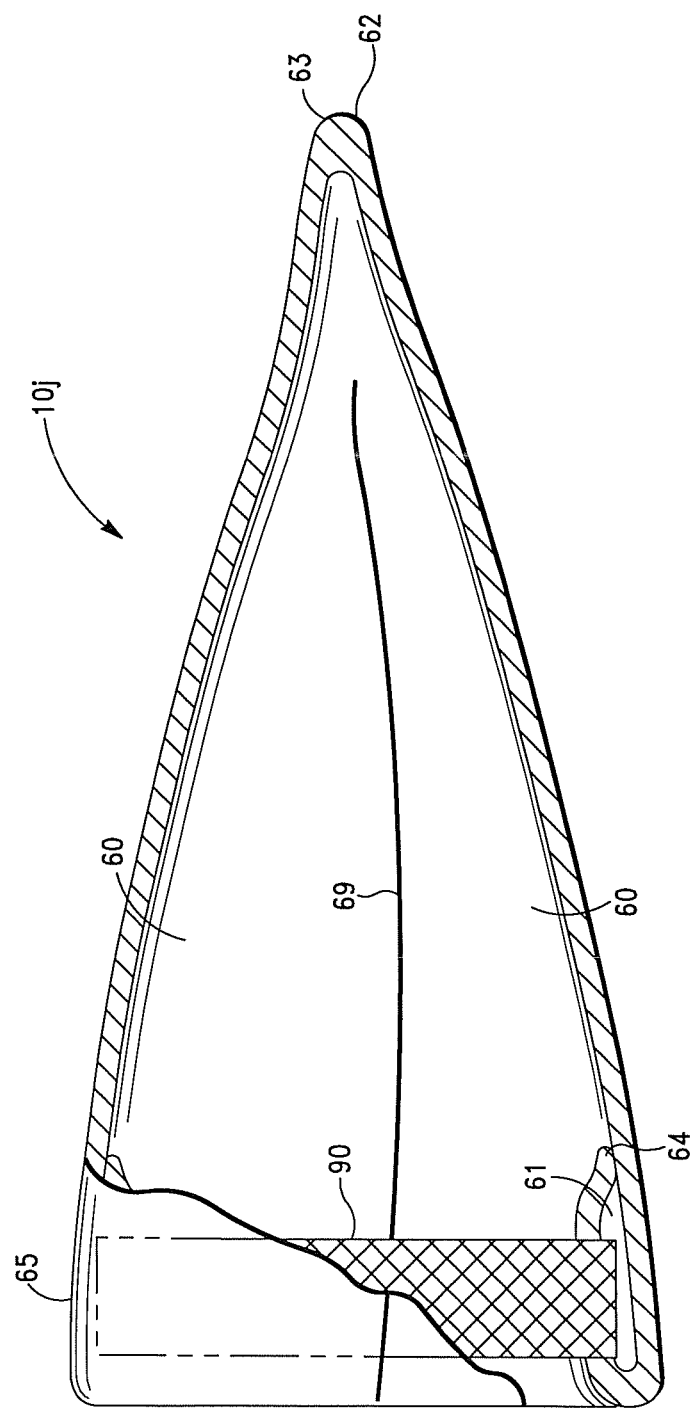
FIG. 10G is a perspective partial sectional view of another embodiment of the prosthetic valve shown in FIG. 10E having the annular ring disposed in an internal valve pocket, in accordance with the invention.

Referring now to FIGS. 10F and 10G, there are shown further embodiments of prosthetic "ribbon structure" valve 10h, wherein the cardiovascular valve structure engagement region 65 of the prosthetic valves, now denoted valves 10i and 10j, includes an annular ring 90 or valve guide ring.

In the embodiment illustrated in FIG. 10F, the proximal ends 64 of ribbon members 60 of prosthetic valve 10i, i.e. cardiovascular valve structure engagement region 65, are folded over outwardly to form an anchor pocket 61 proximate the outer surface of the valve 10i, which, as illustrated in FIG. 10F, is adapted to receive an annular ring 90 (or valve guide ring) therein.

In the embodiment illustrated in FIG. 10G, the proximal ends 64 of ribbon members 60 of prosthetic valve 10j, i.e. cardiovascular valve structure engagement region 65, are folded inwardly to form anchor pocket 61 proximate the inner surface of the valve 10j, which, as illustrated in FIG. 10G, is similarly adapted to receive an annular ring 90 (or valve guide ring) therein.

According to the invention, the prosthetic valve 10f (and valves 10g-10j) can further comprise at least one supplemental support structure, such as described in Applicant's U.S. Pat. Nos. 10,188,509, 10,188,510 and 10,052,409, which are similarly incorporated by reference herein.

Figure 10H:
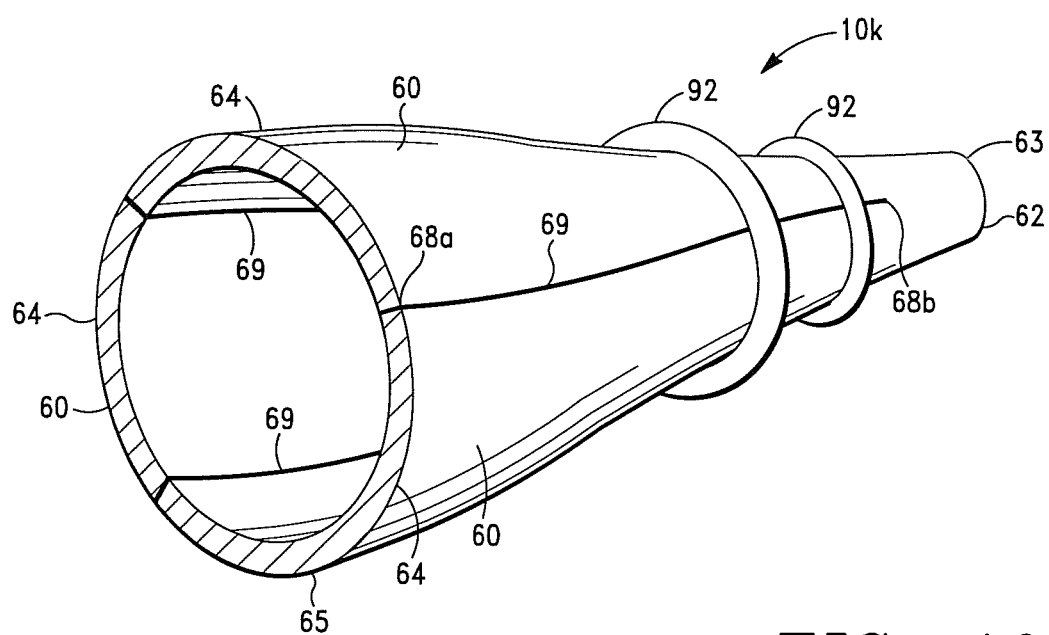
FIG. 10H is a perspective view of another embodiment the prosthetic valve shown in FIG. 10C having a plurality of external support rings disposed at the distal end of the valve, in accordance with the invention.

Referring now to FIG. 10H, there is shown an embodiment of the prosthetic valve 10f that is shown in FIG. 10C, wherein the prosthetic valve, now denoted 10k, includes multiple supplemental support structures (denoted "92") that are disposed on the mid-region of the valve 10k to enhance the structural integrity of the valve 10k.

According to the invention, the supplemental support structures 92 can be disposed at any point on a prosthetic valve of the invention.

According to the invention, the prosthetic valve 10k (and valves 10f-10j) can further comprise a stent structure, such as described in Applicant's Co-Pending U.S. Pat. No. 10,188,513, which is also incorporated by reference herein.

Figure 11:
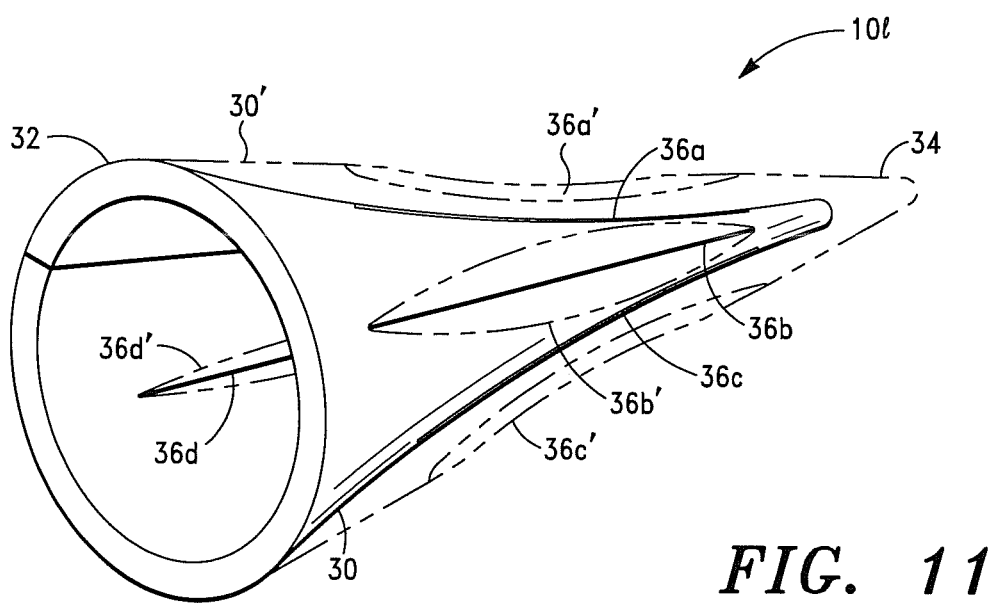
FIG. 11 is a perspective view of one embodiment of a prosthetic "sheet structure" valve, in accordance with the invention.

Referring now to FIG. 11, there is shown yet another embodiment of a prosthetic valve of the invention (denoted "10l").

As set forth in Co-pending U.S. application Ser. No. 16/129,968 and shown in FIG. 11, the valve 10l comprises a continuous conical shaped sheet member 30.

As illustrated in FIG. 11, the valve 10l further comprises an open proximal end 32, a closed distal end 34, and a plurality of open regions or interstices 36a-36d that are preferably disposed linearly over a portion of the length of the sheet member 30.

As also discussed in detail in Co-pending U.S. application Ser. No. 16/129,968, the sheet member 30 is preferably adapted to expand during positive fluid flow through the sheet member 30, as shown in phantom and denoted 30', and contract during negative fluid flow through the sheet member 30, e.g., regurgitating blood flow.

The interstices 36a-36d are also preferably configured to open during the noted expansion of the conical shaped member 30' (denoted 36a', 36b', 36c' and 36d'), wherein the positive fluid flow is allowed to be transmitted through the interstices 36a', 36b', 36c', 36d', and close during the noted contraction of the sheet member 30, wherein the negative fluid flow through said member 30 is restricted, more preferably, abated.

As indicated above, in some embodiments of the invention, the prosthetic valves of the invention comprise an anchoring mechanism that is designed and configured to position and, in some embodiments, securely engage the prosthetic valve; preferably, the proximal end thereof, to a valve annulus (and, hence, cardiovascular tissue associated therewith) and maintain contact therewith for a pre-determined anchor support time period.

According to the invention, any of the anchoring mechanisms described in Applicant's U.S. Pat. No. 9,044,319 can be employed in the prosthetic valves of the invention, and any variation thereof.

As described in detail in Applicant's U.S. Pat. No. 9,044,319, the prosthetic valves can similarly accommodate, i.e. seat, an anchoring mechanism on the proximal valve annulus engagement end by folding the proximal valve annulus engagement end inwardly toward the inner surface of the member or outwardly toward the outer surface of the member to form an anchor pocket that is configured to receive an anchoring mechanism therein.

According to the invention, the prosthetic valves of the invention can be implanted in the heart of a patient or subject using any conventional surgical technique.

Figure 12:
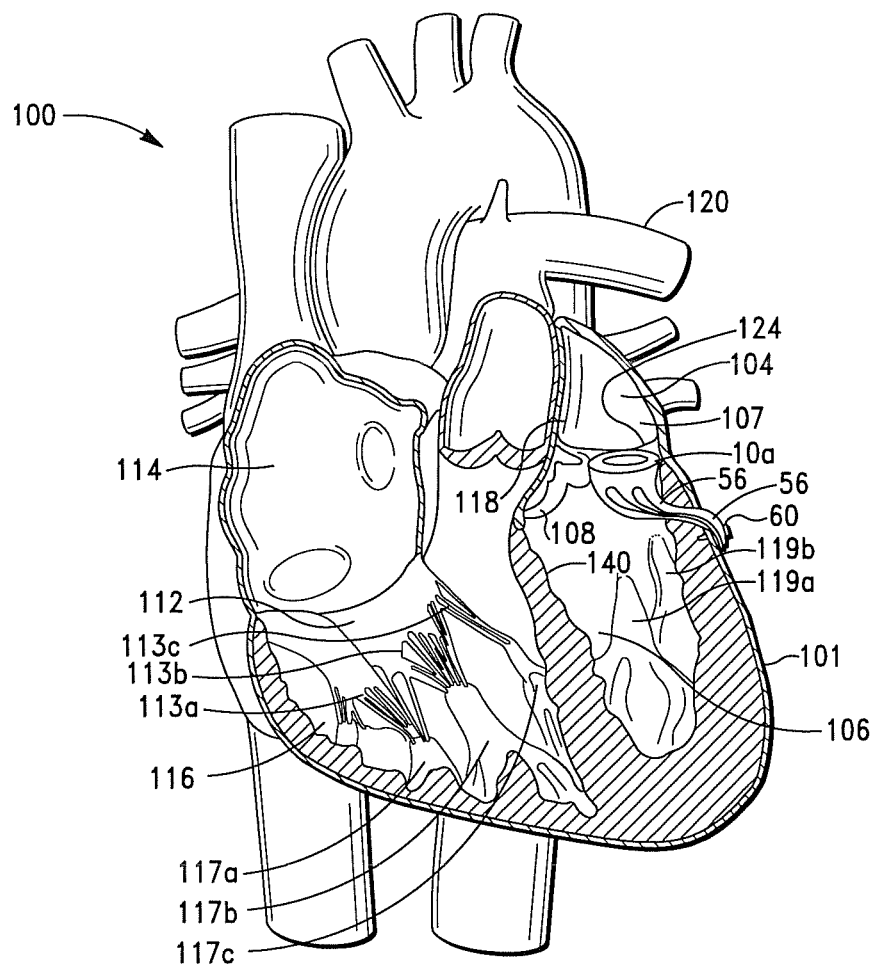
FIG. 12 is an illustration of the prosthetic "ribbon structure" valve shown in FIG. 8B secured to the mitral valve annulus region, in accordance with the invention.

Referring now to FIG. 12, there is shown one embodiment of prosthetic valve 10a disposed in a mitral valve region 124 of a subject's heart 100. As described in detail in Applicant's U.S. application Ser. No. 15/206,833, now U.S. Pat. No. 10,188,510 and shown in FIG. 12, the distal ends 56b of valve 10a in the illustrated embodiment are routed through the myocardium 140 of the left ventricle 106 and engaged thereto by a cork-screw mechanism 60.

In a preferred embodiment of the invention, the prosthetic valves of the invention are implanted in the heart of the subject using at least one embodiment of a novel percutaneous transseptal surgical implantation method of the invention discussed in detail below. The term "percutaneous, transseptal surgical implantation" as used herein means a minimally-invasively surgical procedure to access a subject's heart and implant a prosthetic valve of the invention or other prosthetic device therein.

The percutaneous transseptal surgical implantation methods of the invention provide highly effective means of positioning and securing the prosthetic valves of the invention to a cardiovascular structure of a heart.

A further advantage of percutaneous transseptal surgical implantation methods of the invention is that prosthetic valves of the invention can be implanted in a subject without removing the native valve, e.g., mitral valve.

A further advantage of percutaneous transseptal surgical implantation methods of the invention is that when employed to replace a mitral valve with a prosthetic valve of the invention, the prosthetic valve is positioned in the mitral valve region, wherein the leaflets of the aortic valve are allowed to freely coapt, whereby the outflow tract of the aortic valve is unobstructed. The aortic valve's function is thus unaffected and the core function of a subject's heart is retained and, in some instances, improved when compared to initial native function.

According to the invention, the first steps in the percutaneous transseptal surgical implantation methods of the invention are to identify and provide (i) the desired prosthetic valve to be implanted in the subject and (ii) the appropriate catheter assembly to access the subject's heart, i.e. a structure thereof, and deploy the prosthetic valve thereto.

For the sole purpose of describing the catheter assembly and percutaneous transseptal surgical implantation methods of the invention, prosthetic "ribbon structure" valve 10a shown in FIGS. 8A and 8B will be selected for implantation in a subject.

Figure 13:
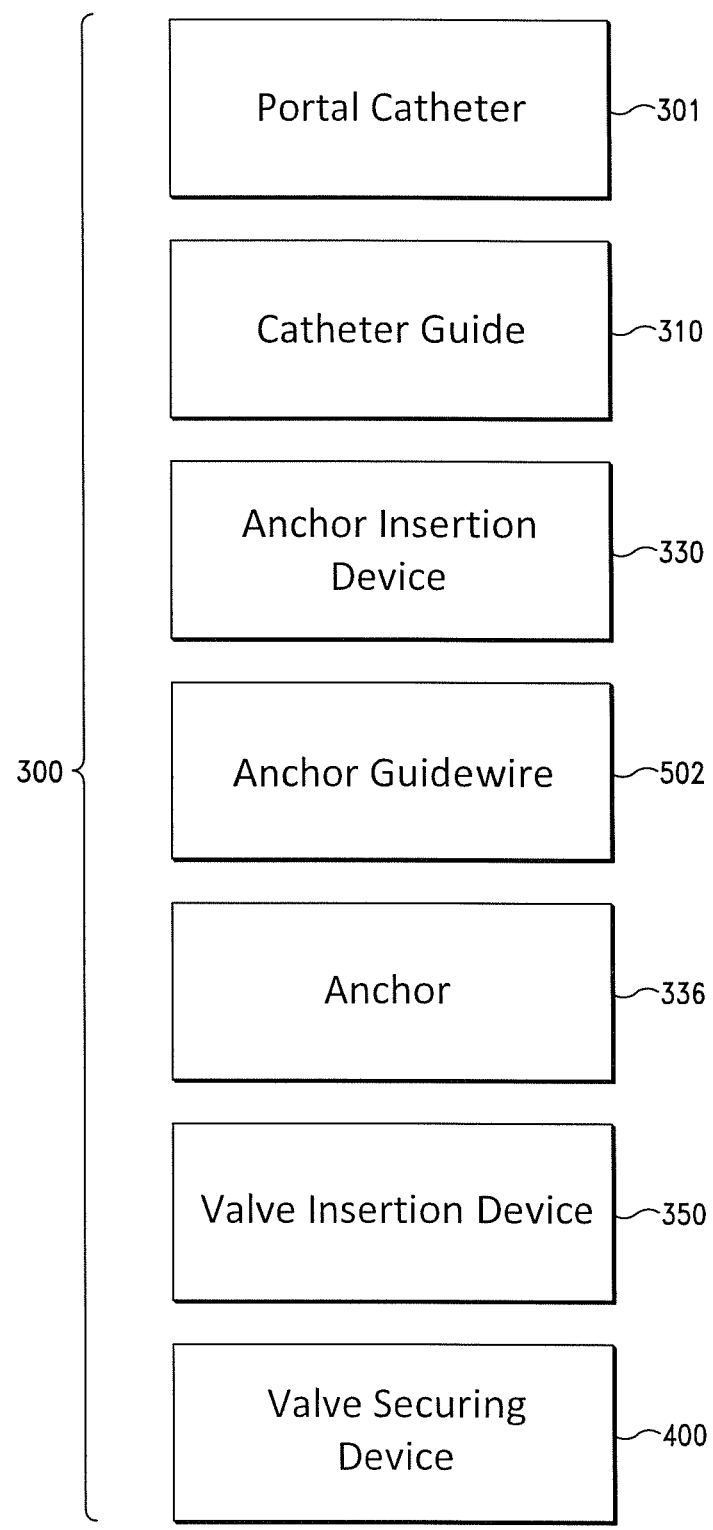
FIG. 13 is a schematic illustration of one embodiment of a catheter assembly, in accordance with the invention.

As illustrated in FIG. 13 and discussed in detail in Co-Pending U.S. application Ser. Nos. 16/238,730 and 16/193,669, which are expressly incorporated by reference herein, the preferred catheter assembly 300 generally comprises a portal catheter 301, catheter guide 310, anchor insertion device 330, anchor guidewire 502, anchor 336, valve insertion device 350 and valve securing device 400.

Figure 14A:
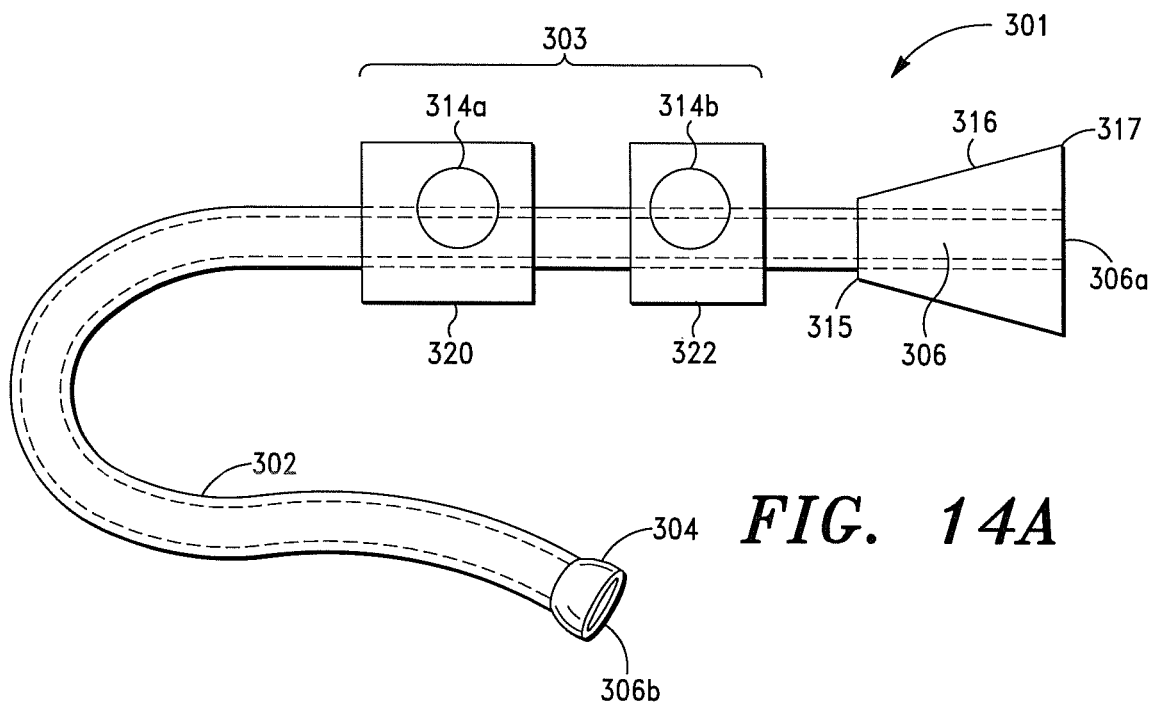
FIG. 14A is an illustration of one embodiment of a portal catheter, in accordance with the invention.

Referring now to FIG. 14A, the portal catheter 301 preferably comprises a catheter control assembly 303, a handle 316 with distal and proximal ends 315, 317, and a catheter portal sheath 302 with proximal and distal ends 306a, 306b and an access portal 306, i.e. internal lumen, therein that is sized and configured to receive and route therethrough the catheter guide 310, anchor insertion device 330, valve insertion device 350 and valve securing device 400 of the catheter assembly 300, discussed below, and other surgical instruments, e.g. endoscope.

In a preferred embodiment, the catheter control assembly 303 comprises a first actuation module 320 having a first actuation mechanism 314a and a second actuation module 322 having a second actuation mechanism 314b, which jointly are designed and configured to maneuver the catheter portal sheath 302 and any device disposed in the catheter portal sheath 302, e.g., catheter guide 310.

As set forth in Co-Pending U.S. application Ser. Nos. 16/238,730 and 16/193,669, the first and second actuation modules 320, 322 of the catheter control assembly 301 can be in communication with a control device, e.g., a computer, which can be controlled by an operator or remotely controlled surgical system, such as the da Vinci® Remote Surgical System.

As also set forth in Co-Pending U.S. application Ser. Nos. 16/238,730 and 16/193,669, the catheter portal sheath 302 preferably comprises a polymeric material, e.g., silicone, poly(tetrafluoroethylene) (PTFE) and poly(ethylene terephthalate) (PET or Dacron®).

Figure 14B:
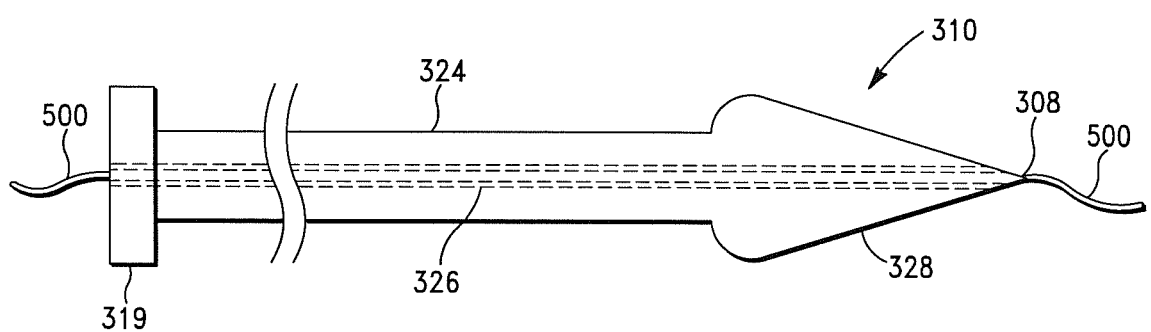
FIG. 14B is an illustration of one embodiment of a catheter guide, in accordance with the invention.
Figure 14C:
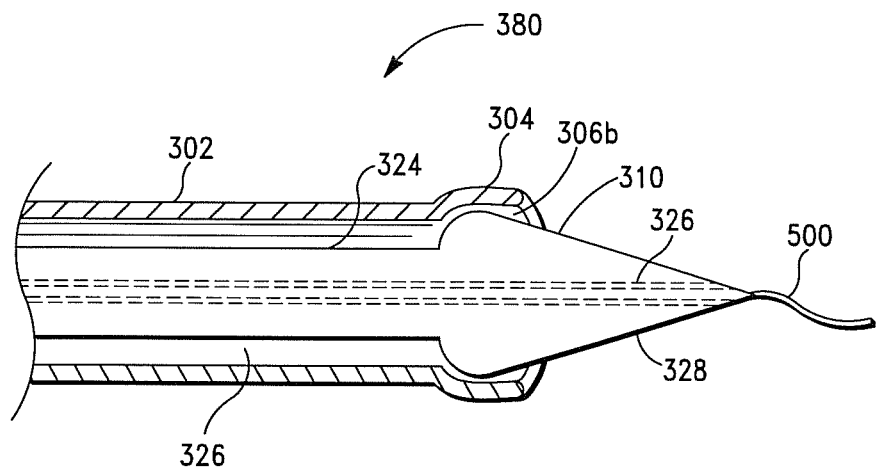
FIG. 14C is a partial front, partial sectional view of one embodiment of a catheter sub-assembly comprising the portal catheter and catheter guide shown in FIGS. 14A and 14B, in accordance with the invention.
Figure 14D:
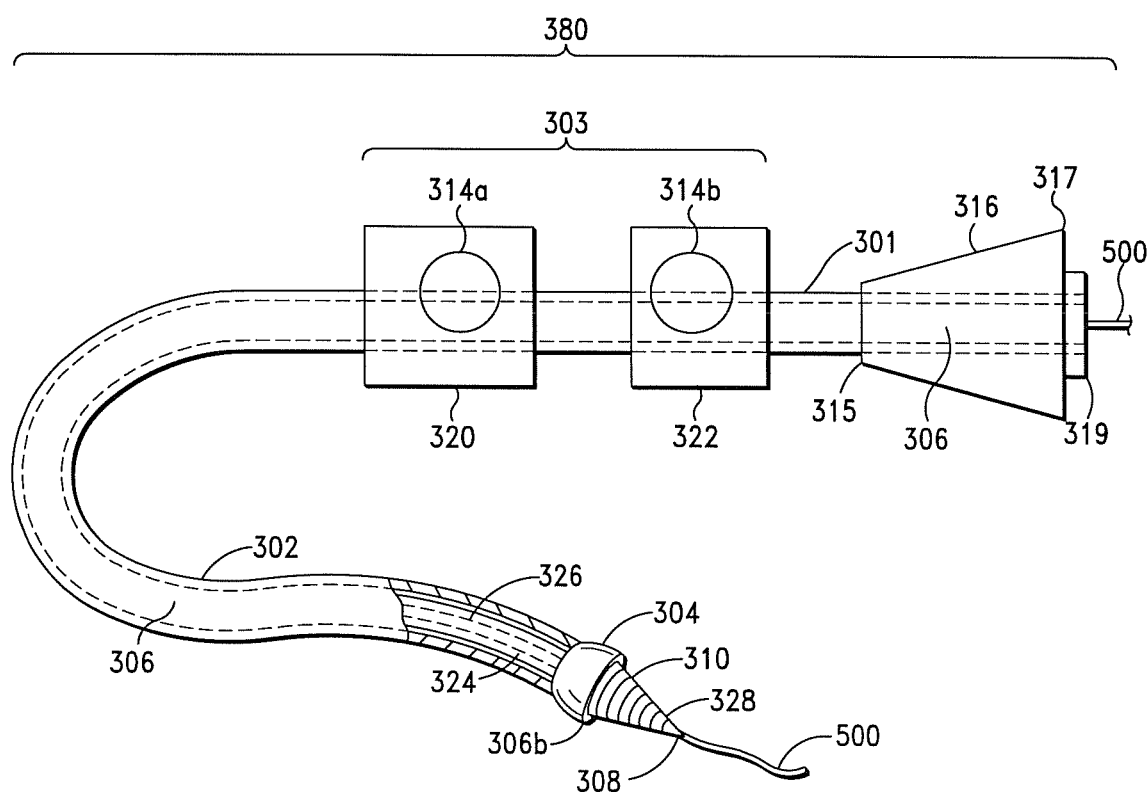
FIG. 14D is a front plan, partial sectional view of the catheter sub-assembly shown in FIG. 14C, in accordance with the invention.

Referring now to FIGS. 14B, 14C and 14D, as indicated above, the catheter assembly 300 further comprises a catheter guide 310, which, as discussed in detail below, is sized and configured to be routed through and retracted from the access portal 306 of the catheter sheath 302. The catheter guide 310 is also adapted to be positioned and removeably secured to the distal end 304 of the catheter portal sheath 302 (when employed) to form a catheter sub-assembly 380, as shown in FIG. 14D.

As further illustrated in FIGS. 14B, 14C and 14D, the catheter guide 310 preferably comprises proximal and distal ends 319, 308, a guide head 328, and a guide shaft 324 having an internal lumen 326 that is sized and configured to receive a guidewire 500 therein.

As also set forth in Co-Pending U.S. application Ser. Nos. 16/238,730 and 16/193,669, the guide head 328 is preferably configured to penetrate and, preferably, pierce through biological tissue, e.g., a tapered distal end 308. The guide head 328 is also adapted to direct the guidewire 500 therethrough and into biological tissue.

The guide head 328 can comprise any suitable shape or size; provided, the size and shape accommodates entry into and through the catheter portal sheath 302, i.e. the access portal 306 thereof.

In some embodiments, the guide head 328 comprises or includes an expandable member that is configured to expand and removably secure the guide head 328 inside the access portal 306 of the catheter sheath 302 at the distal end 304 thereof.

As discussed in detail below, the guidewire 500 is preferably adapted to be routed into a cardiovascular structure via the guide 310 (or any other conventional guide), and function as guide for various tools and devices required to perform (or facilitate) the percutaneous transseptal surgical implantation methods of the invention.

Figure 15A:
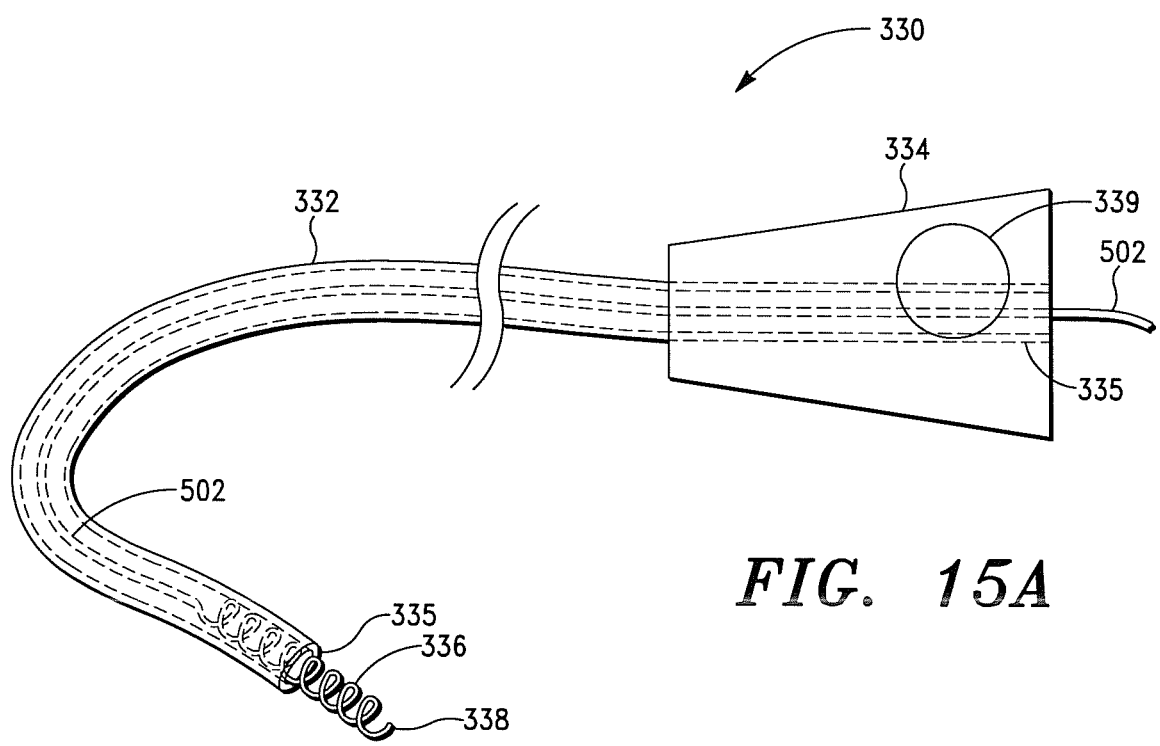
FIG. 15A is an illustration of one embodiment of an anchor insertion device, in accordance with the invention.
Figure 15B:
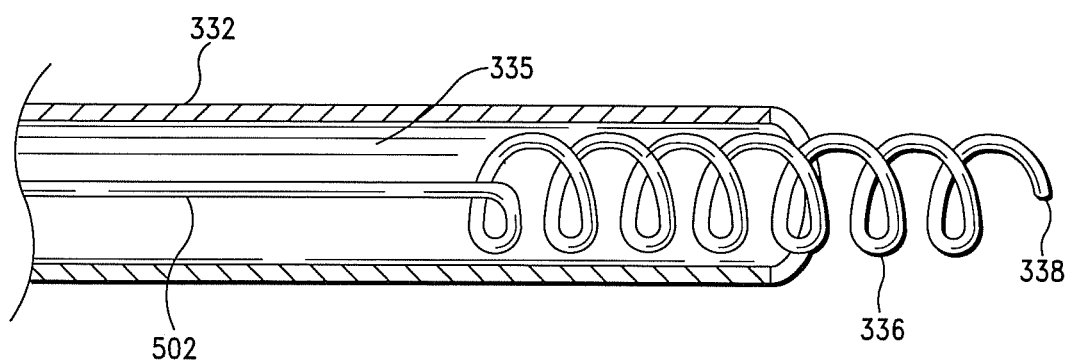
FIG. 15B is a partial front plan, partial sectional view of the anchor insertion device shown in FIG. 15A, in accordance with the invention.
Figure 15C:
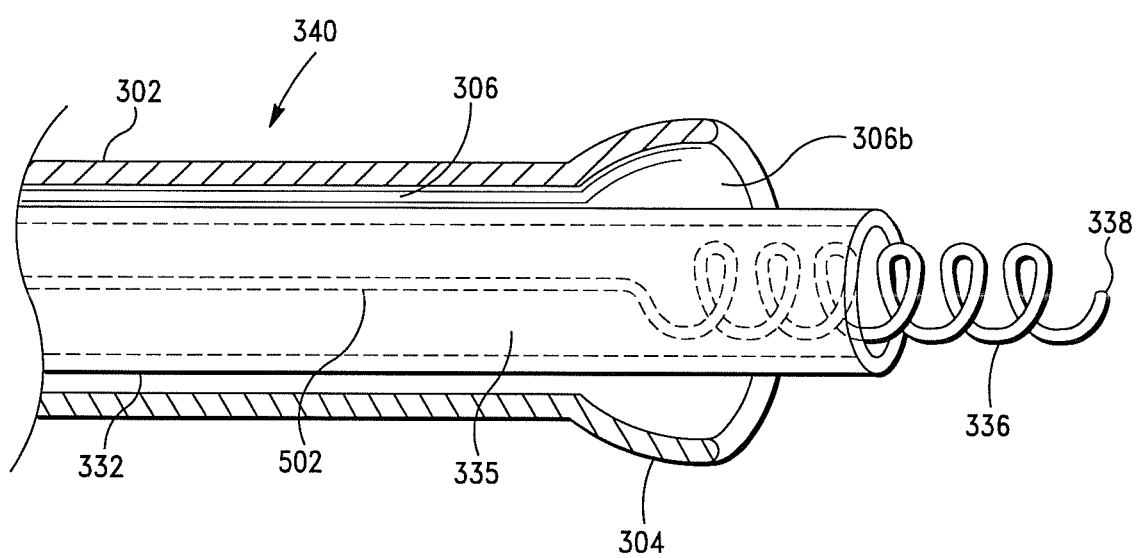
FIG. 15C is a partial front, partial sectional view of another embodiment of a catheter sub-assembly comprising the portal catheter and anchor insertion device shown in FIGS. 14A and 15A, in accordance with the invention.

Referring now to FIGS. 15A-15C, the anchor insertion device 330 preferably comprises a handle 334 having an actuation mechanism 339 and an elongated member 332, which is similarly sized and configured to be routed through and retracted from the catheter portal sheath 302 (when employed), as illustrated in FIG. 15C.

As illustrated in FIGS. 15A and 15B, the elongated guide member 332 includes an internal lumen 335, which is configured to receive a further anchor guidewire 502 therein.

As also illustrated in FIGS. 15A and 15B, the guidewire 502 comprises an anchor tip (or anchor) 336 disposed at the distal end 338 of guidewire 502.

As illustrated in FIG. 15C, the elongated member 332 of anchor insertion device 330 is configured to be routed through catheter portal sheath 302 to form a further catheter sub-assembly 340 to access a cardiovascular structure and deploy the anchor guidewire 502 thereto.

As set forth in Co-Pending U.S. application Ser. Nos. 16/238,730 and 16/193,669, the actuation mechanism 339 of the anchor insertion device 330 is designed and configured to maneuver the elongated member 332 of the anchor insertion device 330 and, hence, anchor guidewire 502 and/or any guidewire and/or device disposed in the internal lumen 335 of the elongated member 332.

As also set forth in Co-Pending U.S. application Ser. Nos. 16/238,730 and 16/193,669, the elongated member 332 preferably comprises a flexible tubular member that is configured to defect between 0-180° relative to a predetermined axis at any point along the member 332 to enable to the elongated member 332 to access various cardiovascular structures and positions therein and proximate thereto.

As illustrated in FIGS. 15A-15C, in some embodiments, the anchor tip 336 comprises a conventional leadscrew, e.g., a Nitinol® wormscrew, having a diameter in the range of 0.001-25 mm.

Figure 16C:
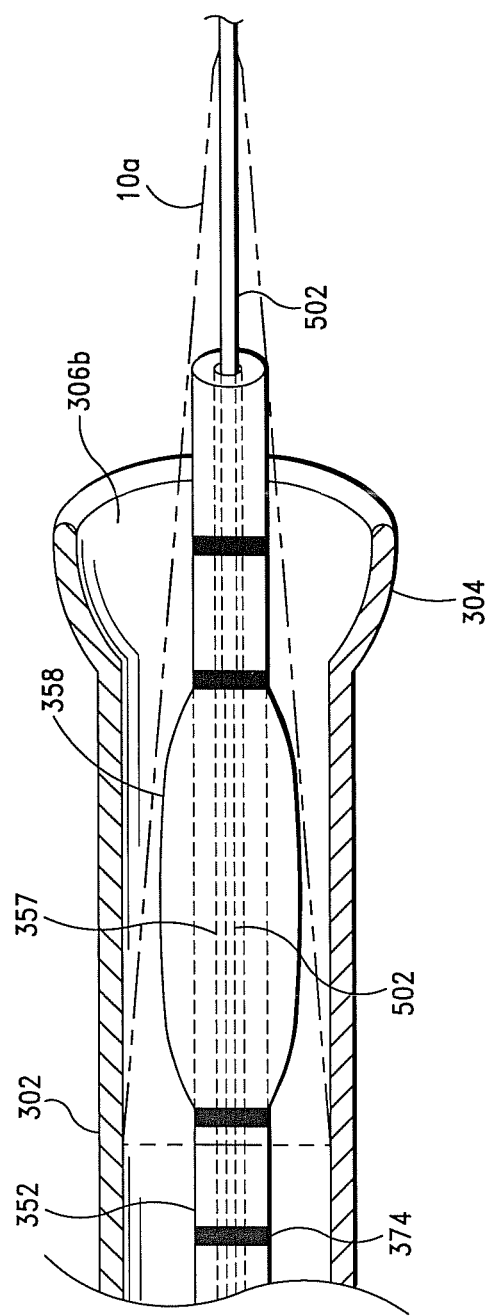
FIG. 16C is a partial front, partial sectional view of another embodiment of a catheter sub-assembly comprising the portal catheter and valve insertion device shown in FIGS. 14A and 16A, in accordance with the invention.

Referring now to FIGS. 16A-16C, the valve insertion device 350, which, as discussed in detail below, is similarly sized and configured to be routed through and retracted from the catheter portal sheath 302 (when employed), preferably comprises a valve insertion member 352, a base member 362 having an internal lumen 351 therein, and proximal and distal ends 366, 354.

The valve insertion member 352 further preferably comprises an expandable member 358 disposed proximate the distal end 354 of the insertion member 352 that is configured and adapted to transition from a pre-deployment configuration to an expanded, post-deployment configuration (as shown in phantom and denoted 360).

Referring now to FIGS. 16B and 16C, there is shown prosthetic valve 10a disposed on the distal end 354 of the valve insertion member 352, wherein the valve 10a and anchoring mechanism 80 (not shown) are positioned over the expandable member 358.

As set forth in Co-Pending U.S. application Ser. Nos. 16/238,730 and 16/193,669, and discussed in detail below, when the expandable member 358 transitions from a pre-deployment configuration to an expanded, post-deployment configuration 360, the expandable member 358 applies a radial force to an anchoring mechanism 80 of prosthetic valve 10a (when employed), whereby the anchoring mechanism 80 and, hence, prosthetic valve 10a also transitions from a pre-deployment configuration to a post-deployment configuration.

The expandable member 358 can comprise any conventional member or system that is capable of expanding from a pre-deployment configuration to an expanded post-deployment configuration and, thus, applying radial force to an anchoring mechanism of a valve or other prosthesis when in communication therewith.

In a preferred embodiment, the expandable member 358 comprises a conventional balloon member.

As further illustrated in FIG. 16A, in a preferred embodiment, the base member 362 of the valve insertion device 350 comprises an air-line or intake 364 that is in communication with an air source 370 via intake tube 372. The air source 370 is preferably configured to provide pressurized air to the expandable member 358 through the base member 362 internal lumen 351, which allows the expandable member 358 to transition from the unexpanded, pre-deployment configuration to the expanded, post-deployment configuration 360.

As indicated above, the valve insertion device 350 and, hence, valve insertion member 352 thereof is sized and configured to be routed through (and extracted from) the catheter portal sheath 302 to access a cardiovascular structure, e.g., a mitral valve region, and deploy a prosthetic valve of the invention proximate thereto. Preferably, the valve insertion member 352 is designed and configured to be guided through a biological tissue structure via a deployed guidewire, such as the anchor guidewire 502 shown in FIGS. 16A and 16B.

As further illustrated in FIGS. 16A-16C, the valve insertion device 350 preferably comprises a plurality of markers 374 that are adapted to provide visual guidance for an operator of the valve insertion device 350 during the percutaneous transseptal surgical implantation methods of the invention.

Figure 17A:
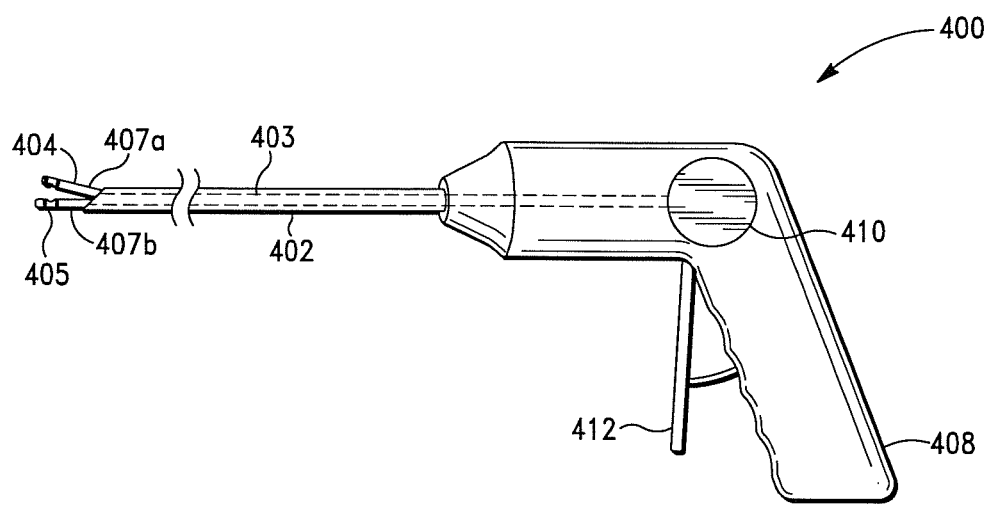
FIG. 17A is an illustration of one embodiment of a valve securing device, in accordance with the invention.
Figure 17B:
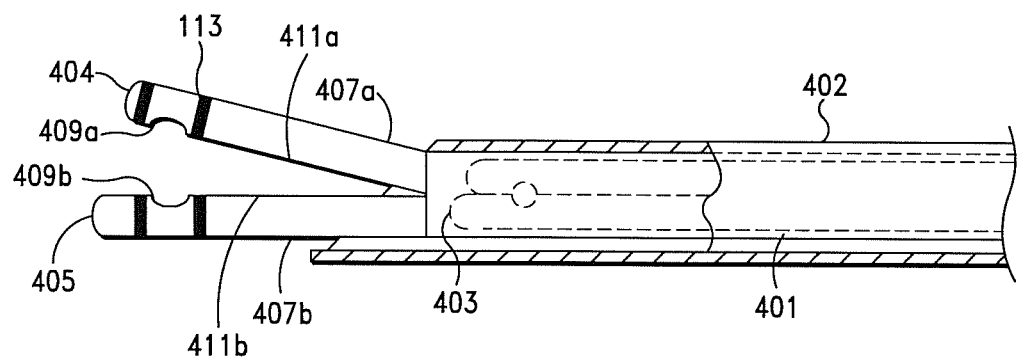
FIG. 17B is a partial front, partial sectional view of the valve securing device shown in FIG. 17A, showing the multi-function distal end thereof in extended and contracted configurations, in accordance with the invention.
Figure 17C:
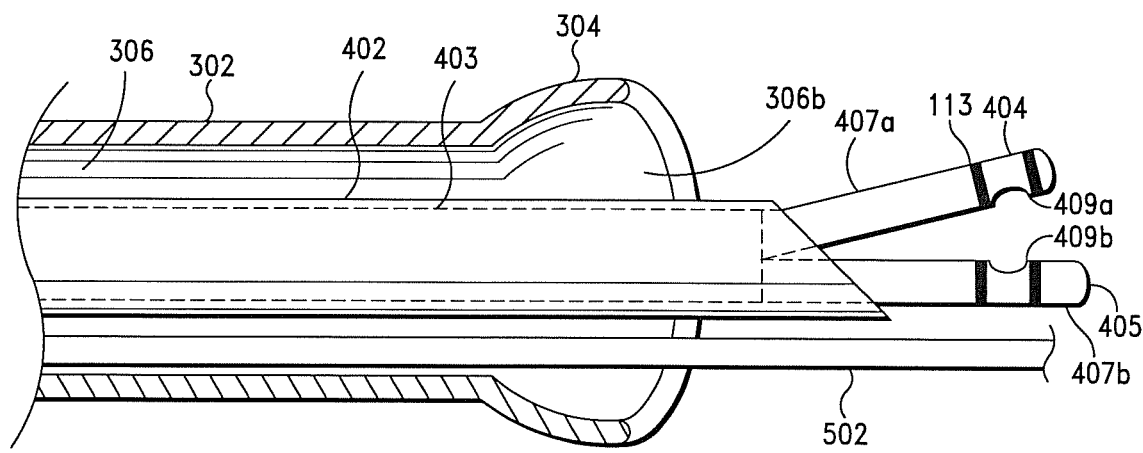
FIG. 17C is a partial front, partial sectional view of another embodiment of a catheter sub-assembly comprising the portal catheter and valve securing device shown in FIGS. 14A and 17A, in accordance with the invention.

Referring now to FIGS. 17A-17C, the valve securing device 400 includes a securing shaft 402, which is similarly sized and configured to be routed through and retracted from the catheter portal sheath 302 (when employed), as illustrated in FIG. 17C.

As illustrated in FIG. 17A, the valve securing device 400 preferably comprises a handle 408 having first and second actuation mechanisms 410, 412 and a securing shaft 402 having an internal guide/control shaft 403 with a multi-function distal end 404.

As indicated above and shown in FIG. 17C, the securing shaft 402 is preferably designed and configured to be routed through the catheter portal sheath 302 to access a target cardiovascular structure and secure a distal end (or proximal end) of a prosthetic valve proximate thereto.

As set forth in Co-Pending U.S. application Ser. Nos. 16/238,730 and 16/193,669, the multi-function distal end 404 of the internal guide/control shaft 403 is preferably configured to maneuver and secure structural elements of a prosthetic valve, such as the ribbons 56 of prosthetic valve 10a shown in FIG. 8A, to a cardiovascular structure.

As also set forth in Co-Pending U.S. application Ser. Nos. 16/238,730 and 16/193,669, the multi-function distal end 404 is also preferably configured to advance the anchor tip 336 of anchor guidewire 502 into and, preferably, engage the anchor tip 336 to a cardiovascular structure.

In some embodiments, the multi-function distal end 404 is also configured to sever a guidewire, e.g., anchor guidewire 502, at a predetermined point.

As illustrated in FIGS. 17A-17C, the multi-function distal end 404 of the internal guide/control shaft 403 preferably comprises a tong member 405 having an elongated top portion 407a and a cooperating elongated bottom portion 407b.

Preferably, the elongated top portion 407a of the tong member 405 is configured or pre-shaped to transition from a restrained static or pre-deployment configuration when the internal guide/control shaft 403 is in a retracted position, wherein, as illustrated in FIG. 17B, the tong member 405 (shown in phantom) is disposed in the internal guide/control shaft lumen 401, to an unrestrained configuration, when the internal guide/control shaft 403 is in an extended position and the tong member 405 is extending out of the internal guide/control shaft lumen 401.

As further illustrated in FIG. 17B, the elongated top and bottom portions 407a, 407B of the tong member 405 preferably comprise cooperating anchor seats 409a, 409b, which are configured to seat, engage and advance the anchor tip 336 of anchor guidewire 502, and cutting regions 411a, 411b, which are configured to sever a guidewire, e.g., anchor guidewire 502.

In some embodiments, the elongated top and bottom portions 407a, 407b of the tong member 405 further comprise radio-opaque markers 113 that are disposed proximate the cooperating anchor seats 409a, 409b and cutting regions 411a, 411b to provide visual alignment of the anchor seats 409a, 409a and cutting regions 411a, 411b when the valve securing device 400 is employed to seat, engage and advance the anchor tip 336 of anchor guidewire 502, and sever a guidewire; particularly, anchor guidewire 502.

As set forth in Co-Pending U.S. application Ser. Nos. 16/238,730 and 16/193,669, the securing shaft 402 of the valve securing device 400 is preferably maneuverable and controlled via the first actuation mechanism 410 disposed on the handle 408 of the device 400, and the multi-function distal end 404 is preferably maneuverable and controlled via the second actuation mechanism 412 disposed on the handle 408 of the device 400.

As also set forth in Co-Pending U.S. application Ser. Nos. 16/238,730 and 16/193,669, the securing shaft 402 of valve securing device 400 preferably comprises a flexible component that is similarly preferably configured to defect between 0-180° relative to a predetermined axis at any point along the shaft 402 to enable to the shaft 402 and, hence, multi-function distal end 404 thereof, to access a target cardiovascular structure.

After the desired prosthetic valve is selected and the catheter assembly and associated devices, e.g., catheter guide, anchor insertion device, valve insertion device and valve securing device, are prepared for the percutaneous transseptal surgical implantation (denoted steps "i" and "ii" above), (iii) the catheter guide 310 (and guidewire 500) is routed through the catheter portal sheath 302, i.e. the access portal 306 thereof, and positioned and removeably secured to the distal end 304 thereof to form catheter sub-assembly 380.

After the catheter sub-assembly is prepared (denoted step "iii"), (iv) a vein is selected for accessing the subject's heart.

According to the invention, various veins and tributaries thereof can be employed to access the subject's heart, e.g., femoral vein, popliteal vein and great saphenous vein. In a preferred embodiment, the femoral vein is employed to access the subject's heart.

Figure 18:
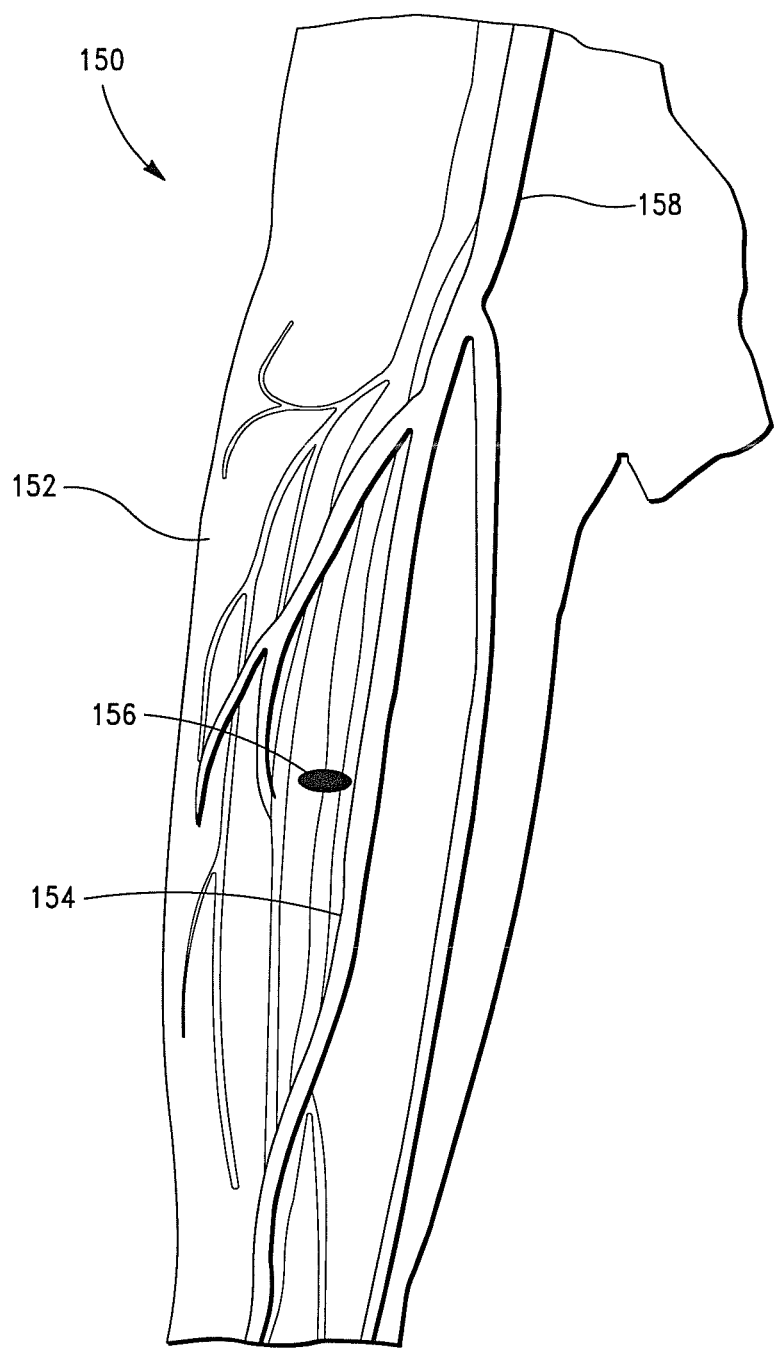
FIG. 18 is an illustration of a subject's leg showing an incision proximate the femoral vein, in accordance with the invention.

Referring now to FIG. 18, after the vein is selected, in this instance the femoral vein (denoted step "iv"), (v) an incision 156 is placed in and through tissue in the leg 152 of subject 150 proximate the femoral vein 154 to provide access therein by the catheter sub-assembly 380.

Figure 19:
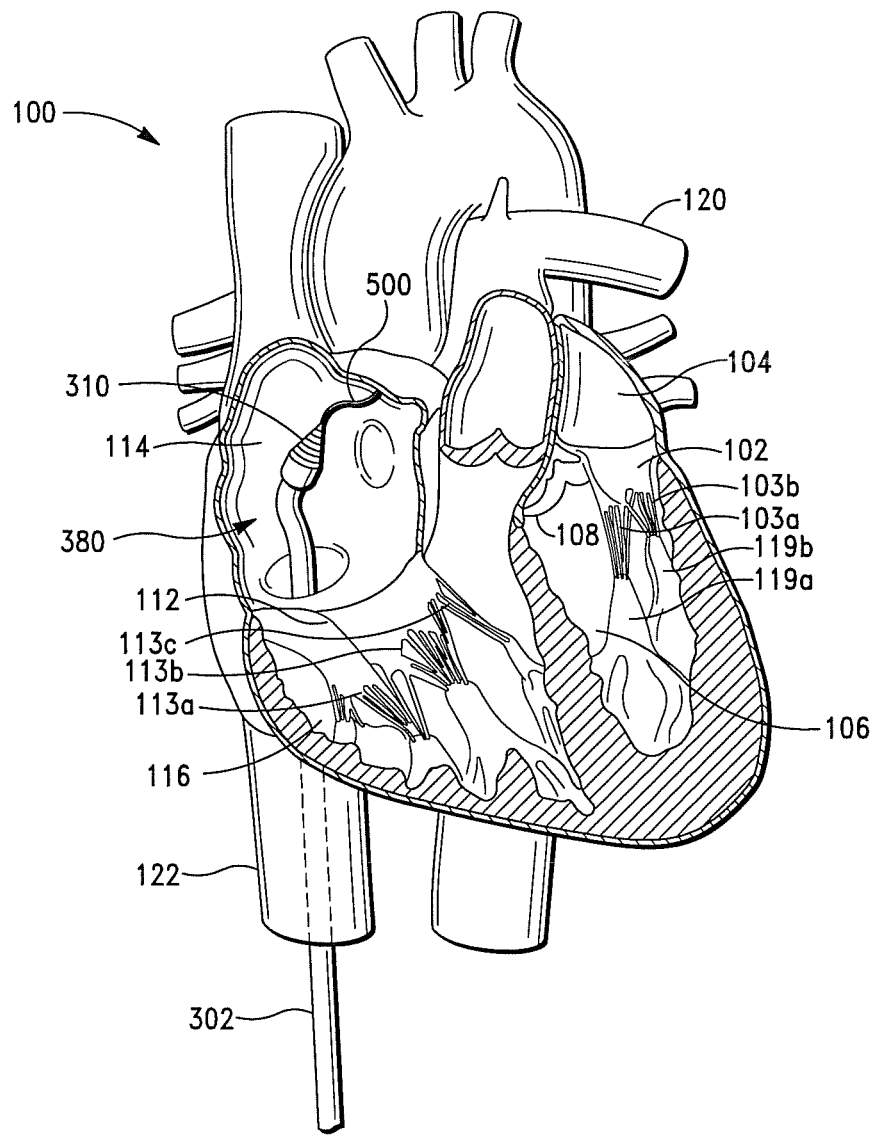
FIG. 19 is an illustration of a mammalian heart showing the routing of a catheter sub-assembly, i.e. portal catheter and catheter guide, through the inferior vena cava and into the right atrium of the subject's heart, in accordance with the invention.

After the incision is made (denoted step "v"), (vi) the catheter sub-assembly 380 is routed into the incision 156 and into the femoral vein 154. As illustrated in FIG. 19, the catheter sub-assembly 380 is then further routed into the right atrium 114 of the subject's heart 100; preferably, up the common iliac vein 158, into the inferior vena cava 122 and into the right atrium 114.

Preferably, catheter control assembly 303 and handle 316 remain outside of the body of subject 150 and are accessible by an operator, e.g., a surgeon.

Figure 20:
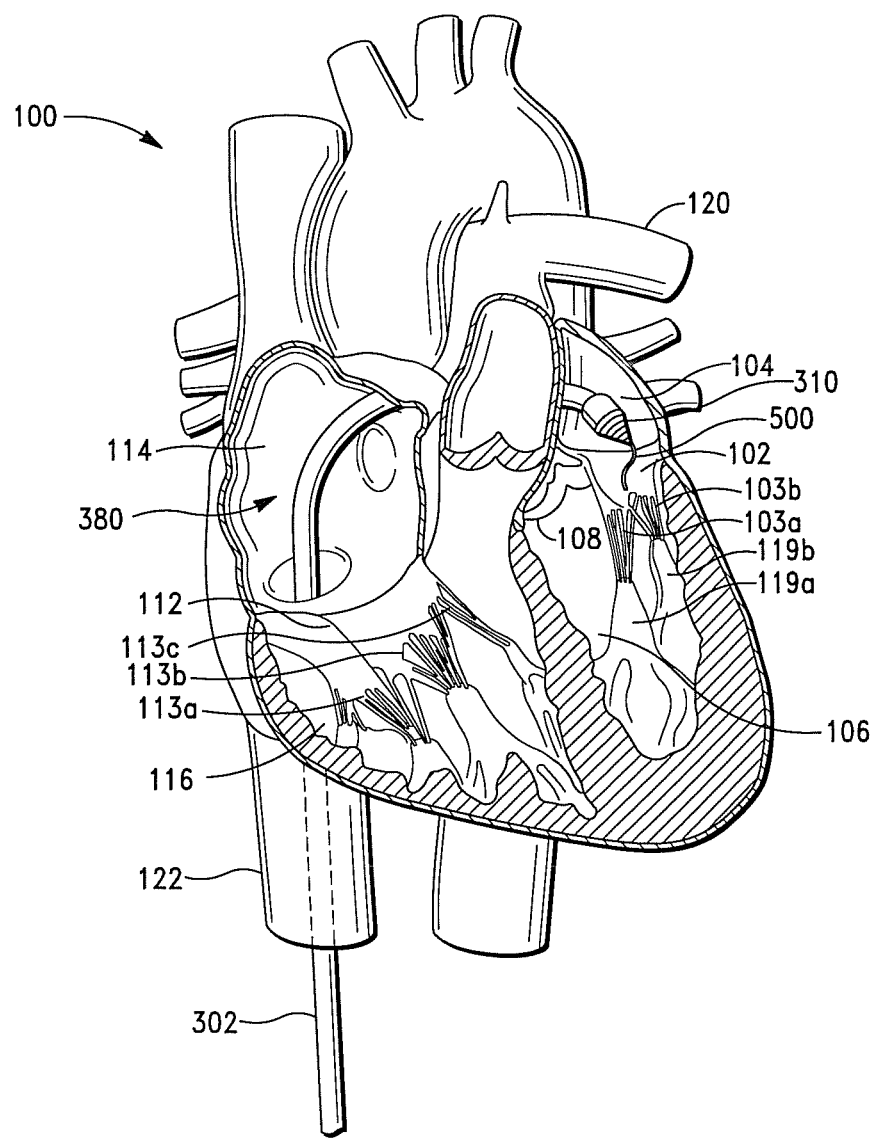
FIG. 20 is a further illustration of the mammalian heart shown in FIG. 19 showing the routing of the catheter sub-assembly, i.e. portal catheter and catheter guide, into the left atrium of the subject's heart, in accordance with the invention.

As illustrated in FIG. 20, after the catheter sub-assembly 380 is routed into the right atrium 114 (denoted step "vi"), (vii) the catheter guide 310 is guided into the left atrium 104 of the subject's heart 100.

Figure 21:
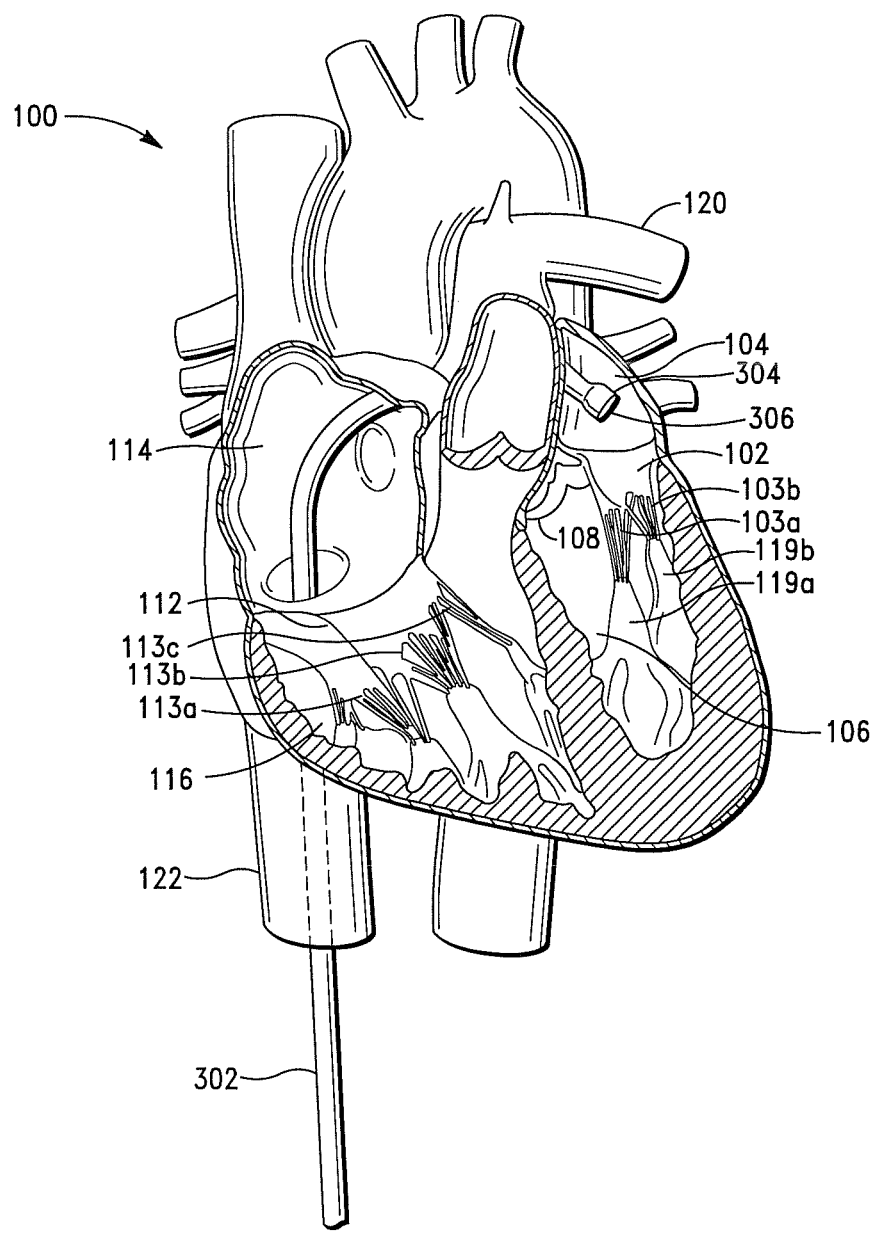
FIG. 21 is a further illustration of the mammalian heart shown in FIG. 19 showing the portal catheter positioned in the left atrium, in accordance with the invention.

As illustrated in FIG. 21, after the catheter sub-assembly 380 has been routed into the left atrium 104 of heart 100 (denoted step "vii"), (viii) the catheter guide 310 (and guidewire 500) of the sub-assembly 380 is retracted through the catheter portal sheath 302, leaving the distal end 304 of the catheter portal sheath 302 disposed in the left atrium 104 of the subject's heart 100 to, as discussed below, provide access thereto by the anchor insertion device 330, valve insertion device 350 and valve securing device 400, prosthetic valve 10a, and other surgical instruments, e.g., an endoscope.

Figure 22:
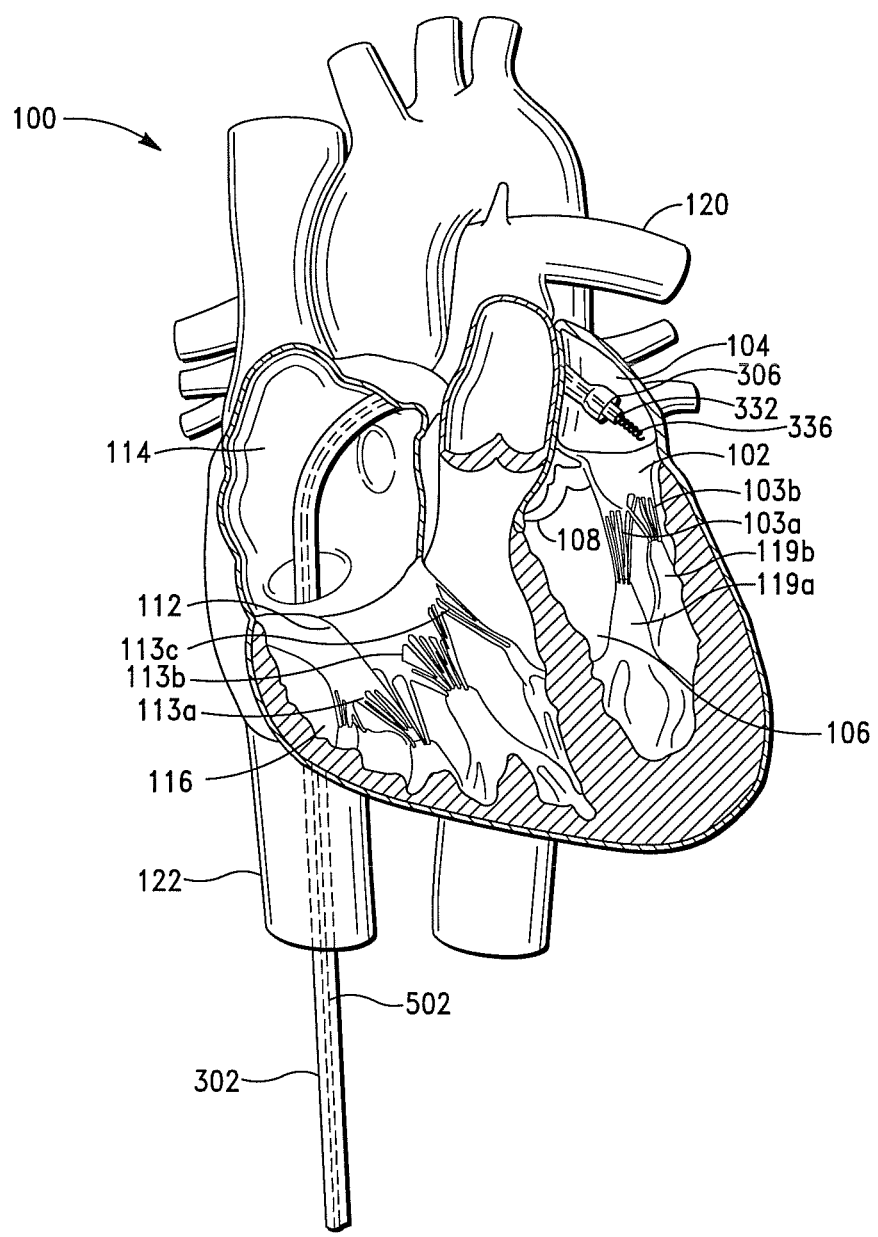
FIG. 22 is a further illustration of the mammalian heart shown in FIG. 19 showing a further catheter sub-assembly, i.e., portal catheter and anchor insertion device, positioned in the left atrium of the subject's heart, in accordance with the invention.
Figure 23:
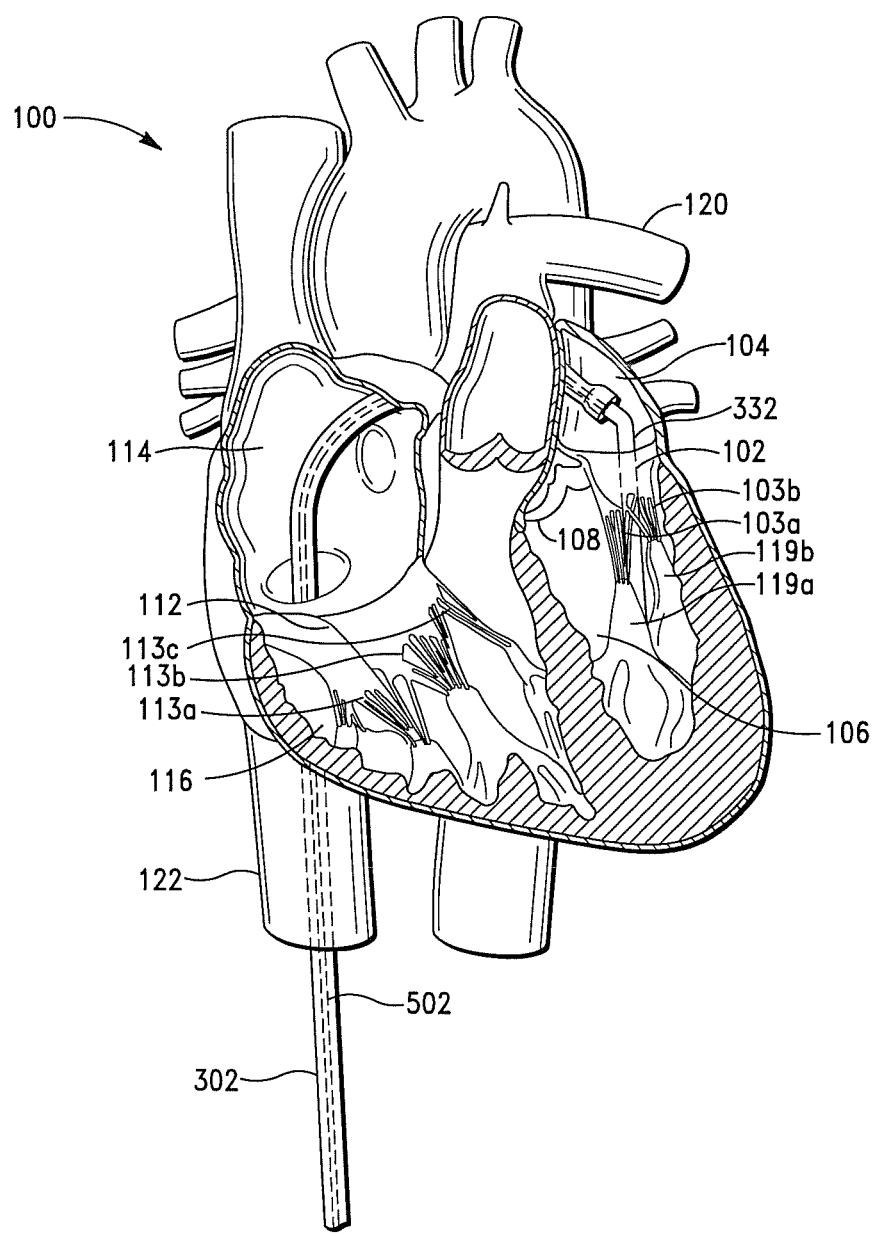
FIG. 23 is a further illustration of the mammalian heart shown in FIG. 19 showing the catheter sub-assembly, i.e., portal catheter and anchor insertion device, shown in FIG. 22 routed through the mitral valve and into the left ventricle of the subject's heart, in accordance with the invention.

As illustrated in FIGS. 22 and 23, after the catheter guide 310 of catheter sub-assembly 380 is retracted through the catheter portal sheath 302 (denoted step "viii"), (ix) the anchor insertion device 330 (and anchor guidewire 502) is inserted into the catheter portal sheath 302 and (x) routed into the left atrium 104, through mitral valve 102 and into the left ventricle 106 of the heart 100.

Figure 24:
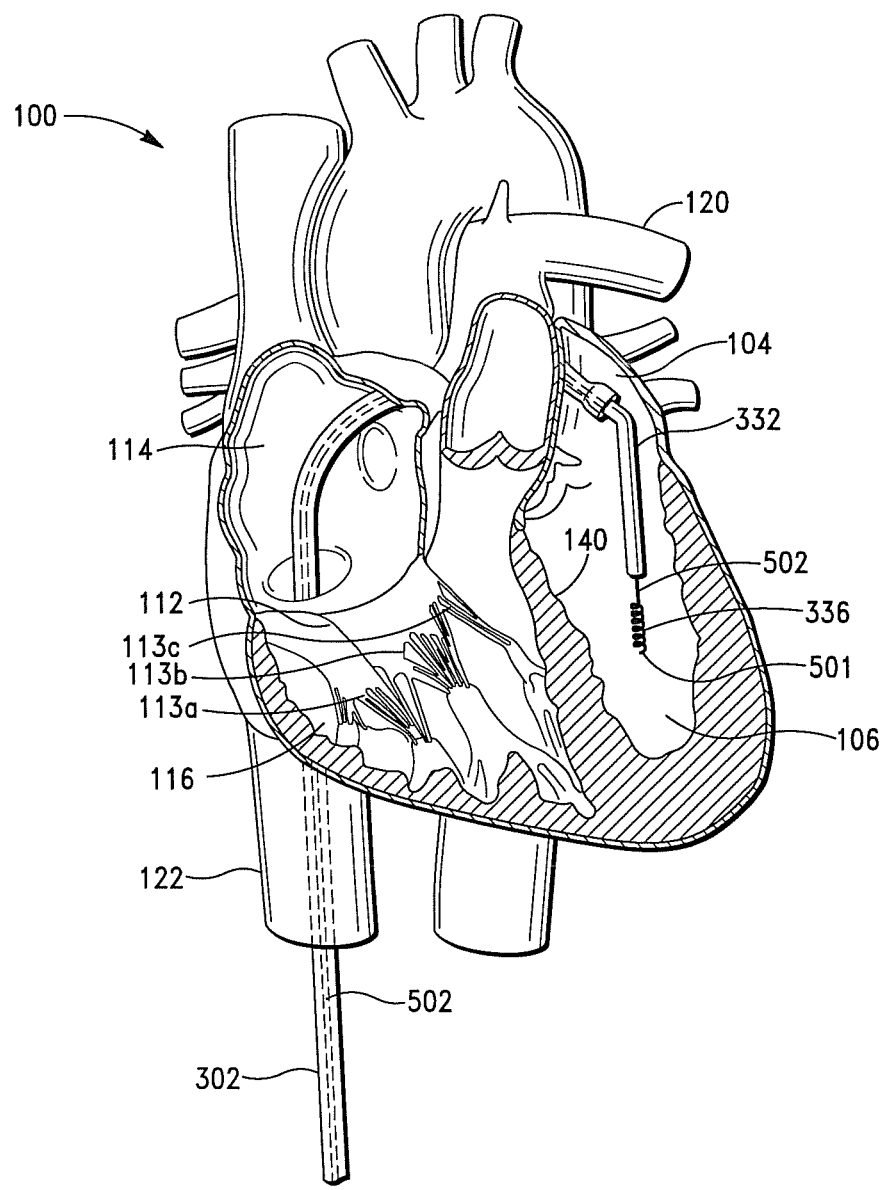
FIG. 24 is a further illustration of the mammalian heart shown in FIG. 19 showing the anchor tip of the anchor insertion device anchor guidewire positioned at a predetermined point between the anterior and posterior papillary muscles of the left ventricle, in accordance with the invention.

As illustrated in FIG. 24, after the anchor insertion device 330 (and anchor guidewire 502) is inserted into the catheter portal sheath 302 and routed into the left ventricle 106 of the heart 100 (denoted steps "ix" and "x"), (xi) the anchor tip 336 of the anchor guidewire 502 is then positioned at a predetermined anchor attachment point 501 between the anterior and posterior papillary muscles 119a, 119b of the left ventricle 106.

After the anchor tip 336 is positioned in the left ventricle 106 (denoted step "xi"), (xii) the anchor tip 336 is driven into and secured to, i.e. engages, the myocardium 140 of the left ventricle 106 at the anchor attachment point 501.

Figure 25:
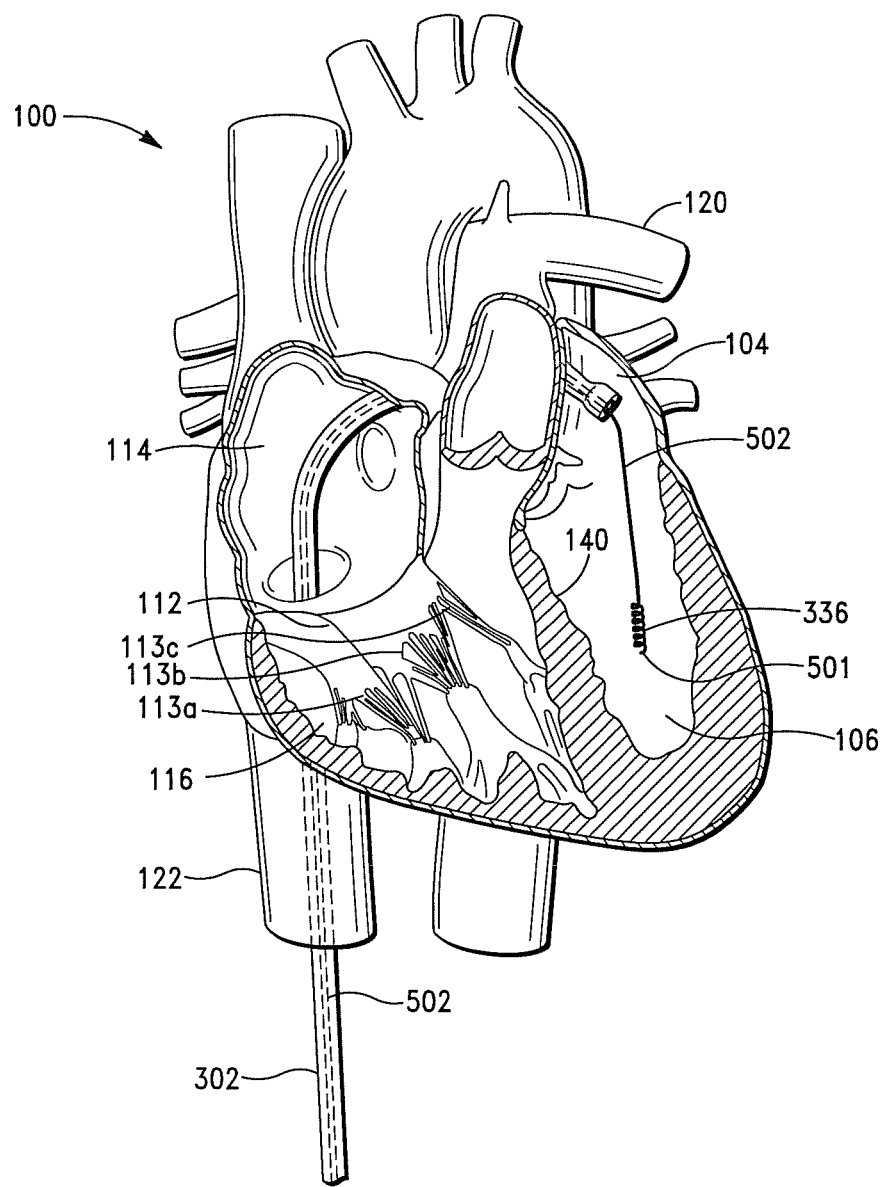
FIG. 25 is a further illustration of the mammalian heart shown in FIG. 19 showing the anchor tip of the anchor insertion device engaged to the myocardium of the left ventricle, in accordance with the invention.

As illustrated in FIG. 25, after the anchor tip 336 is engaged to the myocardium 140 (denoted step "xii"), (xiii) the anchor insertion device 330 is withdrawn through the catheter portal sheath 302.

As also illustrated in FIG. 25, the anchor guidewire 502 is not withdrawn and anchor tip 336 remains engaged to, i.e. anchored in, the myocardium 140 of the left ventricle 106.

After the anchor insertion device 330 is withdrawn through the catheter portal sheath 302 (denoted step "xiii"), (xiv) the prosthetic valve, in this instance prosthetic valve 10a, is positioned on the valve insertion member 352 of the valve insertion device 350 such that the valve 10a and anchoring mechanism 80 thereof is positioned over expandable member 358.

Figure 26:
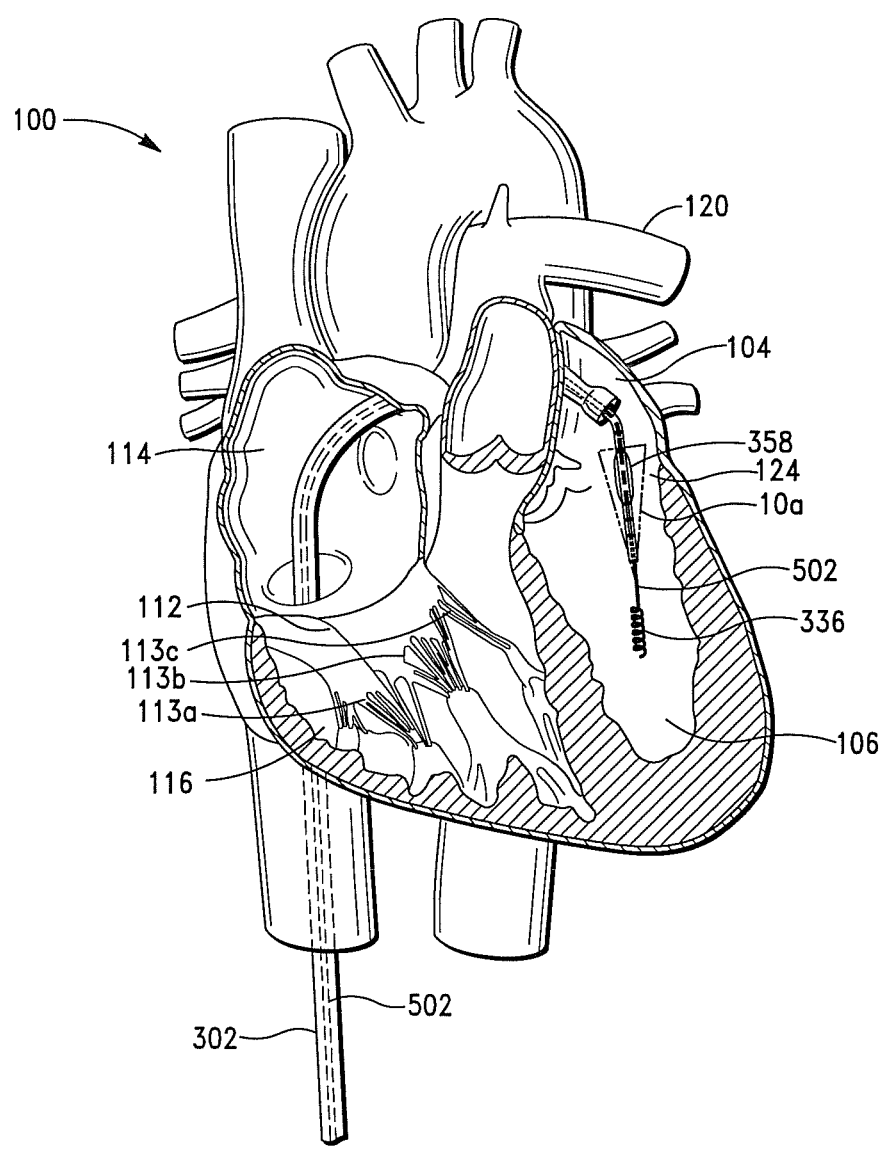
FIG. 26 is a further illustration of the mammalian heart shown in FIG. 19 showing a valve insertion device with a prosthetic valve engaged thereto positioned in the left ventricle by the anchor guidewire, in accordance with the invention.

As illustrated in FIG. 26, after prosthetic valve 10g is positioned on the valve insertion device 350 (denoted step "xiv"), (xv) the valve insertion device 350 with prosthetic valve 10a engaged thereto is guided into and through the catheter portal sheath 302 along anchor guidewire 502 and into the mitral valve region 124 (i.e. AV valve annulus region) of heart 100.

Figure 27:
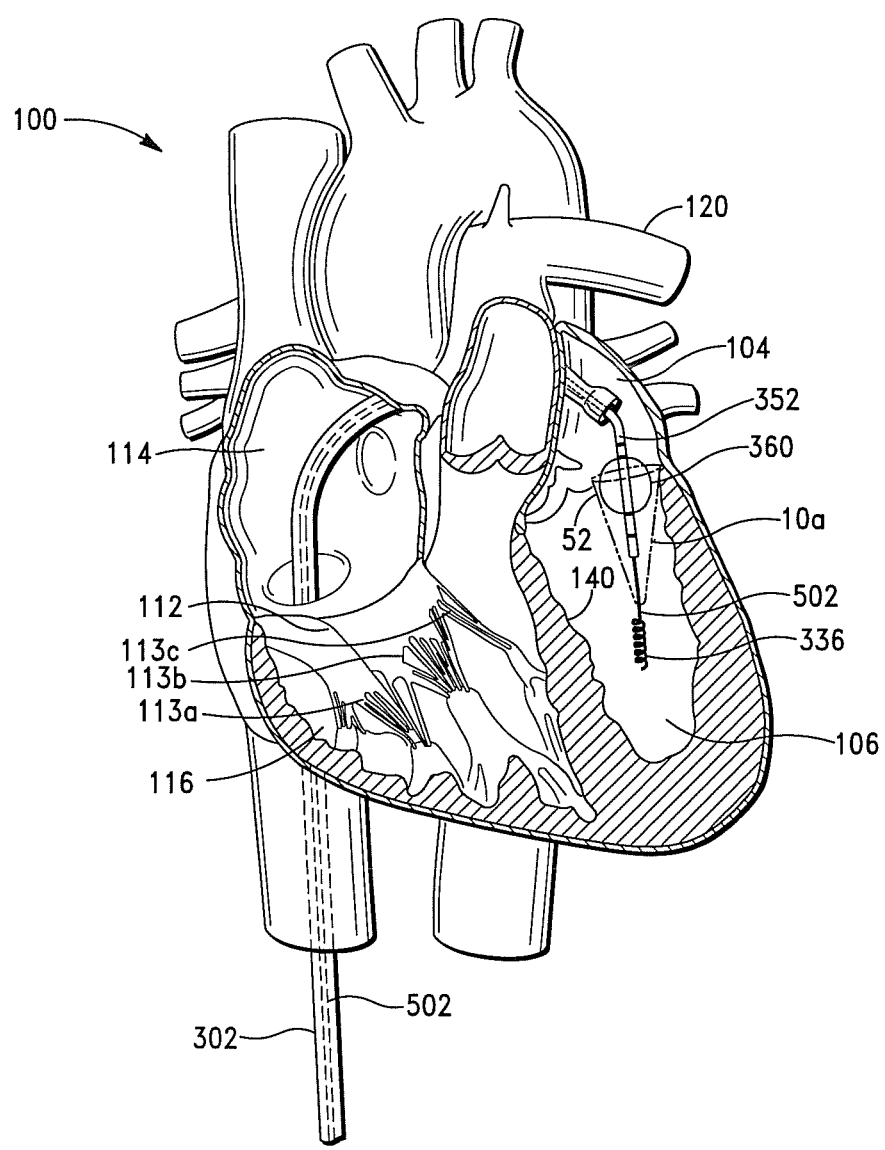
FIG. 27 is a further illustration of the mammalian heart shown in FIG. 19 showing the valve insertion device and prosthetic valve in expanded post-deployment configurations, in accordance with the invention.

As illustrated in FIG. 27, after the valve insertion device 350 with prosthetic valve 10a engaged thereto is guided into and through the catheter portal sheath 302 and into the mitral valve region 124 of heart 100 (denoted step "xv"), (xvi) the expandable member 358 of the valve insertion member 352 is expanded, wherein the expandable member 358 and, thereby, prosthetic valve 10a (and anchoring mechanism 80 (when employed)) transition from pre-deployment configurations to expanded, post-deployment configurations, whereby prosthetic valve 10a; preferably, the proximal annulus engagement end 52 thereof, is positioned in and, preferably disposed adjacent the mitral valve region 124 of the heart 100.

Figure 28:
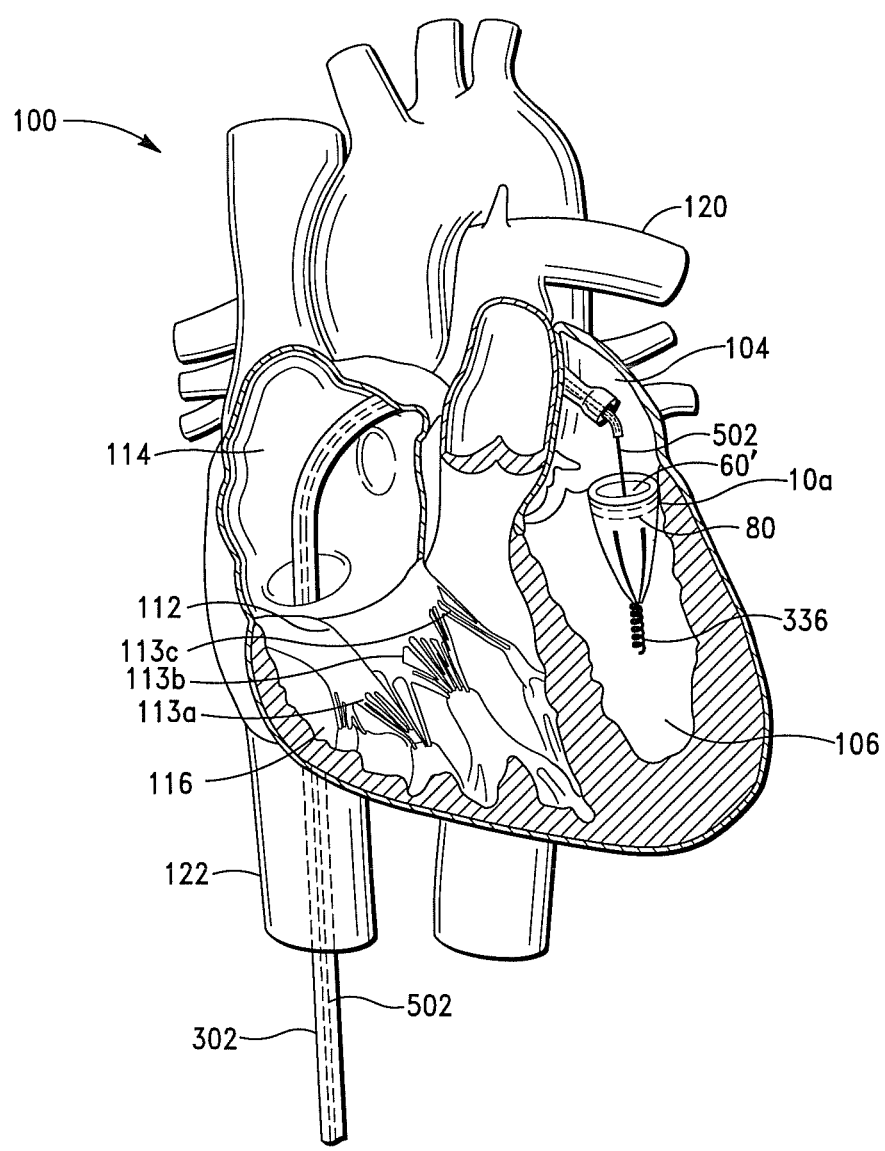
FIG. 28 is a further illustration of the mammalian heart shown in FIG. 19 showing the valve insertion device partially retracted in the portal catheter, in accordance with the invention.

Referring now to FIG. 28, after the prosthetic valve 10a is deployed in the mitral valve region 124 (denoted step "xvi"), (xvii) the prosthetic valve insertion device 350 is retracted through the catheter portal sheath 302 along the anchor guidewire 502 and out of the subject's body.

Figure 29:
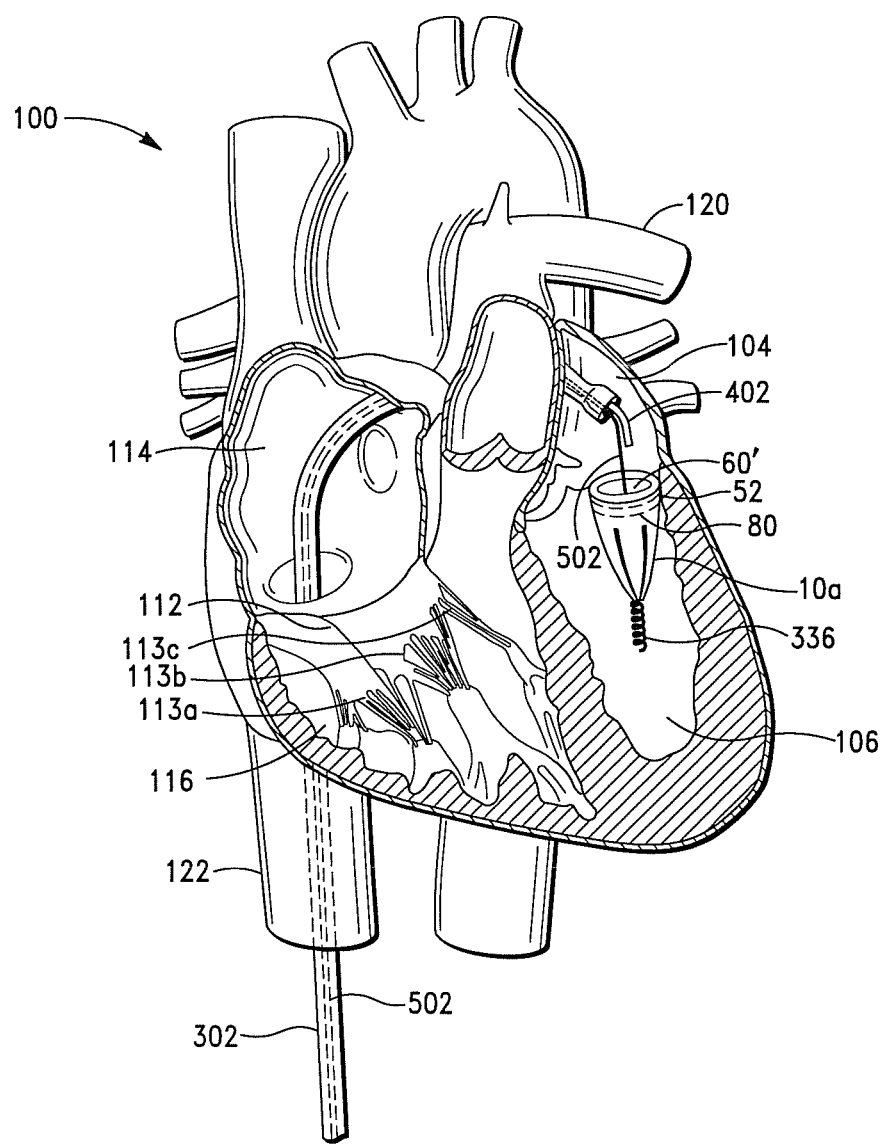
FIG. 29 is a further illustration of the mammalian heart shown in FIG. 19 showing the valve securing device deployed in and extending out of the portal catheter, in accordance with the invention.
Figure 30:
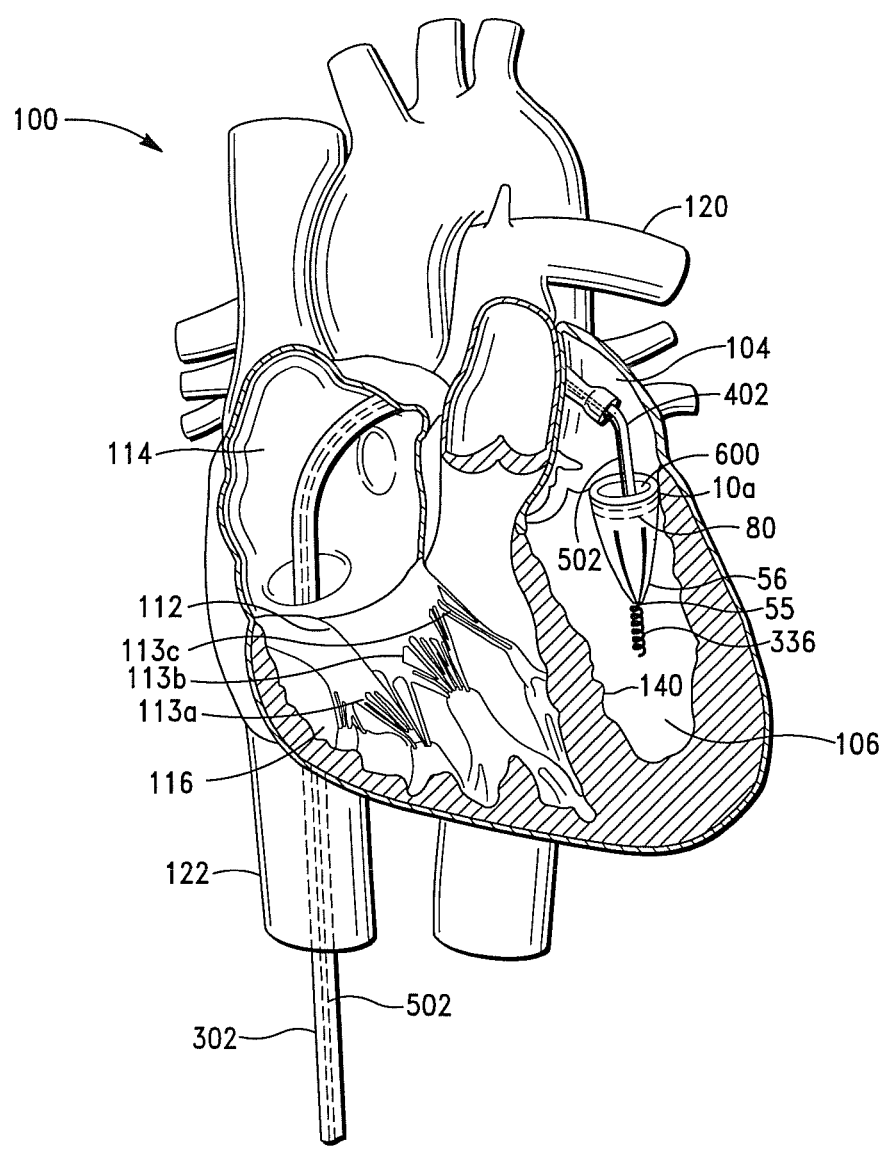
FIG. 30 is a further illustration of the mammalian heart shown in FIG. 19 showing the valve securing device extending into the prosthetic valve shown in FIGS. 28 and 29, in accordance with the invention.
Figure 31:
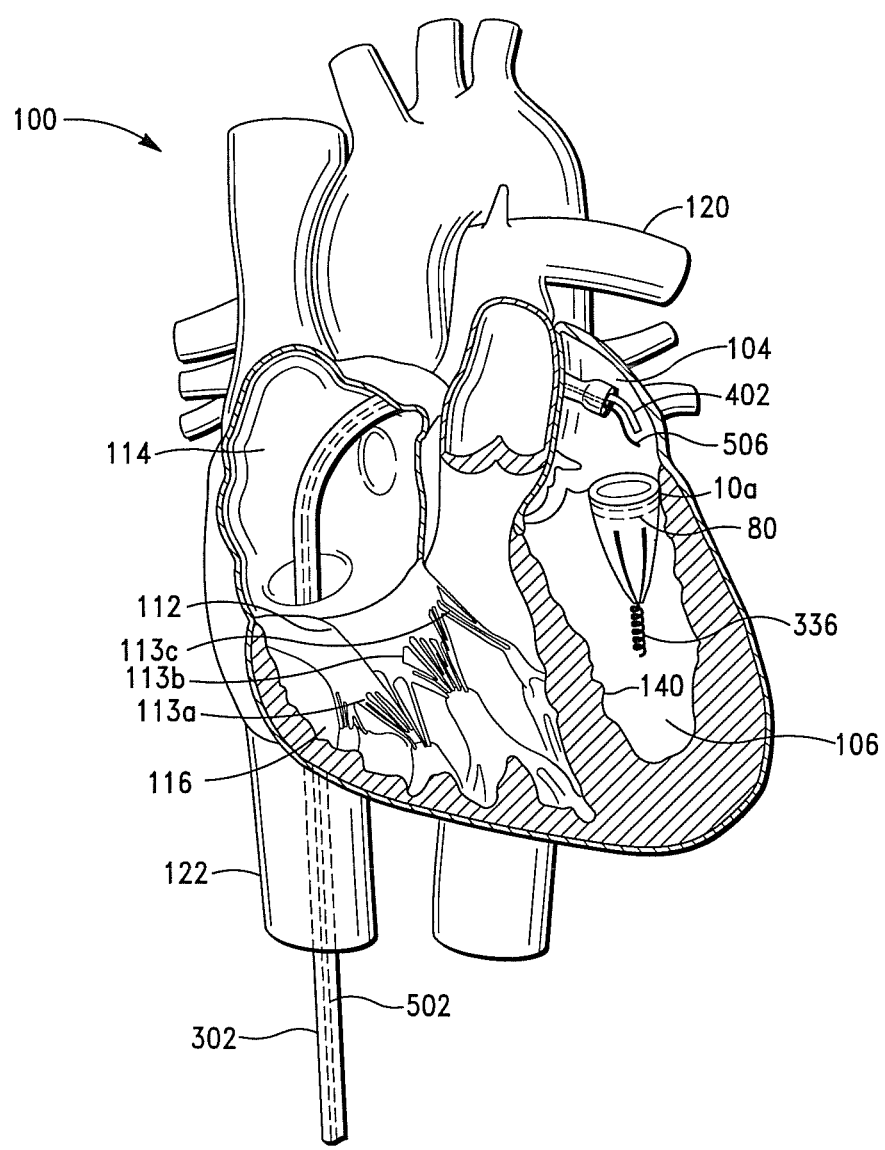
FIG. 31 is a further illustration of the mammalian heart shown in FIG. 19 showing the valve securing device partially retracted in the portal catheter, in accordance with the invention.

As illustrated in FIGS. 29-31, after the prosthetic valve insertion device 350 is retracted through the catheter portal sheath 302 along the anchor guidewire 502 and out of the subject's body (denoted step "xvii"), (xviii) the valve securing device 400; specifically, the securing shaft 402 thereof, is guided into and through the catheter portal sheath 302, into the left atrium 104, through mitral valve 102 (not shown), into the left ventricle 106 and through the proximal annulus engagement end 52 of the prosthetic valve 10a and into the interior region 60' thereof.

After the valve securing device 400 is routed into the interior region 60' of prosthetic valve 10a (denoted step "xviii"), (xix) the distal ends 56b of the ribbons 56 are gathered and ensnared (or captured) with the multi-function distal end 404 of the valve securing device 400 and the ribbon distal ends 56b are engaged to the anchor tip 336 of the anchor guidewire 502, whereby the ribbon distal ends 56b and, hence, distal end 54 of the prosthetic valve 10a are securely engaged to the myocardium 140 of the left ventricle 106.

In some embodiments of the invention, the anchor tip 336 is initially driven a first distance into the myocardium 140, the ribbon distal ends 56b are then placed in communication with the anchor tip 336 (i.e. placed in contact with the anchor tip 336 body) and the anchor tip 336 is thereafter driven a second distance (i.e. further) into the myocardium 140, whereby the ribbon distal ends 56b and, hence, distal end 54 of the prosthetic valve 10a are securely engaged to the myocardium 140 of the left ventricle 106.

After the distal end 54 of the prosthetic valve 10a is securely engaged to the anchor tip 336 and, thereby, myocardium 140 of the left ventricle 106 by the valve securing device 400 (denoted step "xix"), (xx) the multi-functional distal end 404 of the valve securing device 400 is maneuvered to a predetermined point proximate the anchor end 336 and the anchor guidewire 502 is severed by the multi-functional distal end 404 of the valve securing device 400.

As illustrated in FIG. 31, after the anchor guidewire 502 is severed (denoted step "xx"), (xxi) the valve securing device 400 and trailing proximal end 506 of the anchor guidewire 502 are retracted through the catheter portal sheath 302.

According to the invention, a suturing device can then be guided into and through the catheter portal sheath 302 to securely stitch the proximal annulus engagement end 52 of the prosthetic valve 10a to the mitral valve region 124 of mitral valve 120, if necessary or desired.

After the valve securing device 400 and trailing proximal end 506 of the anchor guidewire 502 (and suturing device, if employed) are retracted through the catheter portal sheath 302 (denoted step "xxi"), (xxii) the portal catheter 301 is also retracted from the heart 100 and through the femoral vein 154 and incision 156.

As indicated above, the percutaneous transseptal surgical implantation methods of the invention can also be readily employed to implant the "ribbon structure" prosthetic valves 10f-10k shown in FIGS. 10C-10H and a "sheet structure" prosthetic valve, such as prosthetic valve 10l, discussed above, in a subject.

According to the invention, implantation of "ribbon structure" prosthetic valves 10f-10k similarly comprises steps "ii" through "xviii" above (i.e. the valve securing device 400 is guided into and through the catheter portal sheath 302, into and through the prosthetic valve and into the interior region thereof).

Figure 32:
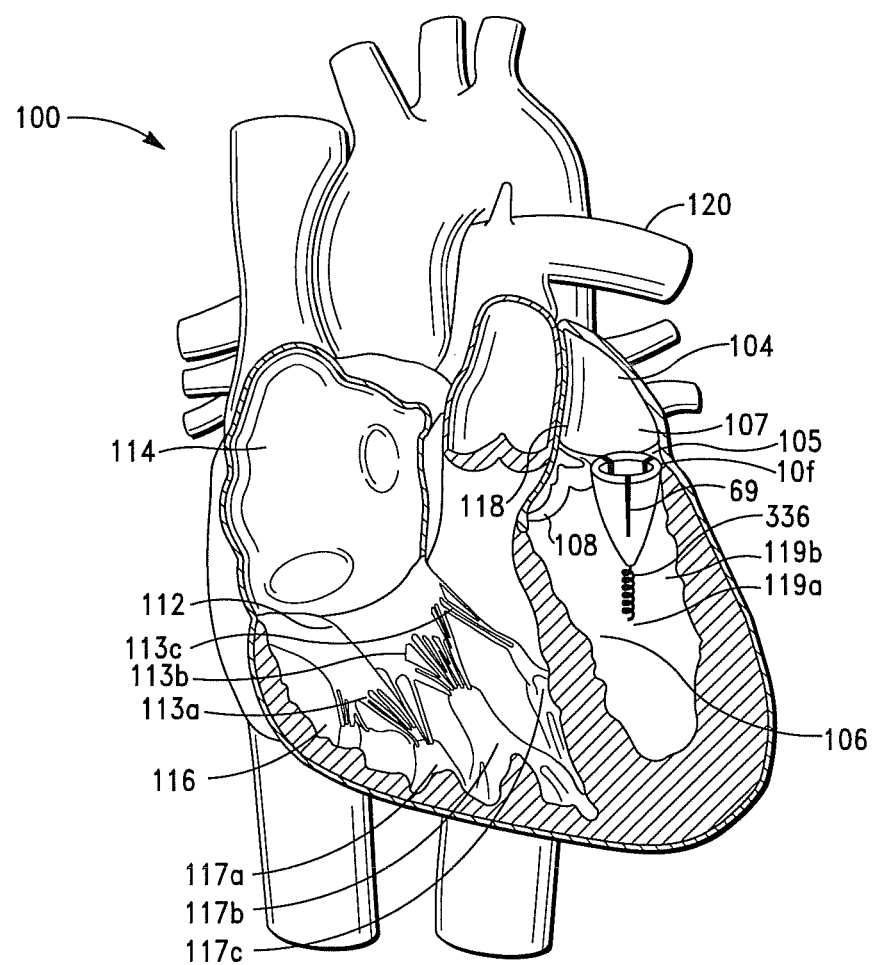
FIG. 32 is a further illustration of the mammalian heart shown in FIG. 19 showing the prosthetic "ribbon structure" valve shown in FIG. 10C positioned in the mitral valve region of the subject's heart with the distal end of the valve engaged to an anchor tip and, thereby, myocardium of the subject's heart, in accordance with the invention.

After the valve securing device 400 is guided into the interior region 60' of prosthetic valve, e.g., valve 10h, the distal end 63 of the valve is ensnared with the multi-function distal end 404 of the valve securing device 400 and the distal end 63 of the valve is engaged to the anchor tip 336 of the anchor guidewire 502, whereby the distal end 63 of the prosthetic valve (i.e. 10f, 10g, 10h, 10i, 10j, 10k) is securely engaged to the myocardium 140 of the left ventricle 106, as shown in FIG. 32.

In some embodiments of the invention, the anchor tip 336 is similarly initially driven a first distance into the myocardium 140, the distal end 63 of the valve, e.g., 10h, is then placed in communication with the anchor tip 336 (i.e. placed in contact with the anchor tip 336 body) and the anchor tip 336 is thereafter driven a second distance (i.e. further) into the myocardium 140, whereby the distal end 63 of the prosthetic valve, e.g., 10h, is securely engaged to the myocardium 140 of the left ventricle 106.

Steps "xx" through "xxii", discussed above, are then similarly performed, whereby prosthetic valve; in this instance, valve 10f, is implanted in the mitral valve region 124 of the heart 100, as shown in FIG. 32.

As set forth in Co-Pending U.S. application Ser. Nos. 16/238,730 and 16/193,669, implantation of a prosthetic "sheet structure" valve, such as valve 10l, similarly initially comprises steps "ii" through "xviii" above (i.e. the valve securing device 400 is guided into and through the catheter portal sheath 302, into and through the prosthetic valve 10l and into the interior region thereof).

Figure 33:
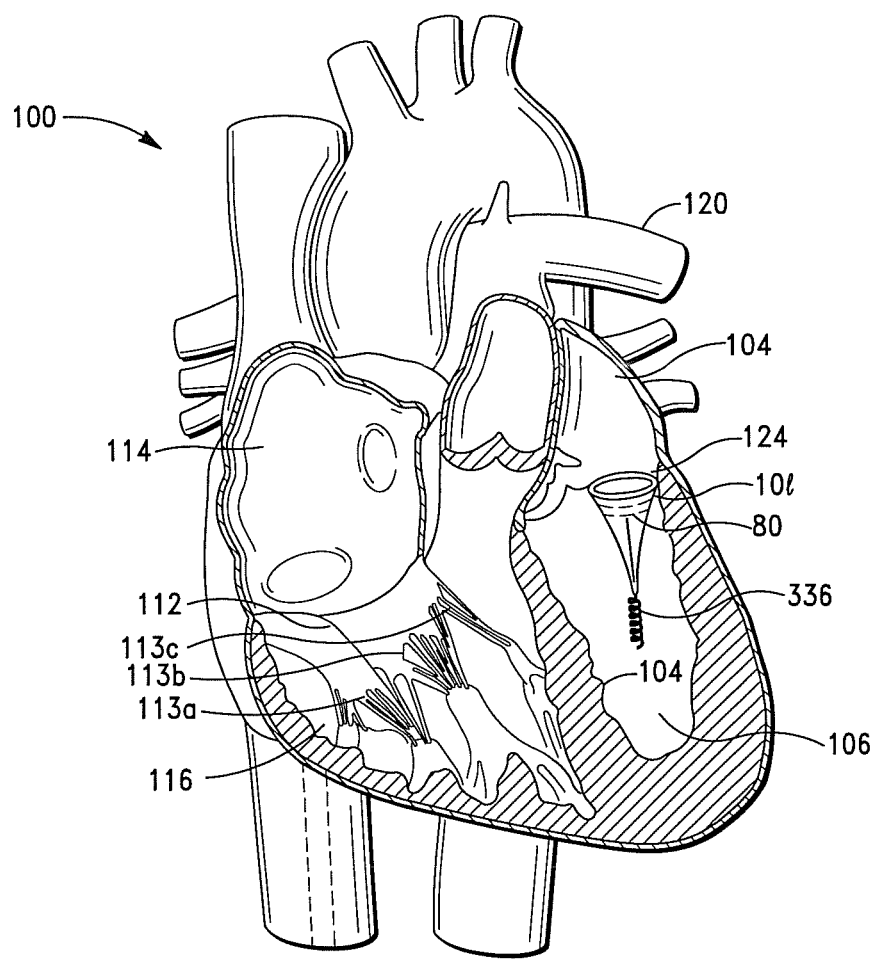
FIG. 33 is a further illustration of the mammalian heart shown in FIG. 19 showing the prosthetic "sheet structure" valve shown in FIG. 11 positioned in the mitral valve region of the subject's heart with the distal end of the valve engaged to an anchor tip and, thereby, myocardium of the subject's heart, in accordance with the invention.

After the valve securing device 400 is guided into the interior region of prosthetic valve 10l, the distal end 34 of the valve 10l is similarly ensnared with the multi-function distal end 404 of the valve securing device 400 and the distal end 34 of the valve 10l is engaged to the anchor tip 336 of the anchor guidewire 502, whereby the distal end 34 of the valve 10l is securely engaged to the myocardium 140 of the left ventricle 106, as shown in FIG. 33.

In some embodiments of the invention, the anchor tip 336 is similarly initially driven a first distance into the myocardium 140, the distal end 34 of the valve 10l is then placed in communication with the anchor tip 336 (i.e. placed in contact with the anchor tip 336 body) and the anchor tip 336 is thereafter driven a second distance (i.e. further) into the myocardium 140, whereby the distal end 34 of the valve 10l is similarly securely engaged to the myocardium 140 of the left ventricle 106.

Steps "xx" through "xxii", discussed above, are then similarly performed, whereby prosthetic valve 10l is implanted in the mitral valve region 124 of the heart 100, as shown in FIG. 33.

Thus, in one embodiment of the invention, there is provided a method for replacing a defective atrioventricular (AV) valve, comprising the steps of:

(i) providing a prosthetic valve, the prosthetic valve comprising a base sheet member comprising polymeric composition, the base sheet member further comprising an open proximal cardiovascular structure engagement region that is configured to engage a valve annulus region, the cardiovascular structure engagement region being further configured to receive fluid flow therein, the base sheet member further comprising a closed distal end region that restricts fluid flow therethrough and a plurality of elongated ribbon members that extend from the closed distal end region toward the open proximal cardiovascular structure engagement region, each of the plurality of elongated ribbon members comprising first and second edge regions and proximal and distal ends, the plurality of elongated ribbon members being positioned circumferentially about the base sheet member, wherein the cardiovascular structure engagement region and an interior region are formed, and wherein the first edge regions of the plurality of elongated ribbon members are positioned proximate the second edge regions of the plurality of elongated ribbon members and form a plurality of fluid flow modulating regions between adjacent elongated ribbon members of the plurality of elongated ribbon members, the base sheet member being configured to transition from an expanded position when the cardiovascular structure engagement region is engaged to the cardiovascular structure and the base sheet member receives fluid flow in the interior region thereof that exhibits a positive flow pressure, to a collapsed position when fluid flow in the interior region exhibits a negative flow pressure, the plurality of fluid flow modulating regions being configured to transition from an open position when the base sheet member is in the expanded position, wherein the plurality of fluid flow modulating regions allow fluid flow to be transmitted through the plurality of fluid flow modulating regions, to a closed position when the base sheet member is in the collapsed position, wherein the plurality of fluid flow modulating regions restrict fluid flow through the plurality of fluid flow modulating regions and, thereby, through the base sheet member;

(ii) providing a catheter assembly adapted to access the AV valve annulus region of a heart, the catheter assembly comprising a portal catheter, catheter guide, anchor insertion device, anchor guidewire, anchor, valve insertion device and valve securing device, the portal catheter comprising a catheter portal sheath comprising portal sheath proximal and distal ends and an access portal therein that is sized and configured to receive and route therethrough the catheter guide, the anchor insertion device, the anchor guidewire, the anchor, the valve insertion device and the valve securing device, the portal catheter further comprising a catheter control assembly adapted to control the portal catheter and, thereby the catheter guide, the anchor insertion device, the anchor guidewire, the anchor, the valve insertion device and the valve securing device when disposed therein, the catheter guide comprising a guide shaft comprising guide shaft proximal and distal ends, an internal guide shaft lumen therein that is sized and configured to receive a first guidewire therein and a guide head disposed on the guide shaft distal end, the guide head being configured to pierce through biological tissue, the anchor insertion device comprising an elongated member comprising an internal anchor insertion device lumen therein that is sized and configured to receive the anchor guidewire and anchor therein, the anchor insertion device further comprising an actuation mechanism adapted to control the elongated member, and the anchor guidewire and anchor when disposed therein, the anchor guidewire comprising guidewire proximal and distal ends, the anchor being disposed on the anchor guidewire distal end, the anchor being configured to engage cardiovascular tissue, the valve insertion device comprising a valve insertion member and a base member comprising proximal and distal ends and a base member internal lumen therein that is adapted to receive pressurized air therein, the valve insertion device further comprising an expandable member disposed on the distal end of the base member, the expandable member being adapted to transition from a pre-deployment configuration to an expanded post-deployment configuration, the valve securing device comprising a securing shaft comprising a proximal end and a multi-function distal end that is adapted to position the anchor in the cardiovascular tissue, engage the closed distal end region of the prosthetic valve and sever guidewires, the valve securing device further comprising at least one valve securing device actuation mechanism that is adapted to control the multi-function distal end;

(iii) preparing a first catheter sub-assembly comprising the portal catheter, catheter guide and first guidewire;

(iv) selecting a vein in communication with a subject's heart for accessing the AV valve annulus region;

(v) placing an incision through tissue proximate the vein and through the vein, wherein an opening is provided in the vein;

(vi) inserting the first catheter sub-assembly through the incision and into and through the vein, and into the right atrium of the subject's heart;

(vii) advancing the first catheter sub-assembly into the left atrium of the subject's heart;

(viii) retracting the catheter guide of the first catheter sub-assembly through the access portal of the portal catheter sheath and out of the subject's body;

(ix) inserting the anchor insertion device and the anchor guidewire into the access portal of the portal catheter sheath;

(x) routing the anchor insertion device through the access portal of the portal catheter sheath and into the left ventricle of the subject's heart;

(xi) positioning the anchor of the guidewire at a predetermined anchor attachment point between anterior and posterior papillary muscles of the left ventricle;

(xii) attaching the anchor to the myocardium of the heart at the anchor attachment point between the anterior and posterior papillary muscles;

(xiii) withdrawing the anchor insertion device through the access portal of the portal catheter sheath, wherein the anchor and the anchor guidewire remain connected to the myocardium;

(xiv) securing the cardiovascular structure engagement region and, thereby, said proximal ends of the plurality of ribbon members of the prosthetic valve to an expandable proximal guide ring that is adapted to transition from a pre-deployment configuration to an expanded post-deployment configuration;

(xv) positioning the prosthetic valve on the expansion member of the valve insertion device, wherein the anchor guidewire is routed into and through the prosthetic valve closed distal end;

(xvi) inserting the valve insertion device with the prosthetic valve engaged thereto into and through the access portal of the portal catheter sheath along the anchor guidewire and into the AV valve annulus region, and positioning the prosthetic valve therein;

(xvii) expanding the expandable member of the valve insertion device, wherein the expandable member and, thereby, the prosthetic valve and the expandable proximal guide ring transition to the expanded, post-deployment configurations, whereby the prosthetic valve is disposed adjacent the AV valve annulus region;

(xviii) retracting the valve insertion device through the access portal of the portal catheter sheath and out of the subject's body;

(xix) inserting the valve securing device into and through the access portal of the portal catheter sheath, and into an interior region of the prosthetic valve;

(xx) ensnaring the distal end of the prosthetic valve with the multi-function distal end of the valve securing device and connecting the distal end of the prosthetic valve to the anchor;

(xxi) positioning the multi-function distal end of the valve securing device at a predetermined guidewire severing point proximate the anchor and severing the anchor guidewire at the guidewire severing point with the valve securing device;

(xxii) withdrawing the valve securing device and the severed anchor guidewire through the access portal of the portal catheter sheath; and (xxiii) withdrawing the catheter portal sheath out of the left atrium of the subject's heart and out of the subject's body.

In some embodiments of the invention, during the prosthetic valve implant procedure described above, a rapid heart rate is induced, wherein blood flow to and through the native AV valve to be replace is reduced, more preferably, abated.

In a preferred embodiment of the invention, the induced heart rate is in the range of approximately 200-300 beats/min., more preferably, approximately 250 beats/min.

In a preferred embodiment, the rapid heart rate is induced for a period of time greater than 5 seconds, more preferably, in the range of 5-20 seconds.

Figure 34:
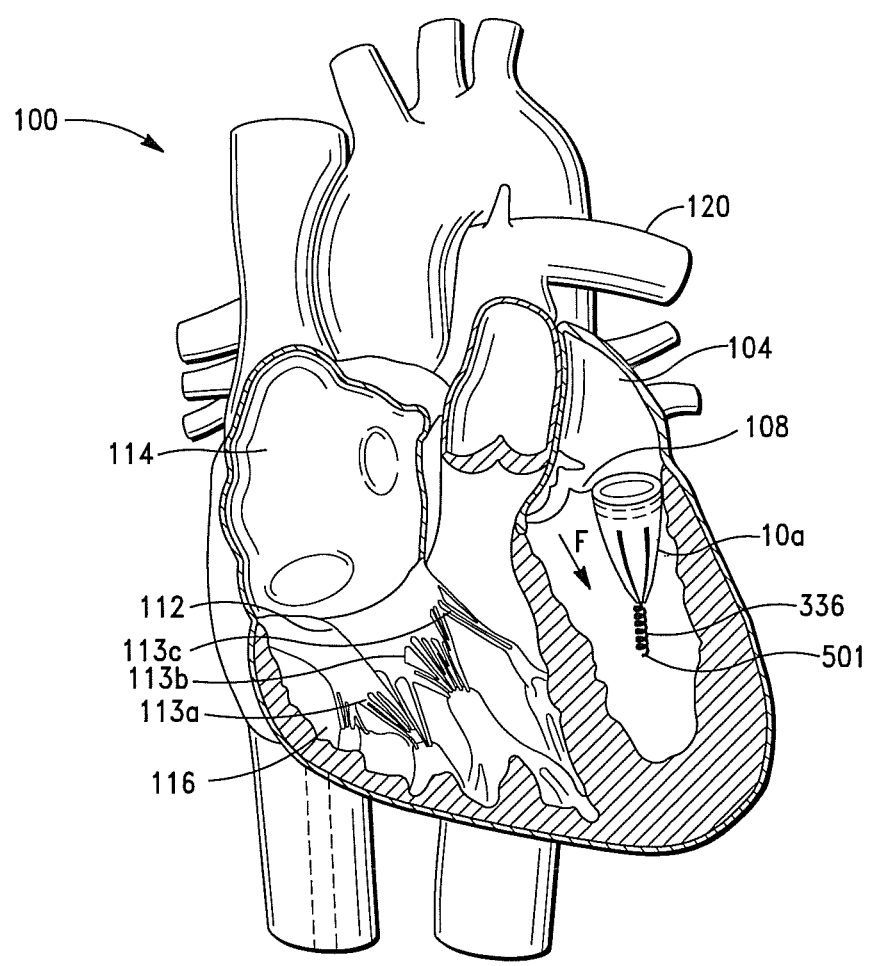
FIG. 34 is a further illustration of the mammalian heart shown in FIG. 19 showing the prosthetic "ribbon structure" valve shown in FIG. 8B positioned in the mitral valve region of the subject's heart with the distal end of the valve engaged to the myocardium of the subject's heart and the blood flow path proximate the valve resulting therefrom, in accordance with the invention.

As illustrated in FIGS. 31-33, prosthetic valves 10a, 10f and 10l are accordingly positioned in mitral valve region 124 of mitral valve 102 with the distal ends of the valves 10a, 10f and 10l being anchored at anchor point 501 on the myocardium. By virtue of the distal ends of the valves 10a, 10f and 10l being anchored at anchor point 501, the body of valves 10a, 10f and 10l are oriented away from the outflow track (denoted "F" in FIG. 34) of aortic valve 108, which allows unobstructed blood flow from the outflow tract. Further, the leaflets of the aortic valve are allowed to freely coapt without obstruction by the body of the valves 10a, 10f and 10l.

As indicated above, when conventional prosthetic valves are implanted in a mitral valve region via conventional means the conventional prosthetic valves will often impair aortic valve function by obstructing the outflow tract of the aortic valve and preventing the leaflets of the adjacent aortic valve from coapting.

As also indicated above, the risks and complications associated with impaired aortic valve function typically include left ventricular hypertrophy with fibrosis, systolic dysfunction (a decrease in the ejection fraction), diastolic dysfunction (elevated filling pressure of the LV), and in severe cases, congestive heart failure.

According to the invention, the prosthetic valves of the invention, including prosthetic valves 10f, 10g, 10h, 10i, 10j and 10k, can also be implanted in the heart of a subject using another embodiment of a novel percutaneous transseptal surgical implantation method of the invention as discussed in detail below.

Referring now to FIGS. 35-41, there is shown another embodiment of catheter assembly 700 of the invention. As set forth in Co-Pending U.S. application Ser. No. 16/238,730, the catheter assembly 700 is similarly configured and adapted to facilitate the deployment of the prosthetic valves of the invention, including prosthetic valves 10f, 10g, 10h, 10i, 10j and 10k discussed above, to a cardiovascular structure, e.g., a valve annulus.

As set forth in Co-Pending U.S. application Ser. No. 16/238,730, the catheter assembly 700 similarly comprises portal catheter 301 and catheter guide 310.

As illustrated in FIGS. 35 and 36, the catheter assembly 700 further comprises an all-in-one (AIO) valve deployment device 701, which is similarly sized and configured to be routed through and retracted from the catheter portal sheath 302 of portal catheter 301 (when employed).

As illustrated in FIG. 35, the AIO valve deployment device 701 preferably comprises a valve insertion member 702 having proximal and distal ends 705, 704, a handle member 718 having an internal lumen 706 therein, and first and second actuation mechanisms 714, 716 disposed on the handle member 718. As further illustrated in FIG. 35, the internal lumen 706 is sized and configured to receive guidewire 502 therein.

Figure 37:
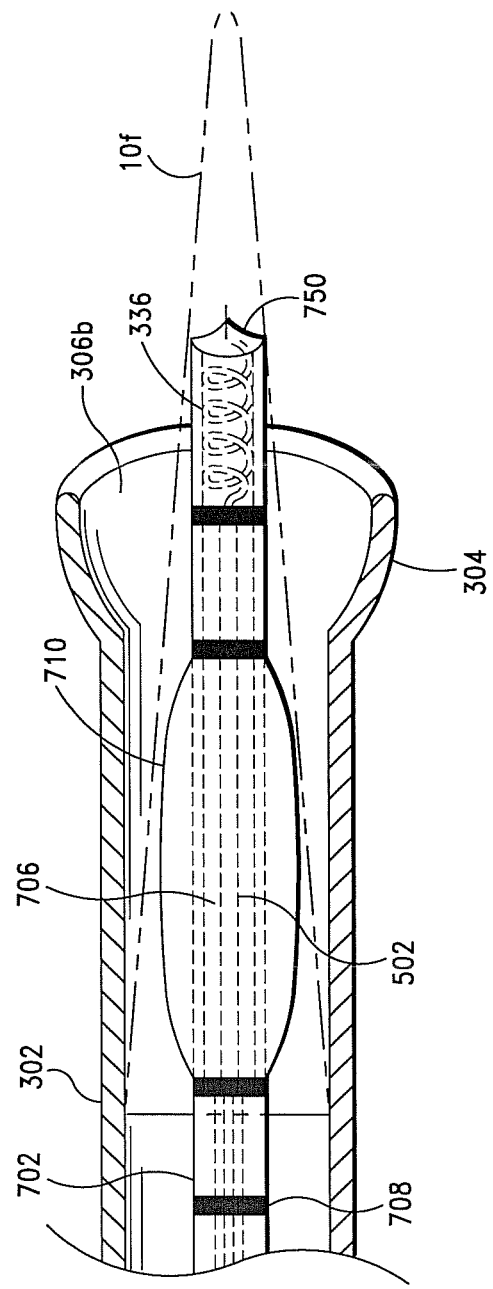
FIG. 37 is a partial front, partial sectional view of another embodiment of a catheter sub-assembly comprising the portal catheter and AIO valve deployment device shown in FIGS. 14A and 35, in accordance with the invention.

As also illustrated in FIGS. 35-37, the valve insertion member 702 further preferably comprises an expandable member 710 disposed proximate the distal end 704 of the insertion member 702 that is configured and adapted to receive a prosthetic valve of the invention; in this instance prosthetic "ribbon structure" valve 10f (see FIGS. 36 and 37), and transition from a pre-deployment configuration to an expanded, post-deployment configuration (as shown in phantom and denoted 712 in FIG. 35).

When the expandable member 710 transitions from a pre-deployment configuration to an expanded, post-deployment configuration 712, the expandable member 710 applies a radial force to the annular ring 90 (or guide ring (when employed)) and, thereby, the prosthetic valve 10f, whereby the annular ring 90 and, hence, prosthetic valve 10f also transition from a pre-deployment configuration to a post-deployment configuration.

As further illustrated in FIG. 35, the handle member 718 of the AIO valve deployment device 701 preferably comprises an air-line or intake 720 that is in communication with an air source 725 via intake tube 722. The air source 725 is preferably configured to provide pressurized air to the expandable member 710 through the handle member 718 internal lumen 706, which allows the expandable member 710 to transition from the unexpanded, pre-deployment configuration to the expanded, post-deployment configuration 712.

As further illustrated in FIGS. 35-37, the AIO valve deployment device 701 also preferably comprises a plurality of markers 708 that are adapted to provide visual guidance for an operator of the AIO valve deployment device 701 during the percutaneous transseptal surgical implantation methods of the invention.

As illustrated in FIGS. 37-41, the AIO valve deployment device 701 further comprises a gating (or catch door) mechanism 750 that is disposed at the valve insertion member 702 distal end 704.

Figure 39:
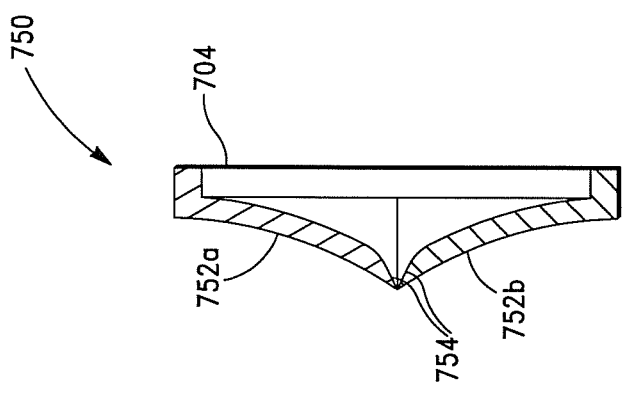
FIG. 39 is a partial front, partial sectional view of the AIO valve deployment device shown in FIG. 35, showing the gating mechanism thereof, in accordance with the invention.
Figure 38:
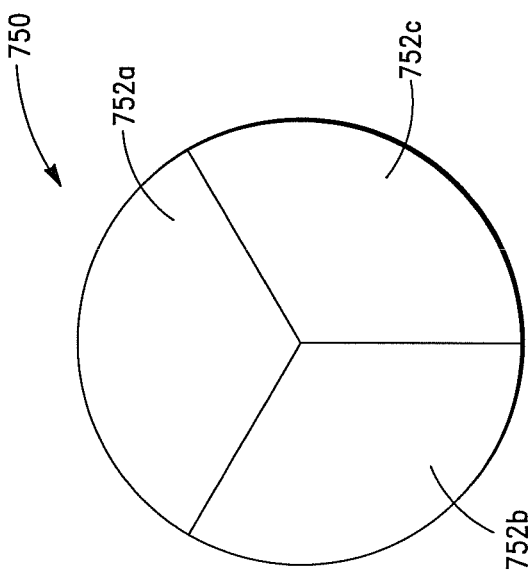
FIG. 38 is a front plan view of the AIO valve deployment device gating mechanism, in accordance with the invention.

As illustrated in FIGS. 38 and 39, the gating mechanism 750 preferably comprises a plurality of door members; in the illustrated embodiment, three (3) door members 752a, 752b, 752c that include bladed edges 754.

As set forth in Co-Pending U.S. application Ser. No. 16/238,730, the gating mechanism 750 door members 752a, 752b, 752c are configured to transition from a closed, coapted configuration to an open configuration (i.e. flex to an open position) when the guidewire 502 anchor tip 336 is guided therethrough. The door members 752a, 752b, 752c also preferably exert a closure force on the guidewire 502 when disposed in the gating mechanism.

The door members 752a, 752b, 752c are preferably further configured to engage the guidewire 502 and increase the closure force applied thereto, when the guidewire 502 is withdrawn or retracted through the gating mechanism 750, wherein the bladed edges 754 of the door members 752a, 752b, 752c sever the guidewire.

As also set forth in Co-Pending U.S. application Ser. No. 16/238,730, the first and second actuation mechanisms 714, 716 are configured to modulate a plurality of functions of the AIO valve deployment device 701, including, but not limited to (i) routing the AIO valve deployment device 701 through the catheter portal sheath 302 and into the mitral valve region of the heart, (ii) expanding the expandable member 710, (iii) guiding the anchor guidewire 502 into and through the gating mechanism 750 and a distal end of a prosthetic valve, e.g., prosthetic valve 10f, (iv) positioning the anchor 336 of the anchor guidewire 502 at a predetermined anchor attachment point and attaching the anchor 336 to the myocardium at the anchor attachment point, and (v) retracting the anchor guidewire 502 through the gating mechanism.

In some embodiments of the invention, when the percutaneous transseptal surgical implantation methods of the invention are performed using catheter assembly 700, the methods similarly comprise steps (i)-(viii), as described above.

After steps (i)-(viii) of the percutaneous transseptal surgical implantation method are complete and the AIO valve deployment device 701 is prepared for the remaining portion of the method, (ix) the prosthetic valve, in this instance prosthetic valve 10f, is positioned on the valve insertion member 702 of the valve insertion device 701 such that the prosthetic valve 10f and annular ring 90 (or guide ring) is positioned over expandable member 710.

After prosthetic valve 10f is positioned on the AIO valve deployment device 701 (denoted step "ix"), (x) the AIO valve deployment device 701 with prosthetic valve 10f engaged thereto is guided into and through the catheter portal sheath 302 and (xi) routed into the mitral valve region 124 (i.e. AV valve annulus region) of heart 100 by an operator.

After the AIO valve deployment device 701 with prosthetic valve 10f engaged thereto is guided into and through the catheter portal sheath 302 and into the mitral valve region 124 (denoted steps "x and xi"), (xii) the expandable member 710 of the valve insertion member 702 is expanded, wherein the expandable member 710 and, thereby, prosthetic valve 10f (and annular ring 90 (or guide ring)) transition from pre-deployment configurations to expanded, post-deployment configurations, whereby prosthetic valve 10f; preferably, the proximal annulus engagement end thereof; is positioned in and, preferably disposed adjacent the mitral valve region 124 of the heart 100.

After the prosthetic valve 10f is deployed in the mitral valve region 124 (denoted step "xii"), (xiii) the anchor tip 336 of guidewire 502 is guided into and through gating mechanism 750 of valve insertion member 702, the prosthetic valve 10f and the distal end 63 thereof.

After the anchor tip 336 of guidewire 502 is guided into and through gating mechanism 750 of valve insertion member 702 and the prosthetic valve 10i distal end 34 (denoted step "xiii"), (xiv) the anchor tip 336 of guidewire 502 is positioned at a predetermined anchor attachment point 501 between the anterior and posterior papillary muscles 119a, 119b of the left ventricle 106.

After the anchor tip 336 is positioned in the left ventricle 106 (denoted step "xiv"), (xv) the anchor tip 336 is driven into and secured to, i.e. engages, the myocardium 140 of the left ventricle 106 at the anchor attachment point 501.

After the anchor tip 336 is engaged to the myocardium 140 (denoted step "xv"), (xvi) the guidewire 502 is retracted through the gating mechanism 750 of the valve deployment member 702, whereby, the guidewire 502 is severed at a predetermined point by the gating mechanism 750 and anchor tip 336 is left secured to the myocardium 140.

After the guidewire 502 is retracted through the gating mechanism 750 of the valve deployment member 702 (denoted step "xvi"), (xvii) the AIO valve deployment device 701 and the trailing end of guidewire 502 are withdrawn through the catheter portal sheath 302 and out of the subject's body.

After the AIO valve deployment device 701 is retracted through the catheter portal sheath 302 and out of the subject's body (denoted step "xvii"), (xviii) the portal catheter 301 is also retracted from the heart 100 and through the femoral vein 154 and incision 156.

EXAMPLES

The following examples are provided to enable those skilled in the art to more clearly understand and practice the present invention. They should not be considered as limiting the scope of the invention, but merely as being illustrated as representative thereof.

Example 1

Assessment of Acute Hemodynamic Function of a Porcine Heart

A study was performed using a porcine model in order to evaluate the acute hemodynamic function of a porcine heart when the mitral valve of the porcine heart is replaced with a prosthetic tissue valve comprising a base ribbon structure, such as the prosthetic tissue valve shown in FIGS. 8A and 8B.

The study included a single treatment group consisting of one (1) adolescent pig (*sus domesticus*). The pig received anesthetic premedication, followed by anesthetic induction via intravenous injection. After the pig was anesthetized, a prosthetic tissue valve comprising a base ribbon structure was implanted into the mitral valve region of the porcine heart.

During the implantation procedure, the distal end of the prosthetic tissue valve was secured to a predetermined region of the left ventricle myocardium between the anterior and posterior papillary muscles of the porcine heart.

Approximately two (2) hours after the implantation procedure, an echocardiogram was performed on the pig to assess the acute hemodynamic function of the porcine heart.

Figure 42:
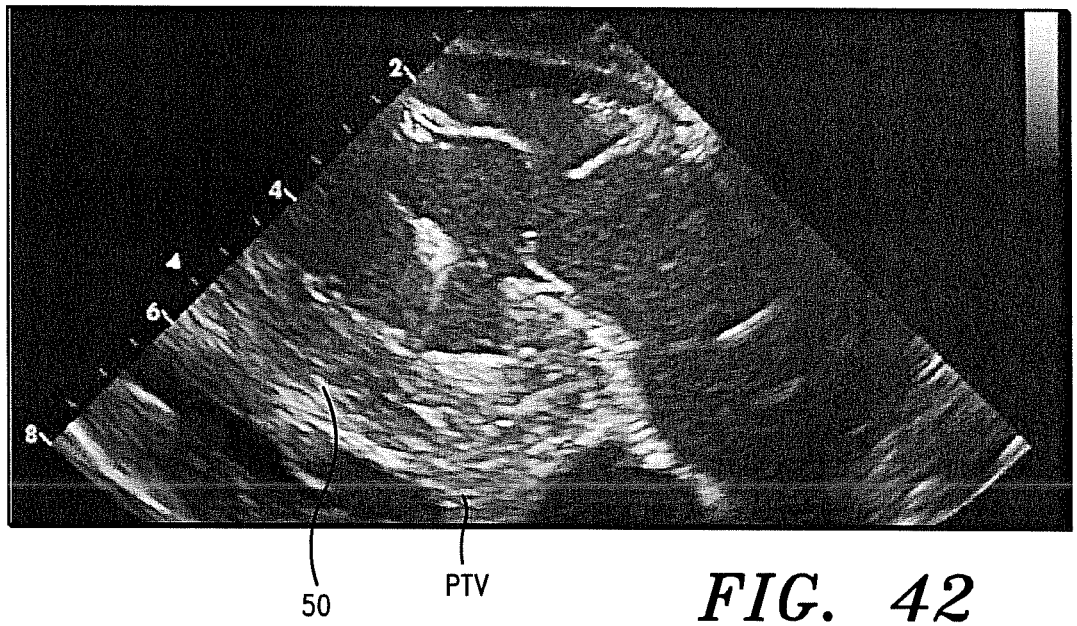
FIGS. 42 and 43 are echocardiograms of an adolescent pig post-implant (~2 hrs.) of a prosthetic ribbon structure valve, showing full function of the valve, in accordance with the invention.
Figure 43:
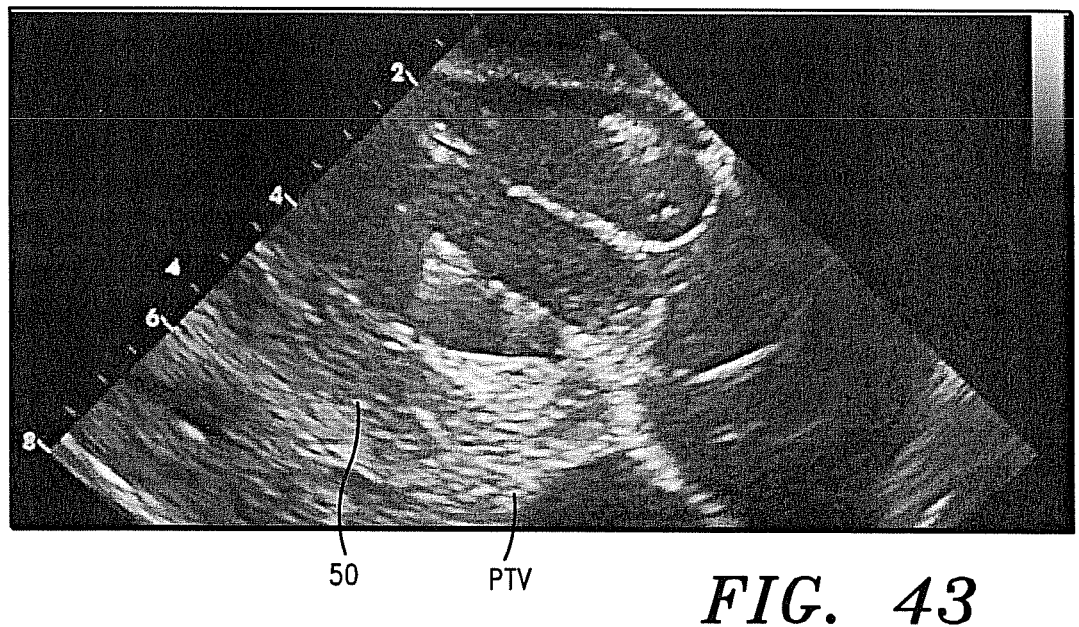

Referring now to FIGS. 42 and 43, there are shown the echocardiogram images of the porcine heart with the prosthetic tissue valve denoted "PTV" and base ribbon structure denoted "50" implanted in the mitral valve region. FIG. 42 shows the prosthetic tissue valve "PVT" in a contracted state, wherein negative fluid flow through base ribbon structure 50 is restricted. FIG. 43 shows the prosthetic tissue valve "PVT" in an expanded state, wherein positive fluid flow is being transmitted through the fluid flow modulating regions (denoted "59" in FIG. 8B above) of the base ribbon structure 50.

The echocardiogram images thus reflect that acute hemodynamic function was provided with the implanted prosthetic tissue valve of the invention.

As indicated above, the novel percutaneous transseptal surgical implantation methods of the invention can be readily employed to effectively position and secure the prosthetic valves of the invention to a cardiovascular structure, i.e., a valve annulus region, of a heart. As will readily be appreciated by one having ordinary skill in the art, the percutaneous transseptal surgical implantation methods and prosthetic valves deployed therewith provide numerous advantages over convention valve implantation methods and prosthetic valves. Among the advantages are the following:

The provision of a percutaneous transseptal surgical implantation method that provides a highly effective means for positioning and securing a prosthetic valve to a cardiovascular structure.

The provision of a percutaneous transseptal surgical implantation method that positions a prosthetic valve in a mitral valve region, whereby the valve does not obstruct the outflow tract of the adjacent aortic valve and prevents the leaflets of the aortic valve from coapting.

The provision of prosthetic valves, which, when implanted in a subject, gradually remodel the ECM into cardiovascular tissue and tissue (and, hence, valve) structures that are similar to native structures.

The provision of prosthetic valves, which, when disposed proximate a cardiovascular structure, induce modulated healing of the cardiovascular structure and associated tissue.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method for replacing a defective heart valve, comprising the steps of:

(i) providing a prosthetic valve, said prosthetic valve comprising a base sheet member comprising a polymeric composition, said base sheet member further comprising an open proximal cardiovascular structure engagement region that is configured to engage an AV valve annulus region, said open proximal cardiovascular structure engagement region being further configured to receive fluid flow therein, said base sheet member further comprising a closed distal end region that restricts fluid flow therethrough and a plurality of elongated ribbon members that extend from said closed distal end region toward said open proximal cardiovascular structure engagement region, each of said plurality of elongated ribbon members comprising first and second edge regions and proximal and distal ends, said plurality of elongated ribbon members being positioned circumferentially about said base sheet member where said open proximal cardiovascular structure engagement region is formed, and wherein said first edge regions of said plurality of elongated ribbon members are positioned proximate said second edge regions of said plurality of elongated ribbon members and form a plurality of fluid flow modulating regions between adjacent elongated ribbon members of said plurality of elongated ribbon members, said base sheet member being configured to expand to an expanded valve configuration when said open proximal cardiovascular structure engagement region is engaged to said AV valve annulus region and said base sheet member receives first fluid flow therein that exhibits a positive flow pressure and contracts to a contracted valve configuration when said base sheet member receives second fluid flow that exhibits a negative flow pressure, said plurality of fluid flow modulating regions being configured to open during said expansion of said base sheet member to said expanded valve configuration, wherein said plurality of fluid flow modulating regions allow said first fluid flow in said base sheet member to be transmitted through said plurality of fluid flow modulating regions, and close during said contraction of said base sheet member to said contracted valve configuration, wherein said plurality of fluid flow modulating regions restrict said second fluid flow through said plurality of fluid flow modulating regions and, thereby, through said base sheet member;

(ii) providing a catheter assembly adapted to access said AV valve annulus region of a heart, said catheter assembly comprising a portal catheter, catheter guide, anchor insertion device, anchor guidewire, anchor, valve insertion device and valve securing device, said portal catheter comprising a catheter portal sheath comprising proximal and distal ends and an access portal therein that is sized and configured to receive and route therethrough said catheter guide, said anchor insertion device, said anchor guidewire, said anchor, said valve, insertion device and said valve securing device, said portal catheter further comprising a catheter control assembly adapted to control said portal catheter and, thereby said catheter guide, said anchor insertion device, said anchor guidewire, said anchor, said valve insertion device and said valve securing device when disposed therein, said catheter guide comprising a guide head and a guide shaft having an internal guide lumen therein that is sized and configure to receive a first guidewire therein, said guide head being configured to pierce through biological tissue, said anchor insertion device comprising an elongated member having an internal anchor insertion device lumen therein that is sized and configured to receive said anchor guidewire and anchor therein, said anchor insertion device further comprising an actuation mechanism adapted to control said elongated member, said anchor guidewire and anchor when disposed therein, said anchor guidewire comprising proximal and distal ends, said anchor being disposed on said anchor guidewire distal end, said anchor being configured to engage cardiovascular tissue, said valve insertion device comprising a valve insertion member and a base member comprising proximal and distal ends and a base member internal lumen therein that is adapted to receive pressurized air therein, said valve insertion device further comprising an expandable member disposed on said distal end of said base member, said expandable member being adapted to transition from a pre-deployment configuration to an expanded post-deployment configuration, said valve securing device comprising a securing shaft comprising a proximal end and a mold-function distal end that is adapted to position said anchor in said cardiovascular tissue, engage said closed distal end region of said prosthetic valve and sever a guidewire, said valve securing device further comprising at least one valve securing device actuation mechanism that is adapted to control said mold-function distal end;

(iii) preparing a first catheter sub-assembly comprising said portal catheter, said catheter guide and said first guidewire;

(iv) selecting a vein in communication with a subject's heart, said vein providing access to an AV waive annulus region of said subject's heart;

(v) placing an incision through tissue proximate said vein and through said vein, wherein an opening is provided in said vein;

(vi) inserting said first catheter sub-assembly through said incision and into and through said vein, and into a right atrium of said subject's heart;

(vii) advancing said first catheter sub-assembly into a left atrium of said subject's heart;

(viii) retracting said catheter guide and said first guidewire through said access portal of said catheter portal sheath and out of said subject's body;

(ix) inserting said anchor insertion device and said anchor guidewire into said access portal of said catheter portal sheath;

(x) routing said anchor insertion device through said access portal of said catheter portal sheath and into a left ventricle of said subject's heart;

(xi) positioning said anchor of said anchor guidewire at a predetermined anchor attachment point between anterior and posterior papillary muscles;

(xii) attaching said anchor to myocardium of said subject's heart at said predetermined anchor attachment point;

(xiii) withdrawing said anchor insertion device through said access portal of said catheter portal sheath, wherein said anchor and said anchor guidewire remain connected to said myocardium;

(xiv) securing said open proximal cardiovascular structure engagement region and, thereby said proximal ends of said plurality of elongated ribbon members of said prosthetic valve to an expandable proximal guide ring, said expandable proximal guide ring being adapted to transition from a guide ring pre-deployment configuration to a guide ring expanded post-deployment configuration;

(xv) positioning said prosthetic valve on said expandable member of said valve insertion device, wherein said anchor guidewire is routed into and through said prosthetic valve closed distal end region;

(xvi) inserting said valve insertion device with said prosthetic valve engaged thereto into and through said access portal of said catheter portal sheath along said anchor guidewire and into said AV valve annulus region of said subject's heart;

(xvii) positioning said prosthetic valve in said AV valve annulus region;

(xviii) expanding said expandable member of said valve insertion device, wherein said expandable member expands to said expanded post-deployment configuration and, thereby, said base sheet member of said prosthetic valve expands to said expanded valve configuration and said expandable proximal guide ring expands to said guide ring expanded post-deployment configuration, whereby said prosthetic valve is disposed adjacent said AV valve annulus region;

(xix) retracting said valve insertion device through said access portal of said catheter portal sheath and out of said subject's body;

(xx) inserting said valve securing device into and through said access portal of said catheter portal sheath, and into an interior region of said base sheet member of said prosthetic valve;

(xxi) ensnaring said closed distal end region of said prosthetic valve with said multi-function distal end of said valve securing device;

(xxii) connecting said closed distal end region of said base sheet member of said prosthetic valve to said anchor, whereby said prosthetic valve is engaged to said myocardium;

(xxiii) positioning said multi-function distal end of said valve securing device at a predetermined anchor guidewire severing point proximate said anchor;

(xxiv) severing said anchor guidewire at said predetermined anchor guidewire severing point with said valve securing device;

(xxv) withdrawing said valve securing device and said severed anchor guidewire through said access portal of said catheter portal sheath;

(xxvi) inserting a suturing device into and through said access portal of said catheter portal sheath to said open proximal cardiovascular structure engagement region of said base sheet member of said prosthetic valve;

(xxvi) suturing said open proximal cardiovascular structure engagement region to the AV valve annulus region; and (xxviii) withdrawing said catheter portal sheath out of said left atrium of said subject's heart and out of said subject's body.

2. The method of claim 1, wherein said step of inserting said first catheter sub-assembly through said incision and into said right atrium of said subject's heart further comprises routing said first catheter sub-assembly up a common iliac vein and into an inferior vena cava.

3. The method of claim 1, wherein said step of advancing said first catheter sub-assembly into said left atrium of said subject's heart further comprises routing said first catheter sub-assembly through a predetermined region of an atrial septum of said subject's heart.

4. The method of claim 1, wherein during said method a rapid heart rate is induced in said subject's heart, wherein blood flow to and through said AV valve annulus region is reduced.

* * * * *

UNITED STATES PATENT AND TRADEMARK OFFICE
CERTIFICATE OF CORRECTION

PATENT NO. : 10,945,838 B2
APPLICATION NO. : 16/553570
DATED : March 16, 2021
INVENTOR(S) : Robert G Matheny It is certified that error appears in the above-identified patent and that said Letters Patent is hereby corrected as shown below:

On the Title Page

First Column, item (73) the name of the Assignee:
Please delete "Co-Matrix Cardiovascular, Inc."
And substitute therefor -- CorMatrix Cardiovascular, Inc. --.

Signed and Sealed this
Second Day of July, 2024

Katherine Kelly Vidal
*Director of the United States Patent and Trademark Office*